United States Patent
Dernebo et al.

(10) Patent No.: US 12,420,083 B2
(45) Date of Patent: Sep. 23, 2025

(54) MEDICAL THERAPY ARRANGEMENT FOR APPLYING AN ELECTRICAL STIMULATION TO A HUMAN OR ANIMAL SUBJECT

(71) Applicant: Exoneural Network AB, Danderyd (SE)

(72) Inventors: Lars Dernebo, Odeshög (SE); Fredrik Lundqvist, Stockholm (SE)

(73) Assignee: Exoneural Network AB, Danderyd (SE)

( * ) Notice: Subject to any disclaimer, the term of this patent is extended or adjusted under 35 U.S.C. 154(b) by 741 days.

(21) Appl. No.: 16/796,970

(22) Filed: Feb. 21, 2020

(65) Prior Publication Data

US 2020/0188653 A1    Jun. 18, 2020

Related U.S. Application Data

(63) Continuation-in-part of application No. 16/747,008, filed on Jan. 20, 2020, now abandoned, which is a
(Continued)

(30) Foreign Application Priority Data

Jun. 26, 2012   (SE) ...................................... 1250685

(51) Int. Cl.
*A61N 1/04* (2006.01)
*A61N 1/36* (2006.01)
*A61N 1/372* (2006.01)

(52) U.S. Cl.
CPC ......... *A61N 1/0484* (2013.01); *A61N 1/0476* (2013.01); *A61N 1/3603* (2017.08);
(Continued)

(58) Field of Classification Search
CPC ................ A61N 1/0484; A61N 1/3603; A61N 1/36034; A61N 1/0452; A61N 1/0456; A61N 1/36003
See application file for complete search history.

(56) References Cited

U.S. PATENT DOCUMENTS

2002/0077688 A1 *   6/2002   Kirkland ............ A61N 1/36034
                                                              607/142
2004/0082979 A1 *   4/2004   Tong .................. A61N 1/36003
                                                              607/48

(Continued)

OTHER PUBLICATIONS

International Search Report (ISR) for PCT/2020/021018, 3 pages. Mailing date of Jun. 10, 2020. (Year: 2020).*

*Primary Examiner* — Pamela M. Bays
(74) *Attorney, Agent, or Firm* — Goodwin Procter LLP

(57) ABSTRACT

The garment has a first sub-control unit or master unit electrically connected to a first electrode and a second electrode placed at a first muscle or first nerve and a third electrode and a fourth electrode placed at a second muscle or second nerve. The garment has sensors attached to the garment and electrically connected to the first sub-control unit or master unit. The sensors measure position, electrical signals or movement of the patient wearing the garment. The first sub-control or the master unit receives information about the position or movement and comparing the position, electrical signals or movement to an interval of pre-stored desirable positions, electrical signals levels or movement. When the position, electrical signals or movement is outside the interval, the master unit sends through the first sub-control unit a stimulation signal to the first muscle to cause or facilitate a contraction of the first muscle.

10 Claims, 22 Drawing Sheets

Related U.S. Application Data continuation of application No. 16/746,900, filed on Jan. 19, 2020, now abandoned, which is a continuation of application No. 16/746,826, filed on Jan. 18, 2020, now abandoned, which is a continuation of application No. 16/745,392, filed on Jan. 17, 2020, now abandoned, which is a continuation of application No. 16/697,254, filed on Nov. 27, 2019, now abandoned, which is a continuation of application No. 16/695,829, filed on Nov. 26, 2019, now abandoned, which is a continuation of application No. 16/680,310, filed on Nov. 11, 2019, now Pat. No. 11,260,218, which is a continuation of application No. 16/356,085, filed on Mar. 18, 2019, now Pat. No. 10,987,508, which is a continuation-in-part of application No. 14/410,965, filed as application No. PCT/SE2013/050700 on Jun. 17, 2013, now Pat. No. 10,279,164.

(60) Provisional application No. 61/664,282, filed on Jun. 26, 2012.

(52) U.S. Cl.
CPC .......... *A61N 1/0452* (2013.01); *A61N 1/0456* (2013.01); *A61N 1/0492* (2013.01); *A61N 1/36003* (2013.01); *A61N 1/36021* (2013.01); *A61N 1/36034* (2017.08); *A61N 1/37247* (2013.01)

(56) References Cited

U.S. PATENT DOCUMENTS

| | | | |
|---|---|---|---|
| 2009/0062884 A1* | 3/2009 | Endo | A61N 1/36003 607/49 |
| 2012/0245483 A1* | 9/2012 | Lundqvist | A61B 5/296 600/546 |
| 2016/0213924 A1* | 7/2016 | Coleman | A61N 1/0452 |
| 2018/0126158 A1* | 5/2018 | Perez | A61B 5/1116 |

* cited by examiner

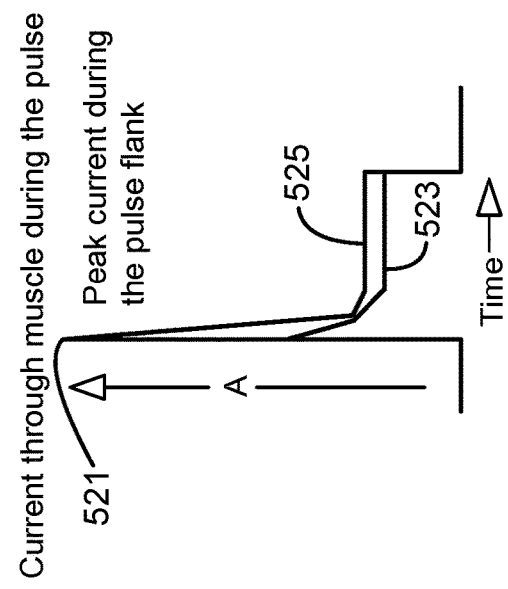
FIG. 11C  Voltage pulse
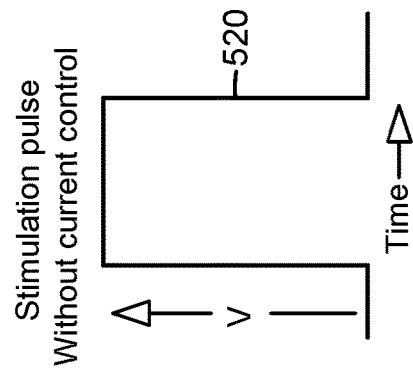
FIG. 11D
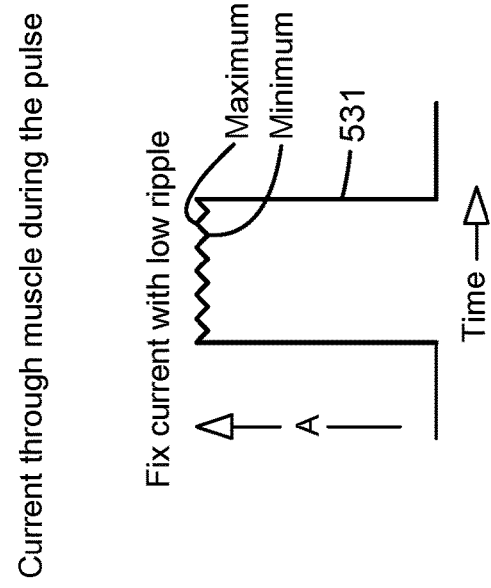
FIG. 11A  Constant current pulse
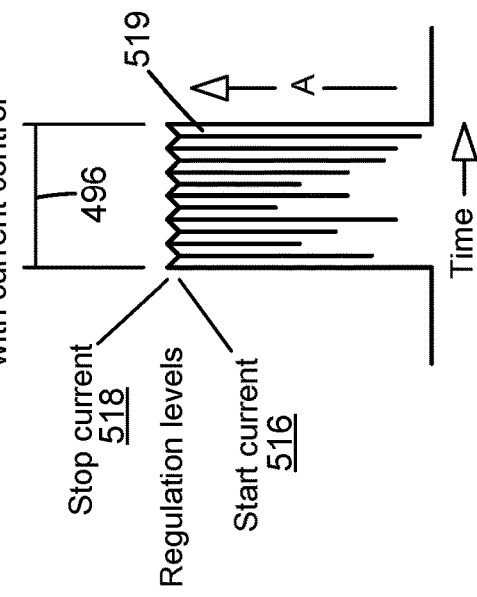
FIG. 11B

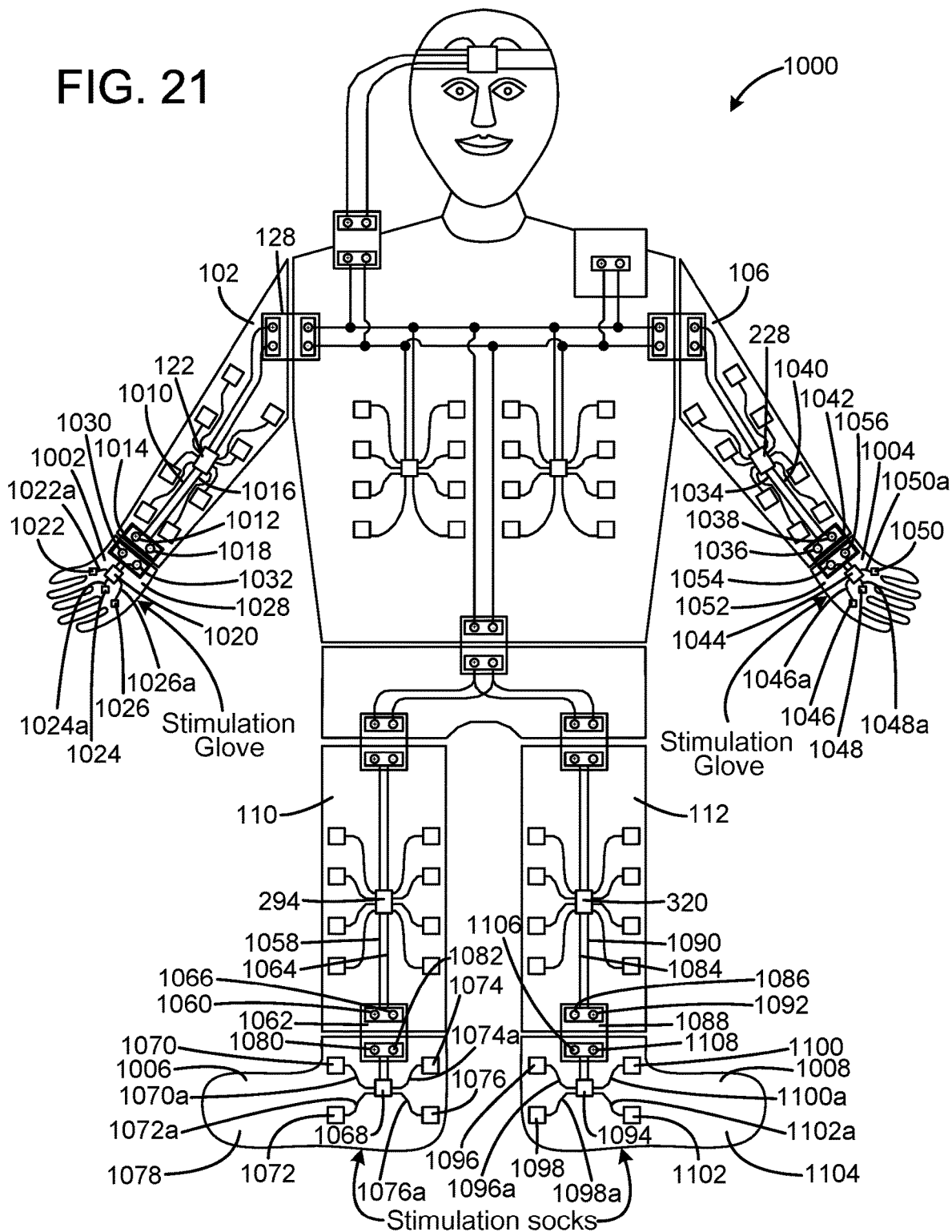

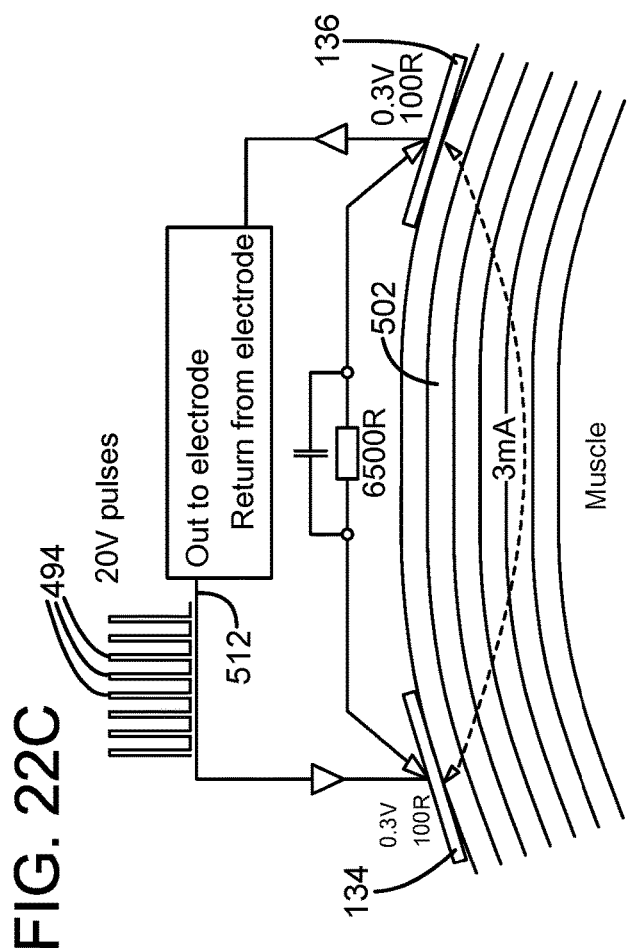
FIG. 22C
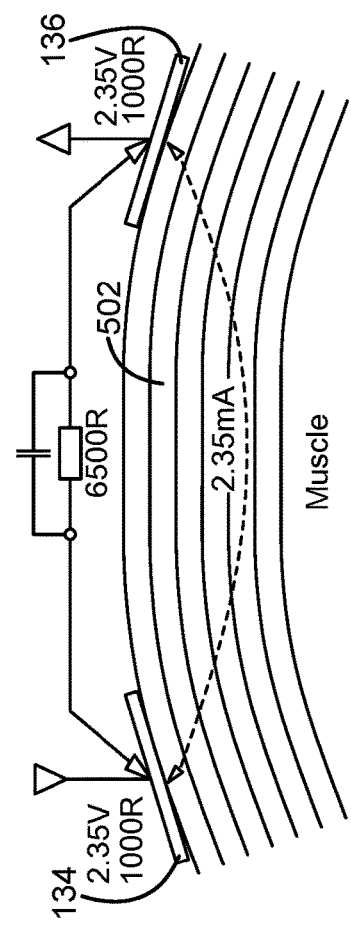
FIG. 22D
FIG. 22A
FIG. 22B

MEDICAL THERAPY ARRANGEMENT FOR APPLYING AN ELECTRICAL STIMULATION TO A HUMAN OR ANIMAL SUBJECT

PRIOR APPLICATIONS

This is a continuation-in-part patent application that claims priority from continuation patent application Ser. No. 16/747,008, filed 20 Jan. 2020 that claims priority from U.S. patent application Ser. No. 16/746,900, filed 19 Jan. 2020 that claims priority from U.S. patent application Ser. No. 16/746,826, filed 18 Jan. 2020 that claims priority from U.S. patent application Ser. No. 16/745,392, filed 17 Jan. 2020 that claims priority from U.S. patent application Ser. No. 16/697,254, filed 27 Nov. 2019 that claims priority from U.S. patent application Ser. No. 16/695,829, filed 26 Nov. 2019 that claims priority from U.S. patent application Ser. No. 16/680,310, filed on 11 Nov. 2019, now issued as U.S. Pat. No. 11,260,218 that claims priority from U.S. patent application Ser. No. 16/356,085, filed on 18 Mar. 2019, now issued as U.S. Pat. No. 10,987,508 that claims priority from U.S. patent application Ser. No. 14/410,965, filed on 23 Dec. 2014, now issued as U.S. Pat. No. 10,279,164 that claims priority from PCT patent application no. PCT/SE2013/050700, filed on 17 Jun. 2013 that claims priority from U.S. Patent Application No. 61/664,282, filed on 26 Jun. 2012 and Swedish Patent Application No. 1250685, filed on 26 Jun. 2012.

FIELD OF THE INVENTION

The present invention relates to a medical therapy arrangement.

BACKGROUND OF THE INVENTION

The present invention relates in general to muscle relaxation, and more particular to muscle relaxation for spastic muscles in patients having injuries to the central nervous system (CNS) at least by using muscle stimulation.

Injuries to the central nervous system (CNS) are difficult to treat and cure. Spastic paresis, which is a pathologically increased muscle tonus caused by an injury to the central nervous system (CNS) is a significant obstacle for prevention of posturing and loss of mobility.

Today, therapeutic alternatives for the reversal of CNS injury symptoms, such as spasticity, are very limited. Therapies are constructed to prevent further loss of function, rather than alleviating the symptoms. No treatment has been found to truly give back function and, in the long run, reversing the injury through muscle relaxation of spastic muscles.

In addition to the spasms themselves, musculoskeletal pain is a common related complaint. Pain originating from dysfunction in the musculoskeletal system is in most cases caused by muscle spasms due to muscular imbalance. If the pain is not treated properly, patients risk developing chronic pain syndromes, conditions that are difficult to cure.

There are several techniques available to affect muscles in the human body. Electrical muscle stimulation (EMS), also known as neuromuscular electrical stimulation or electro-myo-stimulation is a commonly known method for increasing muscle mass in specific areas, by providing an electric current into the muscle causing contraction, which gradually leads to increased mass in the treated muscle.

Transcutaneous Electrical Nerve Stimulation (TENS) is closely related to EMS, but instead of stimulating muscles to contract, electric stimulation is used to indirectly treat pain, by distracting the brain through the stimulation of other body parts. In U.S. Pat. No. 4,580,572, a garment for electrical monitoring of sites or electrical stimulation, such as EMS is disclosed.

However, none of the currently known muscle stimulation techniques is suited to provide for targeted muscle relaxation. Hence, a new arrangement including a garment allowing for increased muscle relaxation would be advantageous.

In general, the parameters of the EMS current signal may be chosen which resemble the physiology of the body. The signals in the nervous system may be compared to current impulses (stimuli) to the synapses. When a certain amount of stimuli has occurred, signal substances are excreted.

Generally, a phasic EMS-stimulus is given with a frequency ranging between 2 and 50 Hz, and having a duration between 5 to 300 microseconds.

Muscle relaxation in spastic muscles gives the possibility to induce controlled functional muscle contraction in chosen relaxed muscles. The frequency needed to induce muscle contraction is higher than the frequency used for optimal antagonist muscle relaxation (20 Hz/30 µs). Stimulation frequencies for functional muscle contraction are ranging from 25 to 50 Hz and the duration needed is between 50-300 µs.

The pulsed EMS current signal is controlled by at least the following parameters; pulse frequency, pulse duration, pulse strength.

Experiments have shown that muscles start to contract at a pulse frequency of approximately 15 Hz to approximately 35 Hz, at which frequency range the central nervous system feels the presence of the current signal. The present inventor has realized that by choosing a frequency as low as possible, but still detectable by the central nervous system, the discomfort for the patient is reduced, while the automatic relaxation of the spastic antagonist muscle is taken care of by the central nervous system. A higher frequency than approximately 35 Hz would lead to shortening of the stimulated agonist muscle and therefore activation of the stretch reflex in the antagonist muscle which is not desired, since this would lead to a reciprocal spasm of the agonist muscle.

The pulse duration of the current signal is selected such that it resembles the pulse duration of nervous signals. For example, a pulse duration of approximately 5 to 60 microseconds, such as 30 µs, has been found to be suitable. However, even shorter pulse duration could be advantageous. Too long pulse duration of the EMS current signal does not correspond to the neurophysiologic parameters of the body.

Furthermore, longer pulse duration may also increase the risk of muscle shortage, which is not desired.

Since the spastic muscle behavior in CNS injured patients differs greatly, the professional skills of a neuromuscular system specialist are required for calibrating the system before use, such that the correct agonist muscles are provided with EMS electrodes and joints corresponding thereto are provided with vibrator devices. Every chosen muscle stimulation is paired with an anatomically relevant joint stimulation in order to strengthen the desired relaxation effect. Furthermore, the parameters of the pulsed EMS current signal need to be selected, which parameters may differ between patients.

The above-described stimulation and calibration techniques are further disclosed in WO-2011/067327, which relates to a system and garment for muscle relaxation of a spastic muscle, and is assigned to the applicant of the present application. In particular the system is adapted to cause muscle relaxation by reducing muscular spasticity through stimulation of joints and muscles. The system consists of a garment with electrodes, a hardware unit and software controlling the stimulation.

WO-03/006106 relates to a method and apparatus for electrical stimulation to selected tissues via an array of electrodes positioned on and/or in the body. Each electrode may be connected either as anode, cathode or neither to provide discrimination between stimulated and non-stimulated regions of tissues of the body.

Today, when performing external electrical stimulation therapy, it is common to use electrode patches provided with an adhesive for attaching the electrodes to the patient's skin. These electrode patches are disposable, and it is often very time-consuming to attach the electrodes and to connect the electrical cables to each of the electrode patches.

The object of the present invention is to achieve an improved stimulation therapy arrangement, which is more user-friendly and less time-consuming to use, than the presently used adhesive electrodes.

As an electrical stimulation therapy preferably must be applied at least 30 minutes in order to give prolonged effect, one further and important aspect of the stimulation therapy arrangement is that it is comfortable and easy to use for the wearer.

SUMMARY OF THE INVENTION

One great advantage of the arrangement according to the present invention is that it is easy to use. This is, among other things, related to that the control unit that includes the pulse generating circuitry, is easily attached to the garment by some few manual steps by attaching the connection board to a connection unit which is integrated into the garment.

The garment is elastic and is intended to be tightly worn by the patient. The garment is ready for use in a user-friendly way for external electrical stimulation therapy of muscles. Electrodes, e.g. silicone-electrodes, are arranged at the inner surface of the garment, the surface facing the patient's skin and in contact to the patient's skin. The electrical connections connecting the electrodes to connection units are flexible and elastic.

The garment is made from materials chosen such that the garment may be washed in conventional laundry machines.

In particular the garment includes electrical connections adapted to connect the electrodes to one or several connection units, which do not influence the overall flexibility/elasticity of the garment. This is achieved, according to one embodiment, by integrating, e.g. by weaving silver threads into elastic bands or ribbons or into a piece of elastic.

In another embodiment an insulated conductor is integrated (e.g. weaved) into a piece of elastic.

The connection units are integrated into the garment, they have e.g. a flat extension, and they are flexible. Preferably, they are made from a rubber material and are provided with a magnetic material. In particular each connection element of the connection unit is provided with a magnet beneath the rubber material and arranged such that a connection pad may be attached at the upper surface and held in place by the magnet. The connection pad is naturally also provided with a magnetic material enabling the attachment.

The connection pads are arranged at a flexible flat board having the magnetic material arranged at predefined positions in order to exactly connect each of the connection pads to a mating connection element of the connection unit. The connection board and the connection unit are held together by the magnetic forces created by the magnetic material at the respective parts.

According to one embodiment both the connection unit(s) at the garment and the connection board(s) are made of a flexible material, which is an important aspect making the garment more comfortable to wear.

According to the invention the control unit is adapted to control connection of each of the electrodes to be in the state of acting as anode, cathode, or being disconnected.

By this arrangement it is e.g. possible to stimulate two muscles by three electrodes if the applied stimulation pulses are separated in time, i.e. one of the electrodes are used for both muscles. Thus, the control unit enables a very flexible control of the application of the stimulation pulses and by using short simulation pulse durations very complex stimulation programs may be used in that many muscles and muscle groups may be covered during the therapy.

The control unit preferably applies a so-called open-loop control, i.e. no feedback is used to control the applied current/voltage. The advantage of not using feedback is that in case an electrode temporarily loses contact to the skin, or the contact area between electrode surface and skin decreases, the current density of the remaining contact surface not should incur pain.

The amount of energy supplied to the patient via the electrodes is much lower than the energy levels used for by devices for pain relief. One risk, or drawback, with such devices is that the applied energy might stimulate the muscle to contract.

The level of the stimulation energy used in connection with the present invention is much lower than used for example in the device described in WO-03/006106.

In the present invention, a garment worn by the patient is provided. The garment has a first module electrically connected to a second module. The first module has a first sub-control unit electrically connected to a first electrode and a second electrode placed at a first muscle of the patient and a third electrode and a fourth electrode placed at a second muscle. The sub-control unit is electrically connected to a master unit. The first sub-control unit receives an instruction signal from the master unit. The first sub-control unit distributes stimulation signals to the first, second, third and fourth electrodes based on instructions in the instruction signal. The master unit sends a first stimulation signal to the first sub-control unit. The first sub-control unit stimulates the first muscle with the first stimulation signal without shortening the first muscle by sending the first stimulation signal to the first electrode placed at the first muscle. The stimulation of the first muscle relaxes the second muscle. A measuring unit (U1) of the master unit determines a first current value flowing from the first electrode through the first muscle to the second electrode and sends the first current value to a central processing unit (CPU) in the master unit or the first sub-control unit. The CPU compares the first current value to a current reference value and increases a voltage of the first stimulation signal when the first current value is below the current reference value.

In an alternative embodiment of the present invention, the CPU of the master unit or the first sub-control unit measures a voltage signal between the third electrode and the fourth electrode mounted on the second muscle.

In yet an alternative embodiment of the present invention, the CPU of the master unit sends a data unit with instructions to the first sub-control unit before sending a first stimulation pulse of the first stimulation signal to the first sub-control unit.

In another embodiment of the present invention, the measuring unit U1 determines the first current value by continuously measuring a voltage drop across a resistor R1 prior to a pulse creating switch SW1.

In yet another embodiment of the present invention, the CPU increases a voltage of the first stimulation signal when the first current value is below a start current value.

In an alternative embodiment of the present invention, the switch SW1 is opened when the first current value reaches a stop current value and the switch SW1 is closed when the first current value reaches a start current value that is lower than the stop current value.

In another embodiment of the present invention, a voltage of the stimulation signal is set by allowing the first current value fluctuate between the stop current value and the start current value.

In an alternative embodiment of the present invention, a polarity of the first electrode and the second electrode is switched.

In yet an alternative embodiment of the present invention, the first sub-control unit distributes the first stimulation signal to the first and second electrodes according to the instructions of the data pulse.

In another embodiment of the present invention, the master unit switches the first stimulation signal from being in a voltage mode that has a constant voltage to a current mode that has a substantially constant current wherein the current is only permitted to fluctuate between start current value and the stop current value.

In an alternative embodiment, the CPU changes the frequency and the pulse length of the first stimulation signal.

BRIEF DESCRIPTION OF THE DRAWINGS

FIGS. 11A-B are schematic views of a current signal when the arrangement shown in FIG. 10 is in the current mode according to the present invention;

FIGS. 11C-D are schematic views of a current signal when the arrangement shown in FIG. 10 is in the voltage mode according to the present invention;

FIG. 21 is a schematic view of an alternative embodiment of the body suit of the present invention;

FIG. 22A is a schematic illustration of a current in a muscle when the arrangement is in the voltage mode;

FIG. 22B is a schematic illustration of a voltage in a muscle when the arrangement is in the voltage mode;

FIG. 22C is a schematic illustration of 100 Ohm electrodes mounted on a muscle with an internal resistance of 6500 Ohm;

FIG. 22D is a schematic illustration of 1000 Ohm electrodes mounted on the muscle shown in FIG. 22C;

DETAILED DESCRIPTION OF PREFERRED EMBODIMENTS

The present invention will now be described with references to the appended drawings.

Figure 1:
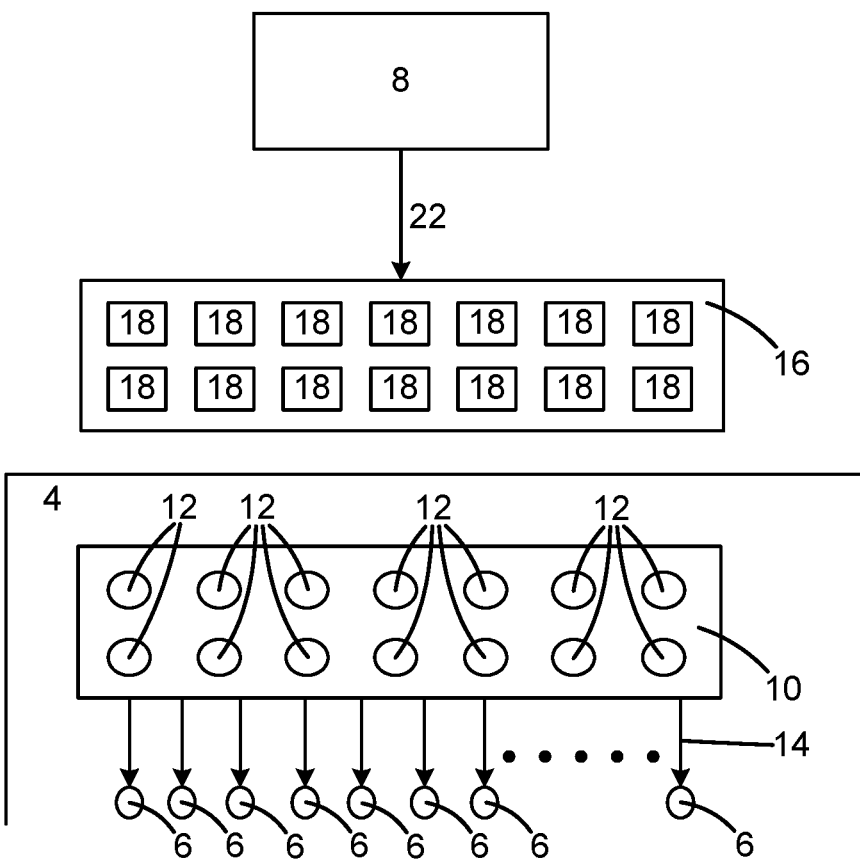
FIG. 1 is a schematic block diagram illustrating the medical therapy arrangement according to the present invention.

With references to FIG. 1, the present invention relates to a medical therapy arrangement 2, for applying electrical stimulation to a human or animal subject, comprising a garment 4 adapted to be tightly arranged at said subject, and provided with a plurality of electrodes 6 at the inner surface which are adapted to be in electrical contact to the skin of the subject.

The arrangement further comprises a control unit 8 which is adapted to provide each electrode 6 to work as one or many of anode, cathode or being disconnected, in accordance with a predetermined therapy stimulation program.

At least one connection unit 10 is provided which comprises a predetermined number of connection elements 12 being respectively electrically connected to the electrodes 6 via separate connection lines 14, which are flexible and elastic. And, at least one connection board 16 is provided which comprises a predetermined number of connection pads 18 being electrically connected to the control unit 8.

The connection unit 10 is an integrated part of the garment 4 and preferably arranged such that the connection elements 12 are accessible to establish electrical connections to the connection pads 18 of said connection board 16. In that regard the connection board 16 is detachably attachable to the connection unit 10 by a fastening means 20, such that the connection unit 10 and the connection board 16, when attached to each other, are positioned in relation to each other in order to electrically connect the connection pads 18 to mating connection elements 12.

Figure 2:
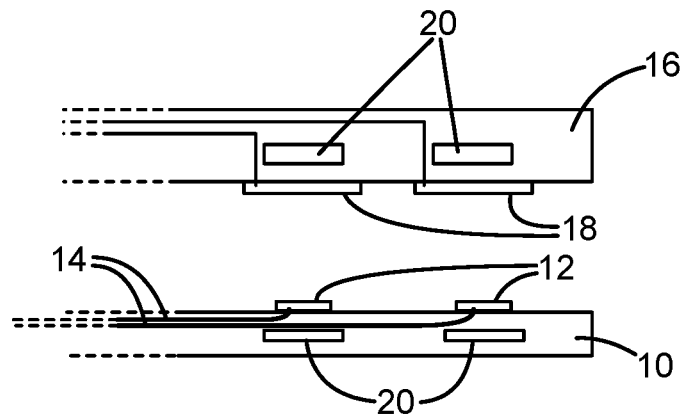
FIG. 2 is a schematic cross-sectional view of a part of the connector board and connector unit according to an embodiment of the present invention.

According to one embodiment the fastening means 20 is adapted to detachably attach the connection board 16 to the connection unit 10 by magnetic forces. FIG. 2 is a schematic cross-sectional view of a part of the connector board 16 and the connector unit 10. In the figure it is shown that the magnetic forces are created by magnetic material, in the figure indicated as separate magnets, arranged at predefined positions of the connection board 16 and the connection unit 10, respectively. In the figure the magnets are arranged behind each of the pads 18 and elements 12 in order to secure the electrical connection. As an alternative, the magnets may be arranged e.g. behind every second pad and element or at positions close to the pads and elements.

The positions of the magnets at the connection board 16 and at the connection unit 10 ensure that these are correctly positioned in relation to each other. In order to further improve the positioning, one or many protuberances and mating indentations (not shown in the figure) may be arranged at the connection board and connection unit, respectively.

As an alternative the fastening means 20 comprises mechanical means which is adapted to detachably attach the connection board to the connection unit. These mechanical means may e.g. comprise one or many Velcro straps arranged to provide for the necessary pressure between the connection board and connection unit in order to establish electrical connection between the pads and elements. The mechanical means may also be embodied by some kind of snap connection.

Preferably, the connection unit 10 has an essentially planar extension and is made from a flexible material, e.g. a flexible rubber material.

Also, in accordance with one embodiment, the connection board 16 has an essentially planar extension and is made from a flexible material, e.g. a flexible rubber material.

However, it is advantageous that, in particular the connection unit 10, is made from a flexible material, in order to make the garment comfortable to wear, but it is also possible, within the scope of the present invention, that the connection board 16 and/or the connection unit 10 is made from a rigid material. According to one embodiment the connection unit is made from a flexible material but the connection board is made from a more rigid material, e.g. from a suitable plastic material.

The connection board 16 and the connection unit 10 have essentially the same size.

In one exemplary embodiment the shape is approximately rectangular having a length in the interval of 8-12 cm, a width of 1.5-3 cm and a thickness of 0.25-1.5 cm.

Naturally, other sizes and shapes are possible, e.g. circular and elliptical, within the scope of the invention as defined by the appended claims.

The connection lines 14, that connect each electrode 6 to a respective connection element 12, are flexible and elastic such the wearer of the garment may move unimpededly.

According to one embodiment the connection line 14 is included into a piece of elastic into which an electrical conductor is integrated. This is achieved e.g. by weaving conducting threads, e.g. made from silver, into the piece of elastic.

As an alternative the connection line 14 is an insulated conductor being directly integrated, e.g. by weaving, into the material of the garment.

The control unit 8 is preferably a separate unit in relation to the connection board 16, and that the connection pads 18 are connected to the control unit 8 via an electrical cable 22. According to one embodiment the control unit 8 comprises a stimulation pulse generator, an energy source, a storage means, an input/output unit and a coupling unit. The energy source, typically being a battery, e.g. a rechargeable battery, is adapted to energize the circuitry of the control unit, e.g. the stimulation pulse generator. The predetermined therapy stimulation program is stored in the storage means and specific instructions related to the specific patient to be treated is input by the physician via the interface. The input/output unit may include one or many buttons and a display, e.g. a touchscreen.

The control unit is preferably attached to the garment wearer by some kind of strap in a position where it is easily accessed but not prevents movements.

In accordance with another embodiment the control unit instead is an integral part of the connection board, and then the connecting electrical cable is obviated.

The control unit is preferably adapted to apply an open-loop control when controlling the application of stimulation pulses. I.e. no feed-back is used which is advantageous in order to avoid that higher stimulation current is applied in the situation where an electrode loses, or has less, contact to the skin.

The garment is preferably made from a predetermined number of interconnectable parts. The reason is that the garment then is easier to put on. Each part is then provided with a connection unit that in turn is connected to the electrodes.

For some patients only a part of the body has to be subjected to stimulation, e.g. an arm or a leg. In that case a garment is used that is adapted to enclose that part. And, for other patients, the entire body has to be enclosed by the garment in order to gain full effect of the therapy.

An overall requirement of the garment is that it may be tightly arranged at the body to secure that the electrodes are in contact to the skin of the patient. The garment must be able to be washed in a normal laundry machine. Preferably the garment comprises a synthetic fiber made from a polyurethane-polyurea copolymer, e.g. spandex or elastane.

According to an embodiment, the garment comprises five major textile and support materials. Elastic spandex for areas covering muscles and, embedded in this spandex, muscle electrodes for skin contact; firm elastic spandex textile in joint areas to induce joint stability and specific skin contact of embedded muscle and vibration (if included) electrodes; and Velcro to interlock the garment parts and also induce joint stability and electrode skin contact. Zippers are placed in the different garment parts to enable simple dressing and use of the garment. Padding and other supportive materials are placed between the textile layers to enhance stability and electrode skin contact.

In order to provide for a perfect garment fit for each patient, each garment may be tailor made for each patient. Hence, each patient may be individually measured. Based on the calibration made by the specialist, the therapist chooses which muscles to stimulate and therefore induce muscle relaxation of corresponding spastic muscles. The tailor-made garment is produced and the control unit is programmed with the necessary parameters such as to perform a vibrator (if included) and EMS stimulation in the prescribed manner.

The electrodes are arranged at the inner surface of the garment and must therefore be flexible to adapt to the skin surface. According to one embodiment the electrodes are, for example, silicone-electrodes or any other conductive electrode materials. The number of electrodes is naturally dependent upon the therapy to be applied, but preferably at least ten electrodes are included, often much more.

According to another embodiment the control unit comprises a sensing unit adapted to receive electrical signals, e.g. EMG-signals, sensed by one or many of said electrodes. The received signals may then be analyzed and used to improve the therapy. According to one aspect the sensed electrical signals are used to decide which therapy to be used and then apply that therapy in accordance with an open-loop controlled stimulation therapy. According to another aspect, it would also be possible to apply the arrangement in a closed-loop controlled simulation therapy where the applied stimulation energy is adapted in dependence of sensed electrical signals.

Figure 3:
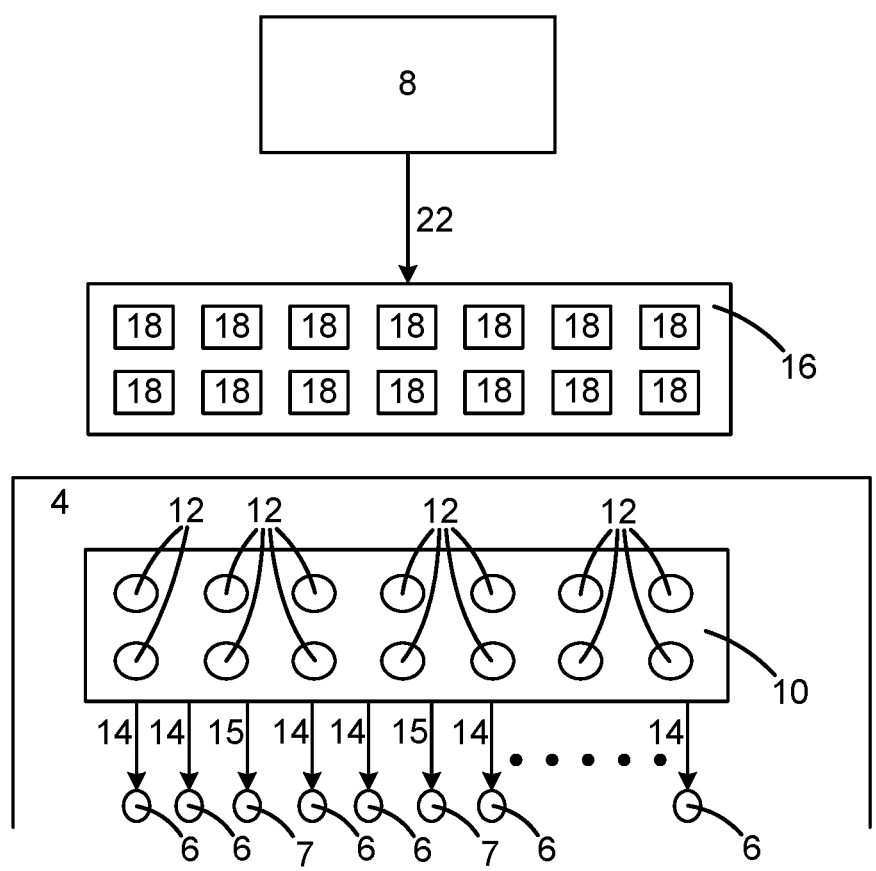
FIG. 3 is a schematic block diagram illustrating another embodiment of the medical therapy arrangement according to the present invention.

In a further embodiment the arrangement also provides for combined electrical and vibration therapy. This embodiment is schematically illustrated in FIG. 3. The same references used in FIGS. 1 and 2 apply here as well. To use a combined electrical and vibration therapy has proven an advantageous therapy and in accordance to this embodiment a plurality of vibration units 7 are arranged at the garment, e.g. at the inner surface of the garment, and wherein each vibration unit being connected to the connection unit via a flexible and elastic vibration unit connection line 15. The vibration units may also be arranged at the outer surface of the garment and apply the vibrations through the garment material.

Different types of vibration units may be used, e.g. based upon piezo-technology, a so-called DC-motor, or a solenoid-based unit.

Preferably the relation between the number of electrical stimulation electrodes and vibration units is 2:1. However, even fewer vibration units may be used.

Figure 4:
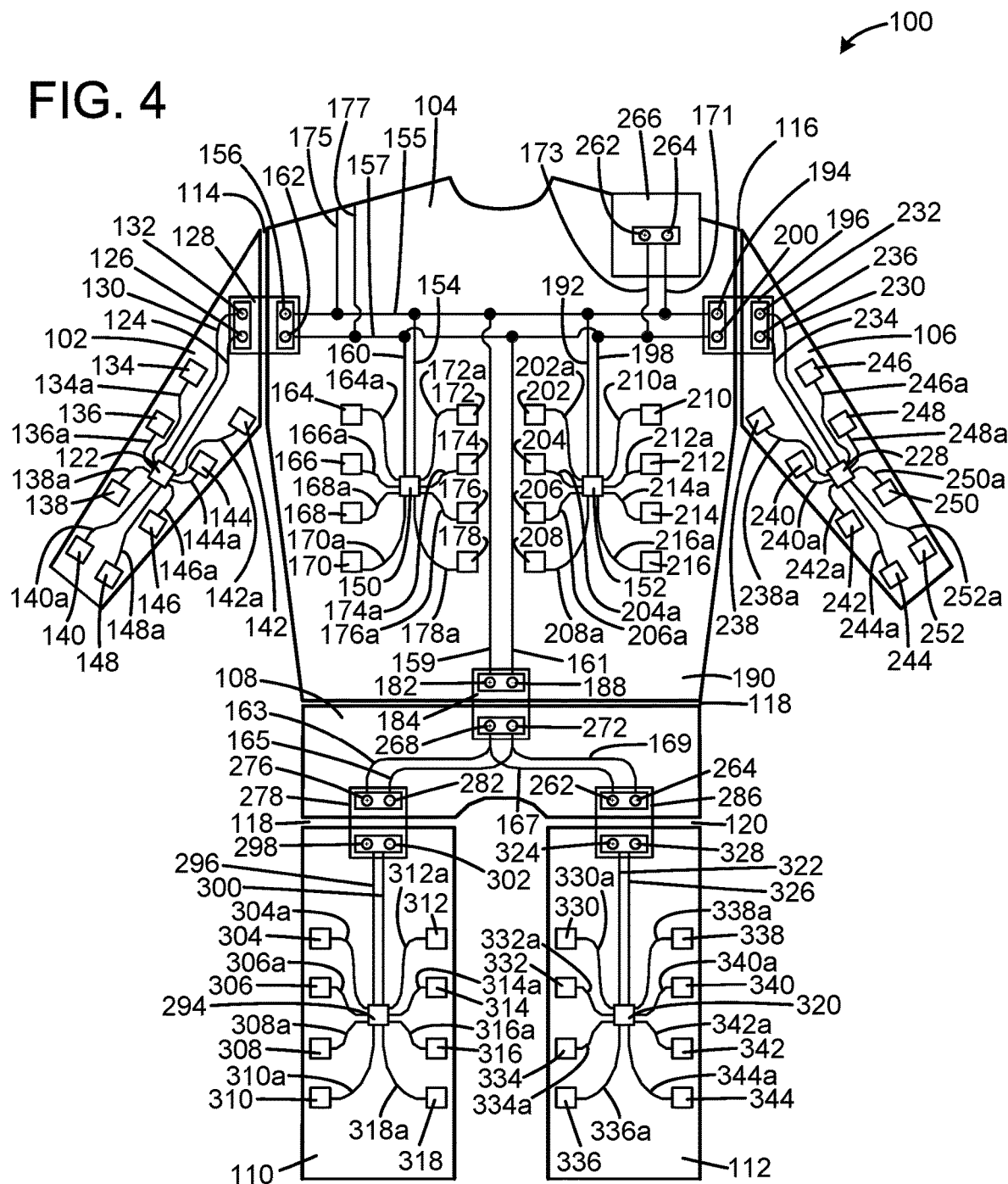
FIG. 4 is a schematic front view of the body suit or garment according to the present invention.

FIG. 4 is a schematic view of a frontside of a garment of an elastic and tight body suit 100 of the present invention. The body suit 100 has a backside that is substantially similar to the frontside. The backside of the body suit could be designed with wires, electrodes, sub-control units in a way that is identical or similar to the frontside. The body suit 100 has a plurality of sub-control units integrated into the fabric that are electrically connected to a plurality of electrodes that are located on an inside of the fabric so that the electrodes are facing and urged towards the skin of the person wearing the body suit 100. The sub-control units make it possible to substantially increase the number of electrodes in the body suit 100 and to carry out more advanced treatments of the patient wearing the body suit.

An important feature of the present invention is that the electrodes not only activate the muscles but also the afferent (sensory) nerves in the muscles that conduct sensory signals from muscle and skin sensors to the spinal cord and act as input to the interneuron networks that are responsible for controlling the movement of body parts such as an arm or a leg. This happens when the afferent nerves are stimulated at about 20 Hz and at a low enough voltage so that the agonist muscle does not contract to cause movement. Upon receipt of the sensory signals from the afferent nerves, the spinal cord sends a signal to the agonist muscle to relax the muscle. It is important that the frequency range of the stimulation signal can be changed to optimize the afferent input to the interneuron networks. It is to be understood that any reference to the stimulation of muscles includes the stimulation of nerves in the muscles and other nerves adjacent to the electrodes.

The body suit 100 is used to stimulate and relax muscles and nerves, of the person wearing the body suit, with electrical pulse current flowing between electrodes mounted in the fabric of the body suit 100 and through the muscles on which the electrodes are positioned. When the body suit has a large number of electrodes but no sub-control units, this creates a problem because all the electrodes must be connected to the controller or master unit that transmits the pulses and current and other information via wires to the electrodes. The large number of wires required integrated in the suit makes the body suit prone to faulty connections over time as the body suit is worn by the person and is taken on and off. One solution to this problem is to use sub-control units to reduce the number of wires in the body suit and the required lengths of the wires going to the electrodes i.e. the wire lengths are also reduced. The body suit can include modules wherein the sub-control units in each module are distributing the stimulation pulses that arrive from the master unit.

The sub-control units are controlled by the master unit. Preferably, but not necessarily, each sub-control unit is electrically connected to the master unit via only a few wires such as two wires that provide the power voltage and pulse signals going to the sub-control units. The pair of wires can also carry data instructions to the sub-control units. It is also possible to send the data instructions by wireless communication between the master unit and the sub-control units.

As described in detail below, one important advantage of using the sub-control units is that a higher frequency and more electrodes can be used in the body suit. In general, the sub-control units receive pulsating stimulation signals from a programmable master control unit that the sub-control units distribute to pre-determined electrodes to stimulate and/or relax muscles and muscle pairs located below the electrodes. It is also possible to stimulate nerves similar to stimulating muscles. Muscles are merely used as an illustrative example but the stimulation also applies to nerves in the same way. The master control unit is detachably and electrically connected to the body suit at connectors that are located on an outside of the body suit 100. The master control unit also has a power source to power the sub-control units located in the modules of the body suit. The modules are electrically connected to one another via connectors that are electrically connected to the sub-control units. An important feature is that the master control unit may be detached from a first connector on the body suit and re-connected to a second connector on the same body suit so that the master control unit or master unit can be moved between various connectors of the body suit. Each connector has a positive and negative pole on a first side and a corresponding positive and negative pole on the second opposite side of the connector. The positive pole on the first side is electrically connected to the positive pole on the second side and the negative pole on the first side is electrically connected to the negative pole on the second side so that each connector acts as a "bridge" to carry power, data and pulses from one module to the adjacent module. A stimulation program runs in the master control unit, that includes instructions that are sent to the sub-control units through a serial data bus.

The garment or body suit 100 is preferably made of a flexible and elastic fabric material that tightly fits the body of the patient to be treated. It is to be understood that the body suit 100 is schematically shown to illustrate the principles of the present invention and that the exact location of the various components can change or be customized to the specific needs of the patient to be treated. If the body suit 100 should include a large number of electrodes without the use of sub-control units, this would require large numbers of wires that extend from the master unit to all the electrodes. The large number of wires required sometimes makes it unpractical to fit them all in the fabric of the body suit and the frequency range must be reduced to low frequencies, as explained in detail below. An important feature of the present invention is the idea of moving some of the intelligence to the sub-control units that are located in the body suit modules in order to reduce the required wiring and improve the functionality of the body suit 100 and to allow higher stimulation frequencies.

More particularly, the body suit 100 may include detachably and independently functioning modules such as a right arm module 102, an upper body module 104, a left arm module 106, a pelvis module 108, a right leg module 110 and a left leg module 112. The modules are preferably attached to one another by a suitable fastening mechanism 114, 116, 118, 120 such as zippers, Velcro or any other suitable mechanism that can easily be attached and detached. One advantage of using modules is that the patient may need different sizes on different parts of the body. In some instances, the patient may not need all the modules because certain parts of the body are healthy and do not need to be treated. In general, the paralyzed body portions are smaller in size than the non-paralyzed body portions so that different sizes may be needed. Similarly, a body part, such as an arm, that is spastic is generally smaller than a non-spastic body part. The number of electrodes and sub-control units in each module may vary and the body suit 100 should merely be treated as an illustrative example.

The right arm module 102 has a first sub-control unit 122 electrically connected via a flexible and elastic wire 124 to a negative pole 126 of a first connector 128 and via a flexible and elastic wire 130 to a positive pole 132 of the first connector 128. One important function of first connector 128 is to provide a "bridge" from the right arm module 102 to the upper body module 104 so that they are electrically connected. This function applies to all the other connectors of the body suit 100. The connectors may be made of a flexible fabric that includes conductive wires to electrically connect the positive pole on one module with the positive pole on the adjacent module and to electrically connect the negative pole on one module with the negative pole on the adjacent module. The sub-control unit 122 is electrically connected to electrodes 134, 136, 138, 140, 142, 144, 146 and 148 via flexible and elastic wires 134a, 136a, 138a, 140a, 142a, 144a, 146a and 148a, respectively. The right arm module 102 is electrically connected to all the other modules of the body suit 100 via the connectors that extend between the modules and connect one module to an adjacent module.

The upper front body module 104, preferably, has two sub-control units i.e. a second sub-control unit 150 and a third sub-control unit 152. The module 104 may have more or fewer sub-control units and the use of two modules is merely an illustrative example. The sub-control unit 150 is electrically connected via a flexible and elastic wire 154 to a flexible and elastic wire 155 that is connected to a positive pole 156 of the first connector 128 and via a flexible and elastic wire 160 to a flexible and elastic wire 157 that is electrically connected to a negative pole 162 of the first connector 128. The wire 155 is also electrically connected to a positive pole 194 of a connector 196 that is connected to the left arm module 106 and the wire 157 is electrically connected to a negative pole 200 of the connector 196. A flexible and elastic wire 175 is electrically connected to wire 155 and leads to the backside of the body suit 100 that is identical or similar to the front side shown in FIG. 4. Another flexible and elastic wire 177 is electrically connected to wire 157 and extends to the backside of the body suit 100 so that the wires 175, 177 provide the power, pulses and possibly data to the backside of the body suit in the same way as to the front side of the body suit. The sub-control unit 150 is electrically connected to electrodes 164, 166, 168, 170, 172, 174, 176 and 178 via flexible and elastic wires 164a, 166a, 168a, 170a, 172a, 174a, 176a and 178a, respectively. The body module 104 is electrically connected to all the other modules of the body suit 100 via the connectors that extend between the modules and connect one module to an adjacent module.

Similar to sub-control unit 150, sub-control unit 152 is electrically connected via a flexible and elastic wire 192 to wire 155 that is electrically connected to the positive pole 194 of a second connector 196 and via a flexible and elastic wire 198 to wire 157 that is electrically connected to the negative pole 200 of the third connector 196. The sub-control unit 152 is electrically connected to electrodes 202, 204, 206, 208, 210, 212, 214 and 216 via flexible and elastic wires 202a, 204a, 206a, 208a, 210a, 212a, 214a and 216a, respectively.

Similar to the right arm module 102, the left arm module 106 has a fourth sub-control unit 228 electrically connected via a flexible and elastic wire 230 to a positive pole 232 of the second connector 196 and via a flexible and elastic wire 234 to a negative pole 236 of the third connector 196. The sub-control unit 228 is electrically connected to electrodes 238, 240, 242, 244, 246, 248, 250 and 252 via flexible and elastic wires 238a, 240a, 242a, 244a, 246a, 248a, 250a and 252a, respectively.

The pelvis module 108 is located below the upper body module 104 but above the leg modules 110, 112. The pelvis module 108 is shown without sub-control units but the module 108 may also be provided with sub-control units similar to the other modules. The module 108 has an upper connector 184 that electrically connects the pelvis module 108 to the upper body module 104. The upper connector 184 has a positive pole 268 and a negative pole 272 on the pelvis module 108 and a positive pole 182 and a negative pole 188 at the bottom end of the body module 104. The positive pole 268 is electrically connected to the positive pole 182 and the negative pole 272 is electrically connected to the negative pole 188. The positive pole 182 is electrically connected to wire 155 via flexible and elastic wire 159 and the negative pole 188 is electrically connected to wire 157 via flexible and elastic wire 161. The positive pole 268 is electrically connected to the positive pole 276 of a third connector 278 via a flexible and elastic wire 163. The negative pole 272 is electrically connected to the negative pole 282 of connector 278 via a flexible and elastic wire 165. The positive pole 268 is also electrically connected to the positive pole 262 of a fifth connector 286 via a flexible and elastic wire 167. The negative pole 272 is electrically connected to the negative pole 264 of the fifth connector 286 via a flexible and elastic wire 169. All the connectors 128, 184, 196, 278 and 286 include elastic wiring to electrically connect one module with another module.

The right leg module 110 has a fifth sub-control unit 294 electrically connected via flexible and elastic wire 296 to a positive pole 298 of the fourth connector 278 and via a flexible and elastic wire 300 to a negative pole 302 of the fourth connector 278. The positive pole 298 is electrically connected to the positive pole 276 and the negative pole 302 is electrically connected to the negative pole 282. The sub-control unit 294 is electrically connected to electrodes 304, 306, 308, 310, 312, 314, 316 and 318 via flexible and elastic wires 304a, 306a, 308a, 310a, 312a, 314a, 316a and 318a, respectively.

The left leg module 112 has a sixth sub-control unit 320 electrically connected via a flexible and elastic wire 322 to a positive pole 324 of the fifth connector 286 and via a flexible and elastic wire 326 to a negative pole 328 of the fifth connector 286. The sub-control unit 320 is electrically connected to electrodes 330, 332, 334, 336, 338, 340, 342 and 344 via flexible and elastic wires 330a, 332a, 334a, 336a, 338a, 340a, 342a and 344a, respectively.

The master unit 266 is connectable to the body suit in many places. FIG. 4 shows the positive pole 264 of the master unit 266 electrically connected to the wire 155 via flexible and elastic wire 171 and the negative pole 262 electrically connected to wire 157 via flexible and elastic wire 173. If one of the modules is not necessary such as the right arm module 102, it is possible to connect the master unit 266 to the first connector 128 or to any of the other connectors. It is an important feature to be able to connect the master unit at a place that is convenient to the patient in case the patient has a handicap that makes it, for example, difficult to attach the master unit at the hip or if it is more convenient to attach the master unit at the upper shoulder when the patient is in a sleeping position. It is also possible to place several connectors in different places in the bodysuit so that the master unit can be placed there. Preferably, the master unit should be attached to any of the available connectors on the body suit 100. It is thus not necessary to have a separate connection that is only located in one place such as by the hip. It is thus possible to have several different connection points or connectors for the master unit.

Figure 5:
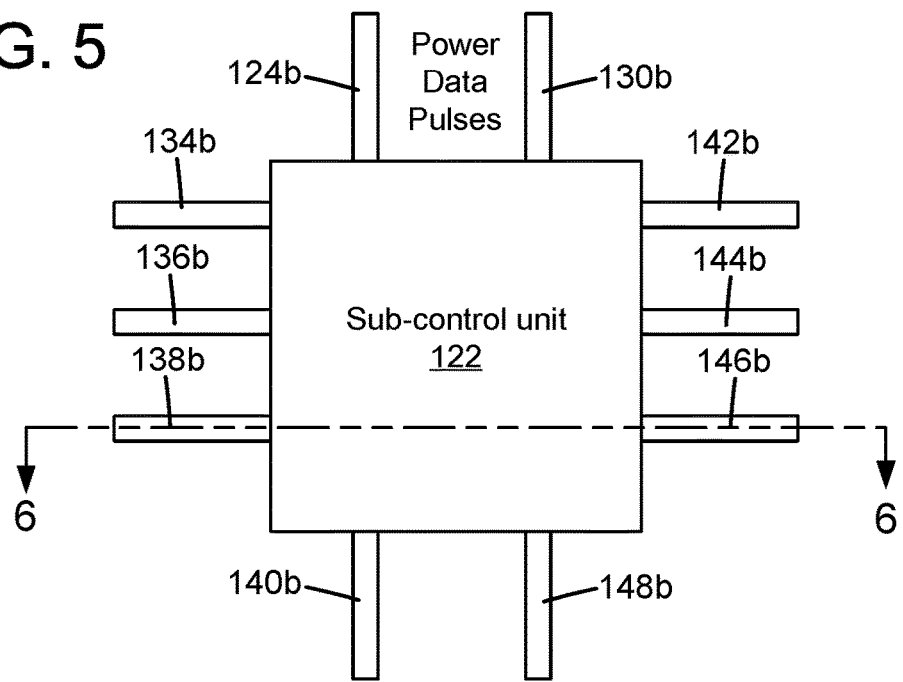
FIG. 5 is a schematic top view of a sub-control unit according to the present invention.

FIG. 5 is a schematic detailed top-view of sub-control unit 122. Preferably, all the sub-control units in the garment or body suit 100 are substantially similar to unit 122 serves as an illustrative example that applies to all the sub-control units. Preferably, the unit 122 is molded in a water-resistant material to make it water resistant so that the body suit can be machine washed without damaging the electronics in the unit. The unit 122 may have eight extensions wires that extend outwardly from the molding i.e. extensions 134b, 136b, 138b, 140b, 142b, 144b, 146b and 148b that are electrically connected to 134a, 136a, 138a, 140a, 142a, 144a, 146a and 148a (best shown in FIG. 4), respectively. This corresponds to 4 pairs of electrodes per sub-control unit. The unit 122 may have more or fewer extensions than eight. Sub-control unit 122 also has extensions 124b and 130b that are electrically connected to the wires 128 and 130, respectively, that extend to the connector 128 (best shown in FIG. 4). Power, data and stimulation pulses may enter the sub-control unit 122 via extensions 124b, 130b from the master unit 266. It is also possible to have more connections and send additional information in addition to the power, data and pulse information shown in FIG. 5. Any suitable serial communication technology may also be used and more than two wires/connectors can be used that are serially connected. It is to be understood that it is possible to combine electrodes in different ways to obtain more than four combinations.

When a frequency of 200 Hz is used for the stimulation signals/pulses, there is a total time period of 5 milliseconds available to send out all the combinations that the sub-control units handle. If, for example, 8 combinations are used then there are 5 milliseconds divided by 8 i.e. 625 microseconds between the start of each pulse. If the pulse length is 175 microseconds then there are 625 microseconds minus 175 microseconds=450 microseconds time gap between the pulses i.e. when there is no pulse signal before the next pulse starts. In other words, if, for example, 8 combinations are obtained and the pulse length is 175 microseconds and the frequency is 200 Hz then the time gap between the pulses is 450 microseconds. The time gap can be used to do other things such as measuring feedback signals from an antagonistic muscle, as described in detail below in connection with FIG. 9 or to send data as described in FIGS. 14 and 16. It is to be understood that the frequencies can be increased to a frequency higher than 200 Hz as long as there is a time gap between each pulse.

Figure 6:
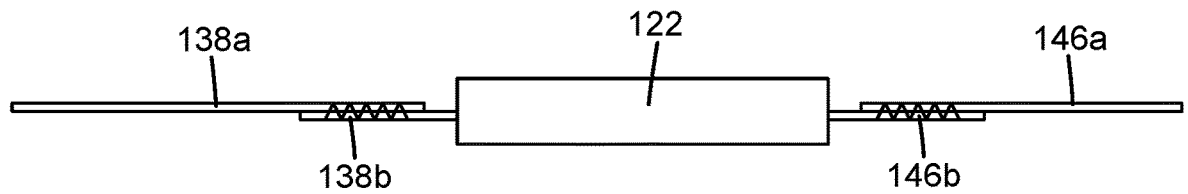
FIG. 6 is a cross-sectional side view of the sub-control unit shown in FIG. 5.

FIG. 6 is a schematic detailed side view of sub-control unit 122 that is connected to flexible wires 138a, 146a via sewable flexible conductive connections or extensions 138b, 146b that come out from the molded sub-control unit, respectively, by overlapping the wires from the garment to the connectors from the sub-control and then sew them together so that they are electrically connected. This principle or another connection method may be used on all the wires and extensions on all the sub-control units.

As a safety precaution, it is preferred that only the master unit sends out the stimulation pulses via the sub-control units to prevent the sub-control units from sending out unintended pulses that could be very uncomfortable or even dangerous to the patient wearing the body suit 100. The sub-control units thus merely direct or distribute the pulses to the correct pair of electrodes. The stimulation pulse, pulse length (duty cycle) and voltage/current etc. are controlled by the (central processing unit) CPU of the master unit by serial data communication with all the sub-control units before the pulses are sent out from the master unit.

As described in more detail below, the sub-control units may have information about the desired pulse length so that the correct pulse length is sent out to the electrodes. The longer the pulse length the more powerful the stimulation is. The pulse length may be set by the therapist of the body suit or be set by the master unit. In general, the pulses from the master unit have a pulse length that is slightly longer than the longest pulse length of the stimulation pulse distributed by the sub-control units. When the pulse length from the master unit is longer than the predetermined pulse out time period then the sub-control unit can control or reduce the length off the pulse to the electrodes. The master unit also has a safety mechanism for turning off any pulse that is longer than a predetermined time period as programmed in the master unit. In the preferred embodiment, these safety mechanisms are not controlled by the CPU but by circuits in the hardware that are separate from the CPU and the software for higher safety.

More particularly and as indicated above, two of the connectors 124b and 130b of all the sub-control units in the suit may be connectable via electrically conductive flexible and elastic wires to the master unit for carrying power, data and stimulation pulses. The data in a serial data-bus (between the master unit and the sub-control units) may include instructions to the sub-control units about which electrodes should be activated and in which order and combination should be used. The arrival of the stimulation pulses from the master unit to the sub-control units indicate when the electrodes, that are connected to the sub-control unit, should be activated and the sub-control units guide or distribute the stimulation pulses to the correct electrodes. The master unit may have a micro-controller (CPU) and the sub-control units may each also have a micro-controller (CPU) so that the units can communicate with one another. Preferably, the sub-control units should be able to save instructions from master unit and also values from the measured muscles so that these values can be sent back to the master unit that also saves the values and so that the master unit can decide whether the parameters should be changed or not (such as increasing/decreasing the voltage, current or changing the length of the pulse duty cycle and changing frequency or whether a different simulation program should be used. For example, the instructions from the master unit to a particular sub-control unit may require that the sub-control unit sends the first pulse to a first pair of electrodes and the second pulse to a different pair of electrodes etc. It is also possible to run a current from an electrode of a first sub-control unit to another electrode of a second sub-control unit.

After a certain number of stimulation pulses have been sent to the sub-control unit, it may be necessary to send different or the same instructions to the sub-control unit before additional pulses are sent from the master unit to make sure the sub-control units are properly synchronized and to ensure that the pulses are sent to the correct electrodes. This synchronization may be done by sending short synchronized instructions via the serial data-bus. In some instances, it may be necessary to turn off the data flow to the sub-control unit before the stimulation pulse is sent. It should be understood that the stimulation pulses and data are not transmitted simultaneously when a two-wired bus is used. The sub-control unit may require to be powered at 3V3 volt (3.3V) or 5V. Other voltage levels may be used but the lower the voltage of the power the more sensitive the system becomes to interferences.

The stimulation pulses may be generated by using a voltage ranging from 5-100V, more preferably a range of 15-80V is used. Most preferably, 20V or 40V is used. As explained in detail below, the voltage may be increased or decreased during the stimulation. As a safety precaution, it is desirable that only the master unit sends out the stimulation pulses and that the sub-control unit should not be able to generate such a strong pulse signal by itself in case the sub-control unit malfunctions and sends out a high voltage signal that is too long which is very uncomfortable to the patient wearing the body suit. Additionally, the master unit may instruct the sub-control units to activate their outputs in a way so that the outputs send out the stimulation pulses one at a time or a couple pulses at a time. If, for example, the sub-control units receive instructions from 1 to 5 so that when the first stimulation pulse arrives the sub-control unit 1 sends out the first pulse to the first electrode pair and when the second pulse arrives, sub-control unit 2 sends out the second pulse to the second electrode pair and so on until when the fifth pulse arrives, sub-control unit 5 sends out the fifth pulse. The process then restarts so that when the sixth pulse arrives to sub-control unit 1, the sub-control unit 1 sends out the first pulse to first electrode pair and when the seventh pulse arrives, sub-control unit 2 sends out the second pulse to second electrode pair and so on until the tenth pulse arrives and so on. In other words, if one sub-control unit has received instructions to activate 5 pairs of electrodes it starts with the first electrode pair again when the sixth pulse arrives to the sub-control unit. When the master unit re-synchronizes the sub-control units, the sub-control unit can start sending the stimulation pulses to the first electrode pair again. For example, if the master unit is connected to four sub-control unit and each sub-control unit is connected to four pairs of electrodes then sub-control unit 1 may send out the stimulation pulses when pulses 1 to 4 arrive and sub-control unit 2 sends out the stimulation pulses to its electrodes when pulses 5 to 8 arrive. Sub-control unit 3 sends out the stimulation pulses to its electrodes when pulses 9 to 12 arrive and sub-control unit 4 sends out the stimulation pulses to its electrodes when pulses 13 to 16 arrive. This procedure then restarts and repeats the same order with sub-control unit 1 to sub-control unit 4 for pulses 17-32 and so on until the master unit changes the synchronization of the sub-control units. Preferably, all the sub-control units have a unique address so that the master unit can send information/data to a specific sub-control unit. It is also possible to set all the sub-control units so that they all send out the pulses simultaneously so when pulse 1 arrives all the sub-control units simultaneously send this pulse to its electrodes and when pulse 2 arrives all the sub-control units simultaneously send out pulse 2 to its electrodes. If the sub-control units have a different number of electrodes connected thereto then the sub-control unit that has the highest number of electrodes connected thereto determines when pulse 1 arrives again over sub-control units that have a lower number of electrodes connected thereto. Information about the maximum number of electrodes and stimulations for the sub-control unit that is connected to the highest number of electrodes is sent to all the other sub-control units. For example, if one sub-control unit has six different stimulations to carry out and another sub-control unit only has three stimulations to carry out, the second control unit counts the number of pulses that have arrived so that when the first three pulses arrive it sends them out at the same time as the first sub-control unit sends out the first three of the six stimulations. When the second sub-control unit has sent three stimulation pulses it stops and waits for pulse 7 to arrive to start sending out another three stimulation pulses. The first sub-control pulse sends out one stimulation pulse for each pulse that arrives and restarts when pulse 7 arrives so that pulse 7 is sent to the same electrode pair as pulse 1.

The sub-control units may be designed so that they do not permit a stimulation pulse that is longer than a certain threshold value such as 200 microseconds or any other suitable pulse length to pass through to the electrodes. Similarly, the master unit may also be designed so that it cannot send out stimulation pulses that are longer than another threshold value such as 250 microseconds. If the processor of the master control unit 266 tries to send out a stimulation pulse that is longer than the threshold value then the safety circuit of the hardware terminates the stimulation pulse as a safety precaution. The threshold values can be adjusted so that longer and shorter duty cycles can be used. Preferably, the stimulation pulse from the master control unit 266 to the sub-control unit 122 should be slightly longer (such as a few microseconds and up to 30 microseconds) than the maximum pulse length that is distributed from the sub-control unit to the electrodes so that there is time for the voltage to be received by the CPU of the sub-control unit and to the output circuit to power up the output circuit on the sub-control unit before the stimulation pulse is distributed to the electrodes. The sub-control units may be designed to delay sending the stimulation pulses to the electrodes with, for example, 10 microseconds to ensure there is sufficient time for the circuitry on the sub-control units to handle the incoming stimulation pulses from the master unit. It may also be possible to connect the sub-control units to the master unit via blue-tooth, wi-fi, one-wire data bus or any other suitable wireless or on wire data technology in order to send data to and from the sub-control units to the master unit.

Figure 7:
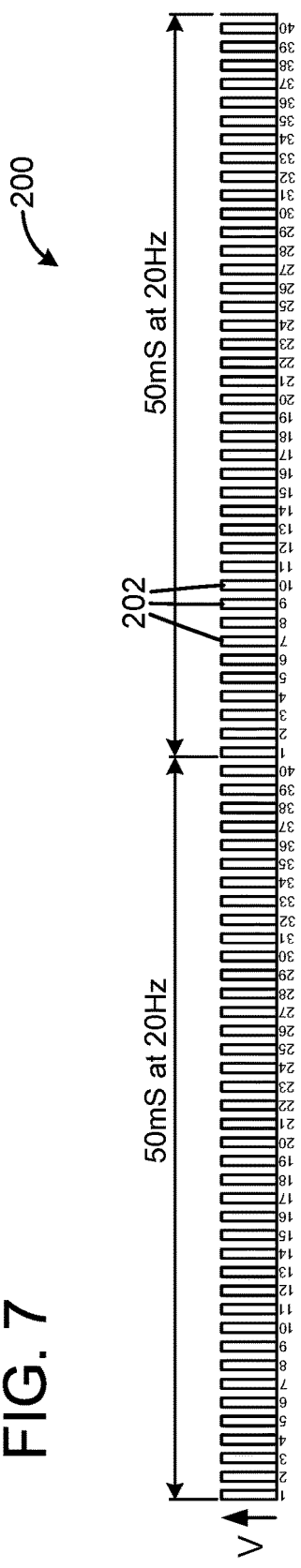
FIG. 7 is a schematic view of a stimulation pulse signal at 20 Hz.
Figure 8:
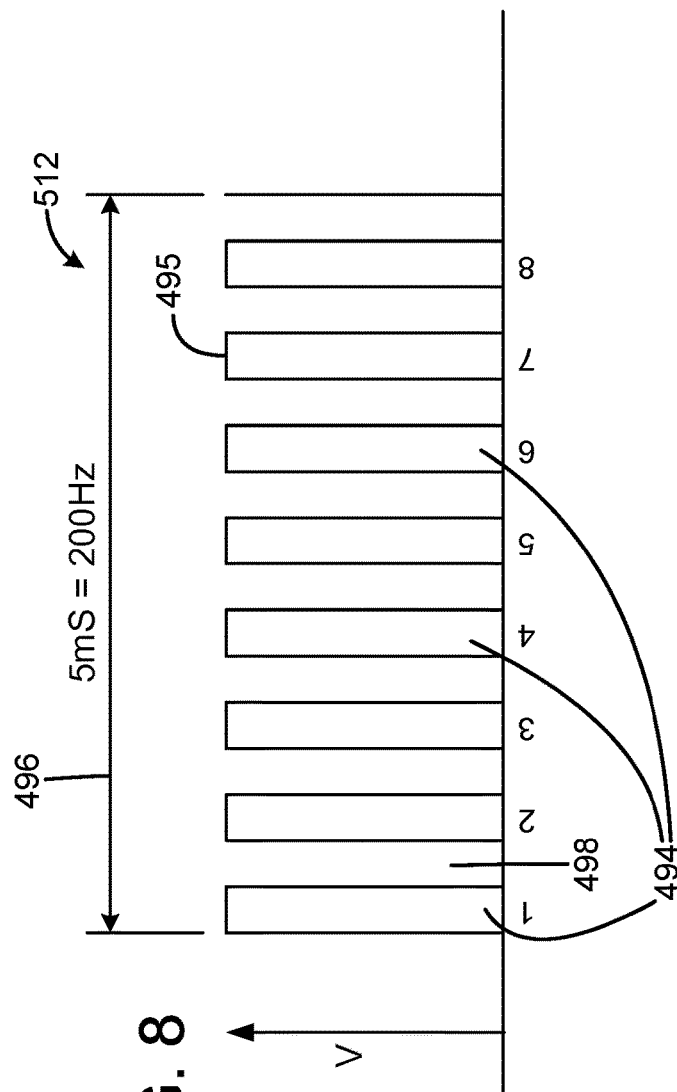
FIG. 8 is a schematic view of a stimulation pulse signal at 200 Hz.

FIG. 7 is a schematic view 200 of the stimulation pulses 202 that are sent to electrodes in the garment. More particularly, FIG. 7 illustrates an example of when 40 stimulation pulses are sent at 20 Hz and the pulse period is 50 milliseconds long in a system that handles all 40 electrodes from one unit. As explained in detail below, when a frequency of 200 Hz is used it is not possible to fit in 40 stimulation pulses (with a duty cycle of 175 microseconds) during the pulse period of 5 milliseconds. By using sub-control units, it is possible to increase the frequency because there are fewer stimulation pulses per sub-control unit, as shown in FIG. 8. At a frequency of 20 Hz, the time period for one cycle is 50 milliseconds (or 0.05 seconds). FIG. 7 shows 40 pulses or stimulation combinations wherein each pulse has a duty cycle (pulse length) of about 175 microseconds. Each stimulation pulse activates a pair of electrodes. It should be understood that the duty cycle can be shorter or longer than 175 microseconds. After 50 mS at 20 Hz a new frequency cycle is started. The treatment of a patient wearing the body suit 100 may typically last for an hour or so but shorter and longer treatment periods may also be used. Frequency of 20 Hz is suitable to stimulate an agonist muscle in order to relax an antagonist muscle but higher and lower frequencies of the pulse signal may also be used. An important advantage is that after the treatment has stopped, the antagonist muscle remains relaxed for many hours and in some cases for days.

It is desirable to have the ability to change the frequency range so that the frequency used can be customized to the required treatment of the patient. Preferably, it should be possible to change the frequency range between 1 Hz-200 Hz. It should also be possible to vary the voltage used i.e. to change the amplitude of the pulses. One problem is that if 40 stimulation pulses are desired at 200 Hz, only a time period of 5 mS is available (when one frequency cycle at 200 Hz) and if the pulse length is 175 microseconds then the total pulse length for 40 pulses is 7 mS (40×175 microseconds) without the time gap between pulses which exceeds the time period available (5 mS) for one frequency cycle so it is not possible to run the system at 200 Hz.

FIG. 8 is a schematic view of a stimulation signal 512 with stimulation pulses 494 at a 200 Hz frequency at one frequency cycle 496 of 5 mS so that there is a time gap 498 between each stimulation pulse 494. Higher or lower frequencies of stimulation signal 512 may also be used and 200 Hz is merely an illustrative example. Each stimulation pulse 494 has a pulse length or duty cycle 495. This means there is enough time to send out about 20 stimulation pulses as a maximum of combinations when the frequency is 200 Hz and the pulse length or duty cycle 495 is 175 microseconds for each pulse. It is necessary to have a time gap between the outgoing pulses. If 5 milliseconds are divided into 20 pulses, 250 microseconds are available for each stimulation pulse and if the pulse length is 175 microseconds then there is a time gap of 75 microseconds between each stimulation pulse. As indicated above, this can be solved by using sub-control units in each module, as shown in FIG. 4. When sub-control units are used in the body suit each sub-control unit may, for example, be connected to 8 electrodes. This means that a higher frequency than 20 Hz may be used and that it is possible to carry out more than 8 stimulation combinations per sub-control unit. In other words, it is not necessary to limit the use to certain pre-set pairs of electrodes but use different combinations of electrodes that are stimulated. For example, it may be possible to send stimulating pulses to electrodes that are located on the same side of an arm but at a distance from one another. It is also possible to send stimulating pulses to electrodes that are located on opposite sides of the arm such as one electrode at the front of the arm and another electrode located at the backside of the arm. It is also possible to combine the sub-control units so that, for example, a sub-control unit (such as unit 150) in the upper body module distributes a stimulation pulse to a positive electrode (such as electrode 174) in that module while another sub-control unit (such as unit 152) in the upper body module negatively activates an electrode (such as electrode 204) in the upper body module so that are current goes from the positive electrode of one sub-control unit to the negative electrode of another sub-control unit When, for example, four electrodes are used, it is possible to stimulate the electrodes in more than two ways when each pulse corresponds to or activates a pair of electrodes. By using sub-control units, the available time period available (5 ms) at 200 Hz is enough time to stimulate 8 electrodes because when the duty cycle for each pulse is 175 microseconds. It is possible to generate at least 25 different pulses to electrodes or fewer during this time period which is more than sufficient to stimulate different combinations of 4 pairs of electrodes. In practice, fewer than 25 pulses can be generated because it is important to have a time gap between each pulse in case, for example, there may be a need to take measurements on the antagonist muscles between the pulses or to communicate with the master unit during the time gap between the stimulation pulses. It is undesirable to take measurements during the duty cycle of a stimulation pulse because the stimulation pulse to a certain muscle and/or nerve (agonist) is likely going to interfere with the measurements of the voltage signals at another adjacent muscle (antagonist).

Figure 9:
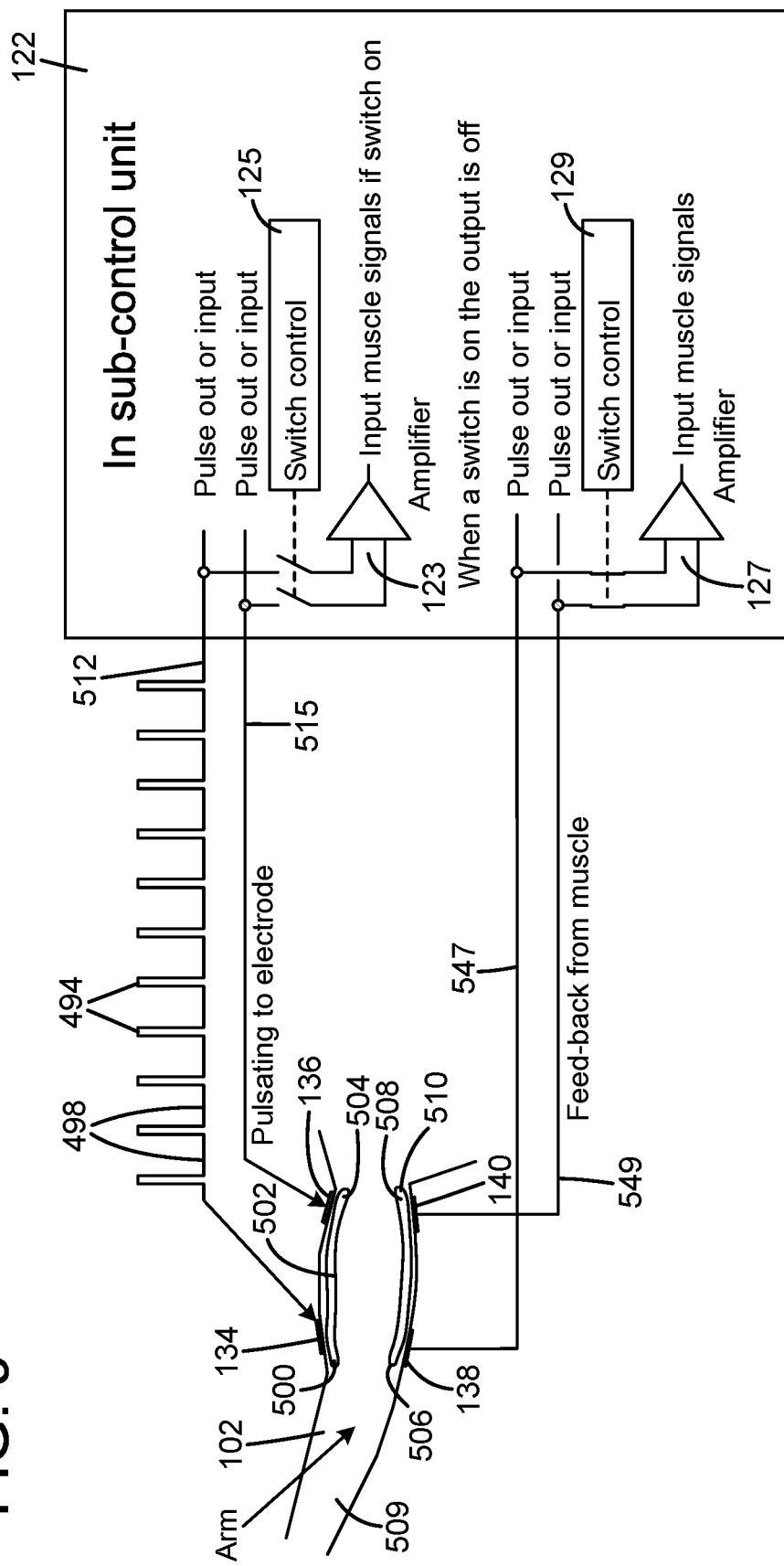
FIG. 9 is a schematic view of a sub-control unit connected to an arm according to the present invention.

FIG. 9 is an illustrative example of a patient's arm 509 inside the right arm module 102 of body suit 100. The arm is shown in an extended semi-straight position although it is most common for spastic patients that the arm is locked in a bent position and the patient finds it difficult or impossible to stretch out or extend the arm without assistance. The electrode 134 may be placed at insertion or first end 500 of an agonist muscle and/or nerve 502 while electrode 136 may be placed at origin or second opposite end 504 of the muscle and/or nerve 502 so that current passes from the sub-control unit 122 via stimulation signal 512 to the electrode 134 via and through the agonist muscle and/or nerve 502 to the electrode 136 and then back via return signal 515 to the sub-control unit 122. The direction of the current flow may be changed so that the current flow goes in the opposite direction, as described in detail below regarding FIG. 15. The electrode 138 may be placed at insertion or first end 506 of an antagonist muscle 508 and the electrode 140 may be placed at origin or second end 510 of the antagonist muscle 508. It is also possible to place the electrodes in the middle of or at another place of the muscle or nerve. It is also possible to use separate electrodes to measure signals from the muscle and other signals such as EMG signals.

For example, the agonist muscle and/or nerve 502 may have a function of moving the arm 509 in a first direction while the antagonist muscle and/or nerve 508 has the function of moving the arm in a second direction that is opposite the first direction. Agonist/antagonist pairs of muscles are needed in the body because muscles can only exert a pulling force and cannot push themselves back into their original position. For example, the upper arm has biceps and triceps muscles. When the biceps muscles are contracting, the triceps muscles are, in a normally functioning person, relaxed and stretched back to their original position. The opposite occurs when the triceps muscles contract. The muscle that contracts may be labeled the agonist muscle while the muscle that is relaxed/stretched may be labeled the antagonist muscle.

An important insight of the present invention is that a mild stimulation of the agonist muscle leads to slight contraction (increased tension) without shortening of the agonist muscle and a relaxation of the antagonist muscle through reciprocal inhibition. When the antagonist muscle is spastic, the muscle is abnormally tense. The agonist muscle should be stimulated without the agonist muscle causing a movement of, for example, the arm. If the agonist muscle is stimulated too much, a movement of the arm is created and the antagonist muscle may respond by becoming tense again which is undesirable. Too much stimulation of the agonist muscle may be caused by using a frequency that is too high, a pulse that is too long or a current/voltage of the stimulation signal that is too high. When the agonist muscle is merely stimulated to generate a signal to the central nervous system without causing the agonist muscle to shorten, the reciprocal inhibition causes the antagonist muscle to relax so that it is in a reduced spastic state. The relaxation of the spastic muscle can sometimes also remove pain in the spastic muscle particularly for patients who do not have a brain damage. The stimulation may also be used to treat pain, tremors, muscle regeneration, induce muscle elaxation, reduce spactisicty, reduce pain, increase muscle tone, facilitate muscle contraction, induce muscle contraction, increase muscle strength/mass, accelerate regeneration of muscles/nerves, increase blood flow/circulation, increase blood oxygenation, reduce vein tension, induce relaxation, improve sleep, reduce tremors, reduce bed soars (abitus reduction), reduce pathological reflexes/central nerve reflexes, treat depression, reduce trauma, use as tension reduction therapy, induce embodiment practice, hyperactivity disorders, autism spectrum diseases and reduce stress disorders.

Signals are sent from the stimulated agonist muscle to the central nervous system that, in turn sends a signal to the antagonist muscle to initiate a relaxation of the antagonist muscle. The relaxation, which is a type of reflex from the central nervous system, is particularly important when the antagonist muscle is a spastic muscle i.e. subject to involuntary or abnormal contraction. The nervous system senses the stimulation of the agonist muscle whereby the antagonist muscle experiences a reciprocal inhibition. The signal from the agonist system to the central nervous system is thus created in an artificial way by first stimulating the agonist muscle with pulses to the electrodes in the body suit of the present invention. The frequency and voltage/current level of the stimulation signals to the agonist muscle needed to induce muscle contraction is higher than the frequency and voltage/current needed on the agonist muscle to cause a relaxation of the antagonist muscle. In other words, the selected frequency and current of the stimulation signal/pulse should be as low as possible to prevent shortening/contraction of the agonist muscle but high enough to be detected by the central nervous system in order to trigger the reciprocal inhibition. A frequency range of 5-200 Hz may be used, more preferred a range of 15-100 Hz and most preferred about 20-60 Hz. It is important to realize that the antagonist muscle must first be relaxed before higher frequencies and current (pulse) levels are used on the agonist muscle to cause it to move. The higher frequencies, current levels and pulse length may be used to contract the agonist muscle so much that it shortens and cause a movement of, for example, an arm. In other words, the stimulation (pulse) signal can be used to artificially make the agonist muscle actively contract without outside physical assistance by, for example, a therapist. As mentioned above, this type of stimulation should not be done before the agonist muscle has been treated with gentle stimulation to cause the antagonist muscle to relax.

It is also possible to measure the brain voltage signals (such as electroencephalogram (EEG) signals) (see FIG. 18 for details) or activity of the person wearing the body suit 100 during treatment so that it is recorded what the brain voltage signals are when the person thinks about moving the arm. This activity can be stored in the master unit so next time the patient thinks that he/she would like to move the arm, the system of the present invention recognizes the brain activity by comparing the measured signals with the recorded signals and artificially provides the correct stimulation signals to the muscle to actively move, for example, the arm in the way the patient wanted according to the brain signals of the person. There may be another different brain signal activity when the patient wants to do something else such opening a hand that the system could also recognize and then (after the antagonist muscle has first been relaxed) sends the appropriate stimulation signal to the correct agonist muscle to open the hand. The master unit may first receive the brain signals and then convert this information to the correct stimulation signals to the various muscles. As best shown in FIG. 9, the master unit 266 sends out the pulsating stimulation signal 512 via sub-control unit 122 to the electrode pair 134, 136 to sufficiently stimulate the agonist muscle 502 to cause a natural signal (triggered by muscle 508) to be sent from the muscle 508 to the central nervous system without causing the muscle 502 to shorten.

The signal 512 includes pulses 494 (as shown in FIG. 8) at a desired pulse frequency such as any value between 1-200 Hz and with short pulse lengths (duty cycle) so that there are time gaps 498 between the pulses 494. By using a sensitive measuring device, it is possible to measure a voltage difference between electrodes 138 and 140 placed on the antagonist muscle 508 or separate sensors. In this way, the voltage signal from electrode 138 is compared to the voltage signal from electrode 140. Preferably, this voltage should be measured during the time gap 498 so that the stimulation pulse 494 does not interfere with the measurement. The measured voltage is indicated in a feed-back signal 547 or 549 signal from the antagonist muscle 508. The feed-back signals are preferably amplified by an amplifier. More particularly, the measuring device should be able to measure micro to millivolts differences between two electrodes that are mounted on the antagonist muscle 508 that is not used for the stimulation. It is important to realize that just because the natural voltage signals from the muscles are so small, it is necessary that the sub-control unit is close to (no more than a couple of decimeters) the electrodes. Otherwise, if the measurement device is far away such at the hip the millivolt signals from the arm muscle disappear into the white noise and/or are interfered with by other electrical signals in the bodysuit. It is also possible to use separate or different electrodes for these measurements. It is thus important that this feedback voltage signal is only measured during the time gap 498 between the pulses 494 so that the stimulation pulses sent to the agonist muscle 502 are not interfering with the delicate measurements at the antagonist muscle 508. It is also possible to simultaneously treat many parts of the body so that signals are simultaneously activated from several sub-control units. Of course, it is also possible to stop sending the stimulation pulses during the measurement of the antagonist muscle when the time to measure between the pulses is too short. The feedback voltage signal between 547 and 549 decreases as the antagonist muscle 508 becomes more relaxed as an indirect result of the mild stimulation of the agonist muscle 502. The feedback voltage signal can be compared to earlier measured values so that it is possible to see how the antagonist muscle 508 becomes more or less relaxed. For example, if the voltage value is first measured to, for example, 2 mV and when the voltage value is gradually reduced to, for example, 1 mV, this means the stimulation effect of the agonist muscle 502 has had a desired effect on the antagonist muscle 508. It is to be understood that it is the naturally occurring voltage caused by the central nervous system in the antagonist muscle 508 that is measured before, during and after treatment of the agonist muscle 502.

The naturally occurring voltage in the antagonist muscle 508 is very small and requires an amplifier to be detected and measured. In the preferred embodiment, the sub-control unit 122 has a first amplifier 123 and a switch control 125 that can be switched between an open or closed position. FIG. 9 shows the switch control 125 in an open position which is the position used when the pulse 494 of stimulation signal 512 is being transmitted to the muscle 502 to stimulate it. When the switch control 125 is in a closed position, the voltage between electrodes 134, 136 may be measured via lines 512, 515, when in between the pulses or when the switch is closed and the stimulation signal 512 is stopped. This means the electrodes 134, 136 may be used not only to stimulate the muscle 502 but also to measure the natural voltage in the muscle after it has been exposed to the stimulation pulses 494. It should be understood that muscles 502, 508 are merely illustrative examples and that all the muscles associated with the sub-control units can be stimulated and measured in the same way. The sub-control unit 122 also has a second amplifier 127 and a switch control 129 that can be switched between an open and closed position. In FIG. 9, the switch control 129 is shown in a closed position which means that the voltage between the electrodes 138 and 140 may be continually measured lines 547, 549 or only measured during the time gap 498 between pulses 494 of signal 512 sent to muscle 502 in case the pulses 494 interferes with the measurement of the voltage in muscle 508. In this way, it can be determined how the naturally occurring voltage (caused by signals from the central nervous system) between electrodes 138, 140 placed on muscle 508 changes as a result of the pulse stimulation of muscle 502. In general, as the muscle 508 becomes more relaxed the naturally occurring voltage between the electrodes 138 and 140 decreases. As indicated above, it is important to only measure the voltage between electrodes 138, 140 during the time gap 498 of the stimulation pulses 494 of signal 512 to muscle 502 because if the measurement is done during the duty cycle of one of the pulses 494 then there is a risk that the pulse would interfere with or distort the voltage measurement between electrodes 138, 140 mounted on muscle 508. It is also possible to measure the voltage between electrodes 134, 136 mounted on muscle 502 during the time gap 498 while muscle 502 is being treated with the stimulation pulses 494. This can be done by switching the switch control 125 to the closed position during the time gap 498 and then switch it to the open position before the next pulse 494 is sent to muscle 502. In this way, the changes of the naturally voltage of the muscle 502 that is being stimulated can also be measured. It is also possible to stop the pulsating stimulation signal while the measurements take place. It is to be understood that the measurements described above apply to all the electrodes connected to the sub-control units and combinations of stimulations via the electrodes connected to the sub-control units.

Instead of using a separate device to measure the feedback signal in the antagonist muscle 508 which means the stimulation signals 512 of the agonist muscle 502 must be stopped during the measurement, it is desirable to make it possible to measure the antagonist muscle 508 during the treatment of the agonist muscle 502 i.e. continuously or during the time gaps 498 between the stimulation signals 512 that are sent to the agonist muscle 502. The measurement of the muscle 508 may result in that the stimulation of the muscle 502 should be changed to a different program or the parameters should be modified such as changing the voltage, current, frequency or pulse length of the stimulation signal 512. The stimulation of muscle 502 is thus artificially created by sending the stimulation pulses 494 in signal 512 to the electrode 134 while it is the naturally occurring voltage of the antagonist muscle 508 (reciprocal inhibition) that is measured and how the current changes in muscle 508 as a result of the artificial stimulation of agonist muscle 502. It is desirable to also save the frequency, amplitude of the current/voltage of the stimulation signal 512 that stimulated agonist muscle 502 so that the same parameters can be used the next time the muscle 502 needs to be stimulated. As explained in detail below, it may be necessary to calibrate the signal 512 if it is a voltage mode pulse because the natural resistance of the muscle or the contact of the electrodes with the skin changes over time due to, for example, different humidity or the skin of the patient contains more moisture compared to the prior measurement or changes in the connections between the electrodes and the skin of the person wearing the bodysuit. However, if it is a current controlled pulse it can be regulated to a fixed current (current mode). For example, it may be necessary to increase the voltage of the signal 512 to provide the same amount of current running through muscle 502, as described in detail in FIG. 10. This information may be saved in the master unit 266 that is connected to the body suit 100 so that master unit 266 can ensure that the correct amount of current flows through the agonist muscle 502 to give the right stimulation of the agonist muscle. The master unit may also continuously measure the current of the stimulation pulses so it knows in a future stimulation how much current was required.

The master unit may also calibrate the parameters during the treatment such as increasing or decreasing the voltage or current if, for example, the patient starts perspiring during the treatment which affects the conductivity. This adjustment mechanism makes sure the muscle 502 is correctly stimulated even if the external conditions change from one treatment to another treatment or throughout the course of a treatment. It is also possible to reverse the stimulation to stimulate muscle 508 instead. The switch control 129 is then switched to an open position when stimulation pulses are sent to muscle 508 while the switch control 125 is switched to a closed position so that the naturally occurring voltage signal from the muscle 502 can be measured by measuring the voltage between the electrodes 134, 136 via lines 512, 515 during the time gap between the stimulation pulses sent to muscle 508.

Figure 10:
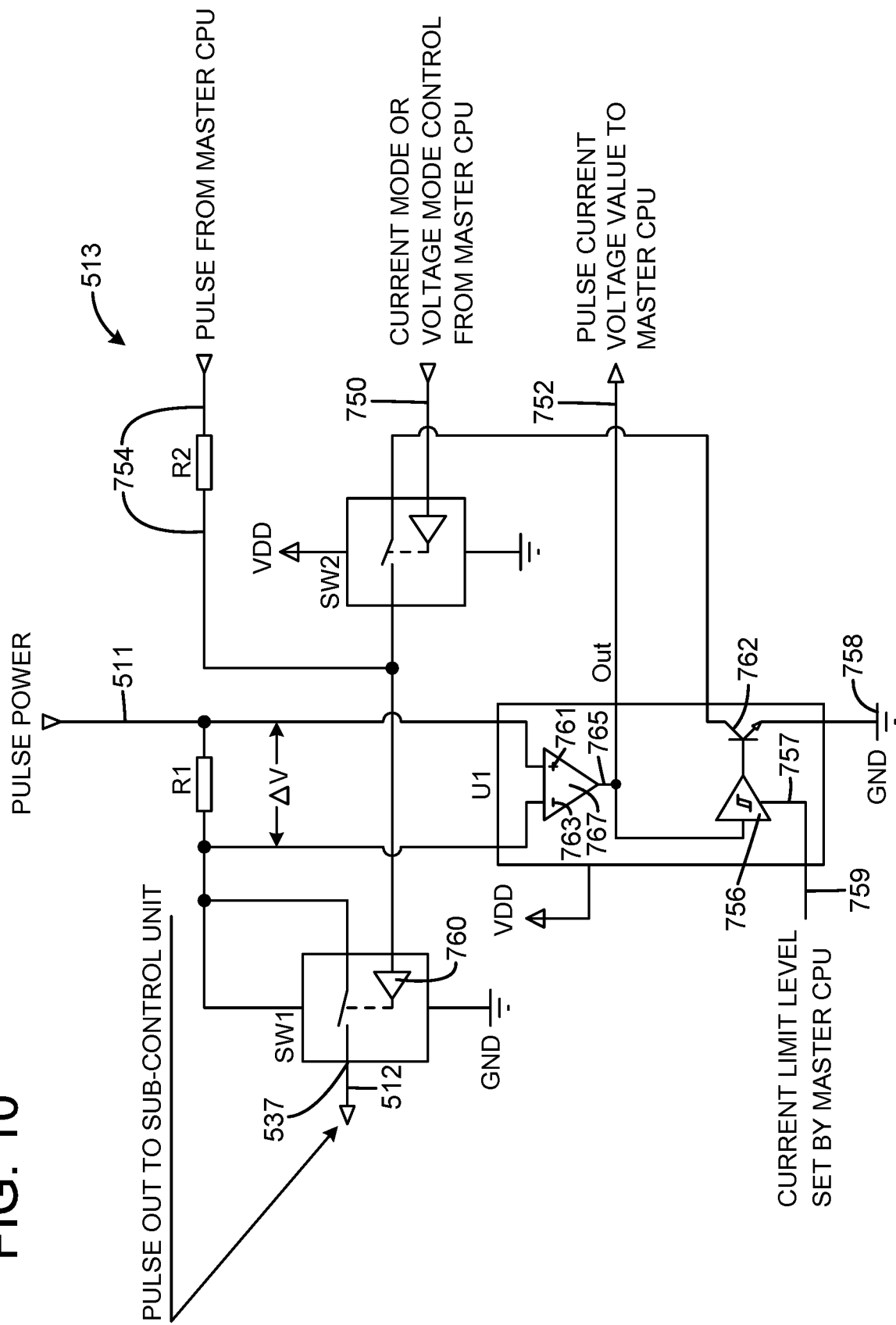
FIG. 10 is a schematic view of an arrangement that is switchable between a voltage mode and a current mode according to the present invention.

FIG. 10 is a schematic view of a suitable circuitry arrangement 513 in the master unit 266 of the present invention wherein the arrangement is changeable between either a voltage mode or a current mode which makes it possible to automatically control and adjust the current flowing through the muscle as a result of the stimulation pulse signal 512. An important feature of the arrangement 513 is that it is adaptive and adapts the voltage and other parameters of the stimulation signal 512 based on the feedback information regarding the estimated amount of current flowing through the stimulated agonist muscle 502 as indicated by the voltage-drop across resistor R1. The estimated current is calculated from the delta voltage of the voltage-drop divided by the resistance of resistor R1 and the gain from amplifier 767. The arrangement is thus self-learning or automatic and makes the necessary adjustments of the stimulation signals based on the feedback in the pulse current value signal 752 that is an input to the master CPU. In other words, the arrangement 513 may be used to continuously determine or estimate the amount of current flowing through the agonist muscle 502 as a result of the stimulation signal 512 in FIG. 9. It is thus possible to exactly provide and measure the current needed in, for example, the agonist muscle 502 to effectively relax the antagonist muscle 508. The feedback signal 752 to the master unit may also used to detect an insufficient or lack of contact between body and electrodes. If there is no contact between the body and the electrodes the measured current is zero.

FIG. 11A shows a stimulation current pulse 531 as the current is measured and regulated by arrangement 513 when the current goes through the muscle that is stimulated and FIG. 11B shows a stimulation pulse 519 as the delta voltage is measured across resistor R1 as the stimulation pulse leaves switch SW1 to the sub-control unit and electrodes with the current control activated (i.e. when the arrangement 513 is in the current mode). It should be noted that the y-axis in FIGS. 11A-B is expressed in ampere (A) and the x-axis is expressed in time. The resulting current of pulse 531 that moves through the muscle is substantially constant with a low ripple as the current level moves or oscillates between a narrow band of a maximum value and a minimum value. This control of the current level is an important feature of the present invention. The actual current of the stimulation pulse is determined by the low ripple current as set by the current limiter signal from the CPU of the master unit 266. An important insight of the present invention is that in order to accomplish a substantially constant current it is necessary to control the current by adjusting the voltage level until the right current level is achieved. This is automatically done by the arrangement 513 shown in FIG. 10. Another important feature of using a substantially constant current (with low ripple) is that when there is a poor contact between the electrodes and the skin, the constant current circuit arrangement 513 automatically increases the pulse voltage until a sufficient amount of current is passing through the muscle assuming that a pre-set voltage maximum is not exceeded for safety reasons. However, when the voltage is constant (as in the voltage mode) this automatic adjustment feature is not possible.

FIG. 11D shows a voltage stimulation pulse 520 (wherein the voltage is constant) as the pulse leaves the switch SW1 to the sub-control unit and electrodes without the current control activated (i.e. when the arrangement 513 is in the voltage mode). FIG. 11C shows the resulting current when measured as it moves through the muscle. It should be noted that the y-axis in FIG. 11C is expressed in ampere (A) over time (x-axis) while the y-axis in FIG. 11D is expressed in volt (V) over time (x-axis). The muscles first acts as a capacitor and then as a resistor so that the flank of the voltage pulse results in a high current peak 521 while charging the muscle (capacitance) between the electrodes during the flank of the pulse and the muscle resistance then sets the end current level 525 after the charging is done. In this way, the current is very high in the beginning of the treatment of the muscle and this can be very uncomfortable to the patient wearing the bodysuit 100. One important advantage of using the current mode (see FIGS. 11A and 11B) is that it prevents the initial peak of the current because the current only fluctuates between current start 516 and current stop 518. However, as the electrode age an internal resistance builds up so that the current changes according to curve 523 that does not have a high peak in the beginning. It should also be noted that due to the internal resistance of the electrode, the current in the muscle in curve 523 reaches a maximum ampere that is lower than the current level 525 that is reached when the electrode is new (very little internal resistance) so it may be necessary, when it is in the voltage mode, to raise the voltage in pulse power 511 to compensate for the internal resistance in the electrode and so that the maximum in curve 523 reaches the current level 525.

The outgoing stimulation pulse 512, whether in the current mode or in the voltage mode, is sent from the arrangement 513 of the master unit 266 via output from switch SW1 to the sub control units and the CPU of each sub-control unit senses the incoming pulse and the pulse also powers up the output unit 535 (see FIG. 15) of the sub-control units such as sub-control unit 122. It has been realized that when electrodes age over time their resistance often increases which results in an increased voltage drop at the electrodes and this results in less voltage across the muscle and the current through the muscle drops. This means that the current through the muscle has tendency to decrease although the voltage input to the electrodes of the stimulation pulses remains the same when in the voltage mode. Another factor is that the internal resistance of the muscles that are treated/stimulated may build up over time which, in turn, reduces the current that flows through the muscles when the voltage is constant (i.e. when in the voltage mode).

A CPU of the master unit 266, that is electrically connected to the arrangement 513 (in FIG. 10), determines whether the arrangement 513 should be in the current mode or the voltage mode according to the set signal 750 sent from the CPU of the master unit to the arrangement 513. The set signal 750 is either in "0" mode that may represent voltage mode so that the outgoing pulse looks like pulse 520 in FIG. 11D or in "1" mode that may represent the current mode so that the outgoing pulse current looks like pulse 519 in FIG. 11B. The "1" mode may be at any suitable voltage such as 3.3V, 5V or any other desired voltage level as long as it is substantially lower than the voltage of pulse power 511. When the arrangement 513 is in voltage mode, the CPU of the master unit sets the voltage 511 to the desired level. When the arrangement is in the current mode, the CPU of the master units, preferably, sets the voltage in pulse power 511 to a maximum allowable value (such as 40V). This is possible to do because the arrangement 513 self-regulates the current and provides the required high voltage level to maintain constant current. Circuitry U1 measures the voltage over resistor R1 in both cases, i.e. whether the arrangement 513 is in current mode and voltage mode, but cannot control the current when the arrangement 513 is in the voltage mode. The CPU of the master unit is preferably programmed to the desired mode by software in a computing device such as a personal computer, pad or telephone. The stimulation parameters are installed in the master unit from a regular computer, pad or telephone that communicates with the master unit 266 via wired or wireless communication. One advantage of using the current mode is that if the internal resistance of the muscle has increased or there is not a good contact between the skin and the electrode then the circuit 513 increases the voltage of the stimulation signal or pulse power until the desired current flow between the two electrodes is obtained. Preferably and for safety reasons, there is a maximum limit of how much the voltage in pulse power 511 can be set to. If the arrangement is in the voltage mode, i.e. the voltage of the stimulation pulse is constant at, for example, 20V, and when the resistance in the muscle increases or the electrodes wear-out over time then the current flow in the muscle drops and in some instances the current may stop flowing.

Figure 19:
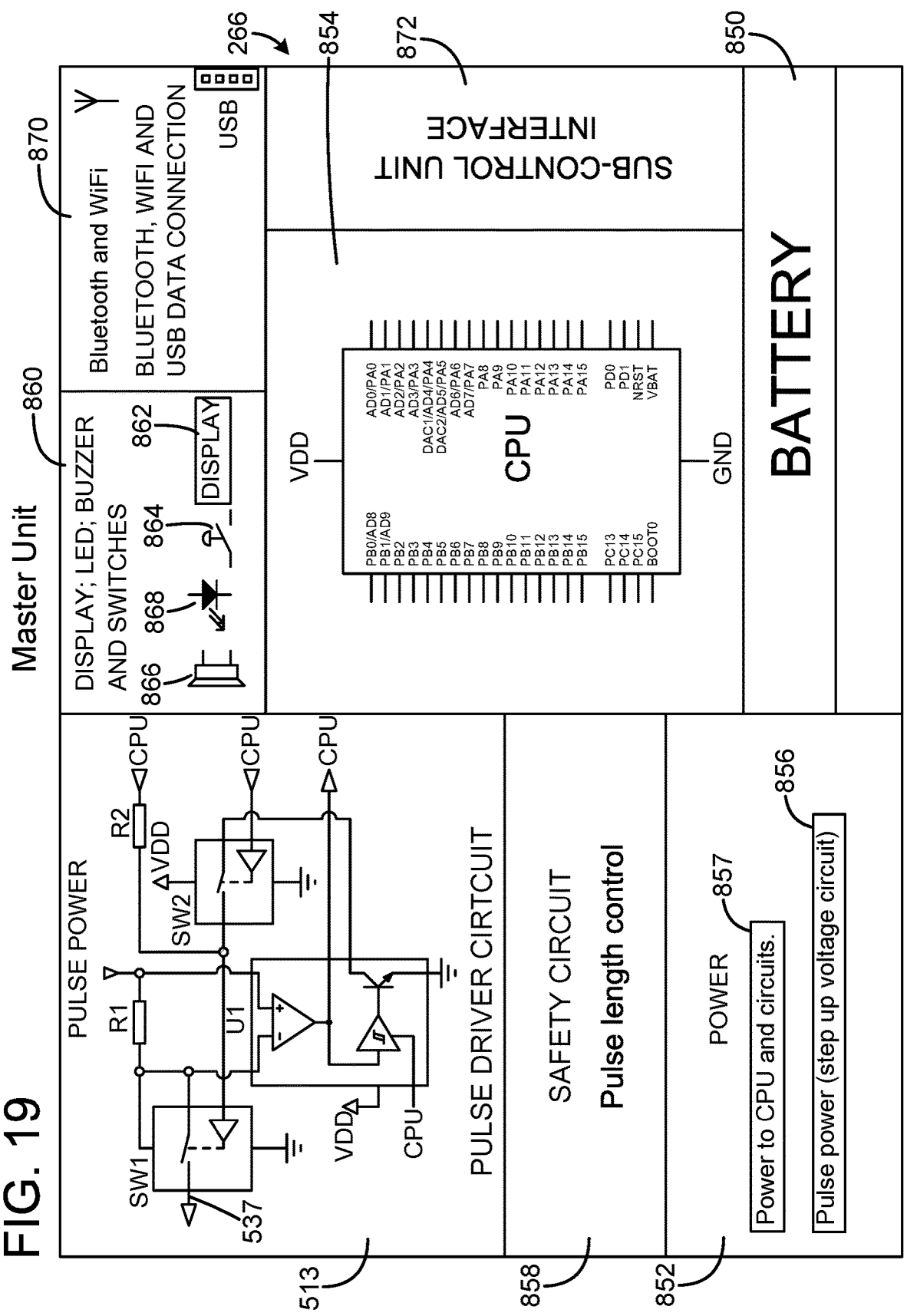
FIG. 19 is a schematic view of components of the master unit according to the present invention.

More particularly, a power unit of the master unit 266, shown in detail in FIG. 19, sends an activation pulse 754 (see FIG. 10) via resistor R2 to input on switch controller 760 of switch SW1. The activation pulse 754 can either be in "1" mode to close switch SW1 so that the pulse power voltage 511 can pass through switch SW1 that creates the stimulation pulse signal 512 that continues to the sub-control units. The activation pulse 754 can put the switch SW1 in "0" mode which opens switch SW1 so that no pulse power voltage 511 can pass through switch SW1. Preferably, the activation pulse 754 is at a voltage level (for example 3.3V or 5V) that is substantially lower than the voltage level of the pulse power voltage 511 (for example 20-40V). Signal or activation pulse 754 thus opens and closes switch SW1 at the desired pulse interval and pulse length as determined by the CPU of the master unit so that it is the pulse 754 that sets the frequency of the pulsation of the stimulation signal 512. The CPU in the master unit 266 determines the pulse length by sending the activation pulse to switch SW1. The activation pulse signal 754 creates the pulsation of the stimulation signal 512 that leaves the switch SW1 as a pulse at for example 20V. The time period the activation pulse is in "1" mode is the pulse length or duty cycle of the pulses of the outgoing stimulation signal 512. The stimulation pulse signal 512 then goes to the sub-control unit that forwards or distributes the incoming stimulation pulse to the correct electrode or electrodes and sends out the correct pulse length that was earlier sent to the sub-control unit by the master unit. The voltage level or amplitude of the voltage pulses 494 in stimulation pulse signal 512, when in the voltage mode, may thus be set by the CPU of the master unit and can vary between, for example, 10-100V. Voltage levels of 20V or 40V are commonly used but can thus be varied. When an "1" signal of control or activation signal 754 is sent then the switch SW1 closes so that the voltage of pulse power voltage 511 can pass through switch SW1 and the outgoing pulse length of stimulation signal 512 is controlled by the time length the signal 754 is in "1" mode before switching to the "0" mode to open switch SW1. When the switch SW1 is open, the delta voltage across resistor R1 is 0 i.e. no current flows therethrough. The activation signal 754 comes from the CPU of the master unit so that the outgoing voltage stimulation signal 512 from arrangement 513 at output 537 looks like pulse 520 and the pulse length of the stimulation signal is determined by the activation pulse 754 because when the activation pulse opens switch SW1, i.e. switches to "0" mode, the pulse power 511 can no longer pass through switch SW1 and this creates the time gap 498 between the pulses 494, as shown in FIG. 9. In other words, as long as the activation pulse 754 is in the "1" mode, such as for 175 microseconds or any other pulse length, to keep the switch SW1 closed, a stimulation pulse can flow through switch SW1 and on to the sub-control units and the electrodes. In this way, the activation pulse 754 creates one pulse length of the stimulation signal until it switches to "0" mode again to open the switch SW1 that starts the time gap 498. All sub-control units in the body suit receives the pulses 494 and each sub-control unit decides if it should send out the pulse or not to the electrode based on its instructions sent to the sub-control units from the master unit 266.

When pulse power voltage 511 passes through resistor R1 and a voltage drop is formed over the low value resistor R1 (if current flows), this voltage drop is continuously measured by circuitry U1 to determine the amount of current of pulse power voltage 511 that passes through resistor R1. Circuitry U1 measures the voltage difference (for each stimulation pulse that passes through switch SW1) from the voltage at the positive pole 761 i.e. prior to resistor R1 which is the voltage of the incoming pulse power voltage 511 to the voltage at the negative pole 763 after the resistor R1. When the current starts flowing through the R1 and through muscle which results in the voltage drop signal at resistor R1 that circuitry U1 reads and sends out in the signal at 765 and feedback signal 752. The information about the voltage difference is preferably amplified by circuitry U1 and sent in the pulse current value as a voltage signal 752 to the CPU of the master unit. The CPU or a A/D converter converts the current value voltage signal 752 to a digital value for the CPU. Because the resistor R1 has a very low Ohm value, the voltage drop is in the order of millivolts. The resistor R1 should be of a very low resistance to minimize the voltage loss as the pulse power 511 passes through resistor R1 and onward to the switch SW1 and out as a stimulation pulse. Preferably, the signals 765 and 752 are amplified by an amplifier 767 so that the signals 765 and 752 are measurable or readable by the CPU of the master unit. By knowing the resistance of resistor R1 and the amplification at circuitry U1, it is possible to determine the current. Preferably, resistor R1 should have a low resistance such as 0.1 to 10 Ohm to minimize the losses of voltage in the pulse signal 512. The information in the feedback signal 752 is important because it informs the CPU of the master unit 266 when, for example, there is insufficient current which may be the result of a poor contact between the electrodes and the skin so that insufficient or no current is flowing between the electrodes mounted on the stimulated muscle and through the muscle.

When feedback signal 752 indicates to the CPU of the master unit 266 that the current is decreasing as determined by the voltage drop across resistor R1, it could be used by the CPU as a trigger to switch from the voltage mode to the current mode by changing the signal 750 from a "0" mode to "1" mode to close or activate switch SW2 or to increase the voltage at 511 in voltage mode to increase the current. It should be noted that the change of the voltage in the voltage mode cannot be done for each pulse. Instead, it has to be over time and it is the value of the average current read value of 752 that decides if the voltage should be raised or not. It is also possible to increase the voltage of the pulse power signal 511 while in the voltage mode to increase the current flowing through the muscle if it turns out that, for example, the resistance in the muscle has increased. However, it is not possible for the circuitry U1 to control the current flow for each pulse when the arrangement is in the voltage mode. As explained above, often the muscles behave like capacitors in series with the muscle and electrode resistance so that the current rapidly increases in the beginning of the pulse and then rapidly declines wherein the resistance in the muscle sets a lower limit of the current flow during the duty cycle of the stimulation pulse.

The pulse current value signal 752 could be used by the CPU of the master unit as a feedback signal to determine whether a previous increase of the voltage in pulse power voltage 511 had any effect on the current flowing through the stimulated muscle, as measured by the voltage drop across the resistor R1. The aging of the electrodes creates a problem in that the internal resistance in the electrodes can increase over time. Another problem of using the voltage mode is that the resistance in the muscle is not linear so it is difficult to control and to make sure there is sufficient current flowing through the muscle when in the voltage mode. An average value of feedback signal 752 may thus provide information to the CPU of the master unit 266 about the need to increase the voltage of the pulse voltage 511 to make sure sufficient current is flowing between the electrodes. It is to be understood that the CPU may increase the voltage of the pulse power voltage 511 whether the arrangement 513 is in voltage mode or current mode. The "1" mode of activation signal 754 may be at any suitable voltage such as 3.3V, 5V or any other desired voltage level.

Switch SW1 is a switch that connects the pulse power voltage 511 to the sub-control units that then forward the stimulation pulse signals 512 to the selected pair of electrodes. As indicated above, the resistance of resistor R1 is so low that it does not really affect the voltage of the outgoing pulse signal 512. The control or activation pulse 754 thus repeatedly opens and closes switch SW1 to disallow or allow, respectively, the pulse power 511 to pass through the switch SW1 as stimulation pulse signal 512 and circuitry U1 continuously measures the voltage drop across low value resistor R1 that the current causes at resistor R1 to indirectly determine the amount of current flowing through the muscles that are treated.

It should be noted that circuitry U1 measures the current (i.e. voltage drop across the resistor R1 caused by current through resistor R1) regardless whether the arrangement 513 is in current mode or in voltage mode. When switch SW2 is open ("0" mode), i.e. the arrangement is in the voltage mode, then the circuitry U1 can merely measure the voltage drop over resistor R1 but cannot effectively control the outgoing current in the outgoing stimulation pulse signal 512 that leaves at output 537 and goes to the sub-control unit 122. The incoming activation pulse 754 from the CPU of the master unit is a low-level pulse that enables (when in "1" mode) the high voltage pulse power 511 to pass through switch SW1 by closing the switch SW1 to create the outgoing stimulation pulse signal 512 at output 537. The pulse power 511 may have any suitable voltage, such as 10-40V, as controlled by the CPU of the master unit.

When switch SW2 is closed ("1" mode), as set by the digital mode ("0" or "1") of the incoming set signal 750 from the CPU of the master unit 266, then circuitry U1 can affect the outgoing current of the stimulation signal 512. The circuitry U1 can temporarily open switch SW1 by connecting the SW1 control pin to GND during the activation signal 754 when the current, as determined by the measured voltage drop over resistor R1, has increased to an upper threshold value (stop current) in circuitry U1. When circuitry U1 detects that the voltage drop across resistor R1 has increased so that corresponding current has reached the upper threshold value, i.e. the stop current value (as set by the current limit pin on circuitry U1 759) then circuitry U1 connects the SW1 control pin to GND to stop the activation pulse 754 so that switch SW1 opens. When the switch SW1 is temporarily opened by circuitry U1 then the delta voltage across resistor R1 declines until a current start 516 value is reached when the circuitry U1 releases SW1 control pin from GND so that pulse 754 closes switch SW1 again by allowing pulse 754 to close switch SW1. More particularly, when the circuitry U1 senses that the voltage-drop (delta V) has declined so that start current 516 value has been reached then circuitry U1 releases the SW1 control pin and switch SW1 closes again so that the pulse power voltage 511 can continue to pass through the switch SW1 and the delta voltage across the resistor R1 starts increasing because the current starts flowing through the muscle again. The current of the activation pulse 754 to SW1 control pin is limited by resistor R2 when circuitry U1 connects signal 754 after resistor R2 to GND. When the circuitry U1 detects that the voltage-drop across resistor R1 is such that the current start 516 has been reached, then circuitry U1 releases the SW1 control pin and switch SW1 closes again and the voltage of the pulse is connected to the electrodes and the current can start flowing through the muscles and electrodes and the current increases until stop current 518 when the comparator 756 with integrated hysteresis stops the activation signal 754 again so that switch SW1 opens. In this way, circuitry U1 controls the current flow in the stimulated muscle during the pulse duty cycle of stimulation pulse 512 when switch SW2 is closed or active. It is to be understood that the fluctuation of the current between start current and stop current is so rapid that there is not enough time for the CPU to be involved. This is why the comparator 756 is used. The voltage to switch SW1 is generated via resistor R1 and the activation pulses 754 to switch SW1 that are sent by the CPU of the master unit 266 and the switch SW1 is activated or de-activated by the activation/control signal 754. When the activation/control signal 754 is temporarily stopped by circuitry U1 and when switch SW2 is in the current mode this in turn opens the switch SW1 so that no pulse power current 511 can flow through switch SW1. When the CPU of the master unit 266 sends out a pulse activation command (i.e. "1" command) in the control signal 754 via resistor R2 then the switch SW1 closes and the pulse power voltage 511 can pass through switch SW1. When the sub-control unit 122 then sends the pulse to a selected electrode pair and muscle, the current flow starts and this creates the voltage drop over resistor R1. This voltage drop across resistor R1 is continuously measured by circuitry U1 that converts it to the feedback signal that is sent to the CPU of the master unit as the pulse current value signal 752. The CPU in the master unit 266 reads the voltage drop information in signal 752 as a value of the current of the outgoing pulses of stimulation signal 512. When the CPU of the master unit has selected the current mode (i.e. set signal 750 is in the "1" mode) then the switch SW2 is activated or closed. The corresponding current (as measured by the voltage across resistor R1) that is measured by circuitry U1 is compared to the upper threshold value or current limit of the current as set by the CPU of the master unit. When the current has reached the upper threshold voltage value (stop current 518 in FIG. 11B) then the transistor or switch 762 connects the SW1 control pin to GND to short-circuit the control/activation signal 754 after resistor R2 (wherein resistor R2 is a current limiter) as determined by the current limiter comparator 756 in circuitry U1. This assumes that the voltage of the pulse power 511 is high enough, considering the total resistance in the system, so that the current would increase to a value higher than stop current 518. When the current reaches the upper threshold, the current limiter comparator 756 short-circuits the signal 754 after resistor R2 so that switch SW1 opens and the current flow stops and the current starts decreasing. When the current has decreased to the start current 516 (as shown in FIG. 11B), the switch 762 disconnects the SW1 control pin from ground GND so that pulse power 511 can pass switch SW1 and the current can start flowing again. The pulse signal 754 is in "1" mode (at 3.3-5V) before resistor R2 but in "0" mode (i.e. the voltage is 0) after resistor R2 when switch 762 is closed and leads pulse signal 754 to ground 758. Resistor R2 protects the CPU when there is a short-circuit to ground because it limits the amount of current that can flow therethrough. The resistor R2 could be in a range of 5-15 Ohm and more preferred about 10 Ohm. The switch controller 760 senses the change of pulse signal 754 to "0" mode and opens the switch SW1. The closing and opening of the switch/transistor 762 are controlled by the current limit comparator 756. The comparator 756 has a current limit inlet 757 that is controlled by the CPU of the master unit so that the CPU can set the value of the current by sending a voltage value 759. The difference between start current 516 and stop current 518 is preferably constant and the signal 759 sets the level or limit of, for example, the stop-current 518 which means it indirectly also sets the limit for start current 516 since the difference (delta) between the start current and stop current preferably remains the same and is determined by the hysteresis of comparator 756. Preferably, the voltage difference should typically be about 20 mV but can be set to another value also. In this way, the signal 759 can increase or decrease the average voltage value (which is equivalent to an average current value) that is sent to the CPU of the master unit 266 in signal 752. The comparator 756 compares the value of the amplified voltage drop signal 765 with the current limits of the voltage value 759 and when the voltage drop signal 765 has reached the current limit (stop current 518 in FIG. 11B) then the comparator 756 closes the switch/transistor 762 so that the activation pulse 754 goes to ground 758 and the switch SW1 opens. This stops the current through the resistor R1 and the current of the stimulation signal 512 decreases and when the delta voltage has decreased to a level that is equivalent to start current 516 (see FIG. 11B) then the comparator 756 opens the switch 762 so that switch SW1 closes again and the current of the stimulation signal starts increasing as shown by the increase of the voltage drop signal 765 from circuitry U1. The switch 762 is kept open until the current, as indicated by the delta voltage across resistor R1, has increased to the stop current value and the switch 762 is closed again by comparator 756. The comparator 756 may have pre-set hysteresis values so that the comparator has an upper level and a lower level that it compares the current value against. Preferably, the comparator has one built-in hysteresis value that corresponds to the current start value 516 (and current stop value 518) and the CPU of the master unit sets the value for stop current 518. The opening and closing of switch 762 are extremely quick (such as nano-seconds) and occurs during the duty cycle of the pulse 494 so that the switch 762 is opened and closed many times during the pulse. It is important that the voltage of the pulse power 512 is sufficiently high so that the current can increase from the start current 516 to stop current 518 when the arrangement is in the current mode. The amount of current is determined by the resistance in the muscle, electrodes and wiring.

The current thus fluctuates between the upper stop current 518 and lower threshold (start current 516) values, as shown in pulse 519 in FIG. 11B. The opening and closing of switch SW1 occur during the duty cycle of stimulation pulse 494 so the time frame is very short i.e. nanoseconds. It should be noted that the size of the current that flows through the muscle, i.e. between the electrode pairs mounted on the muscle, is partially decided by the natural resistance in the muscle and which current that is selected by the signal 759.

It may also be possible to apply the principles of the present invention to, for example, a hand or wrist that is stiff relative to the lower arm so that the hand is fixed in a downward position and the patient is unable to rotate the hand in an upward direction. Today, the hand must be forcibly moved in the upward direction. This is very unpleasant to the patient. An important feature of the present invention is to first send stimulation signals to the agonist muscle located on the upper side of the lower arm to indirectly relax the tense antagonist muscle located on the lower side of the lower arm. The amount of relaxation of the antagonist muscle may be determined by measuring the amount of voltage-out (EMG) in the antagonist muscle and how this has changed when it is connected to an electrode pair. After the antagonist muscle has been relaxed for a certain time period so that there is less resistance of the muscle to be extended, a relatively high voltage or current signal is sent to the agonist muscle located on the upper side of the lower arm so that the agonist muscle shortens enough to cause movement/contraction of the agonist muscle (while the relaxed antagonist muscle extends) to lift the hand at the wrist in the upward direction relative to the lower arm without using an external mechanical force. This stimulation signal may have a higher voltage, a higher predetermined current or a longer pulse length (duty cycle) than the parameters used to merely stimulate the agonist muscle (in order to relax the antagonist muscle) so that the stimulation signal contracts the stimulated muscle in order to move the arm.

Figure 12:
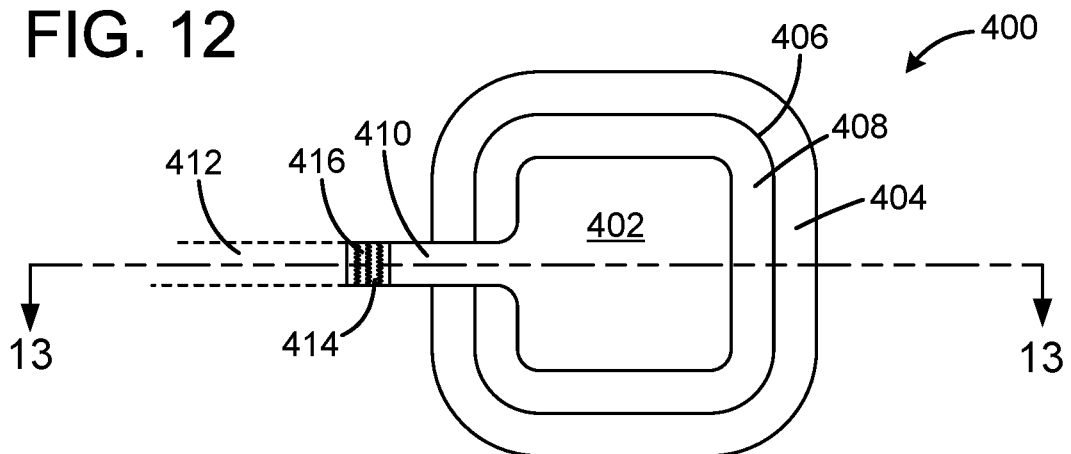
FIG. 12 is a schematic top view of an electrode according to the present invention.
Figure 13:
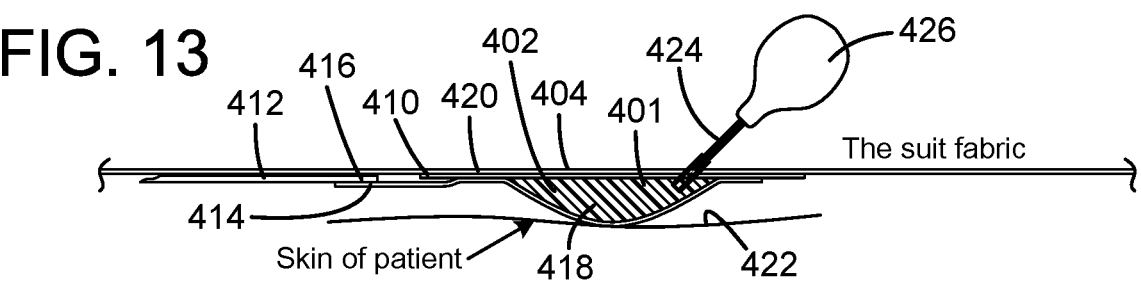
FIG. 13 is a schematic cross-sectional view of an electrode shown in FIG. 12 according to the present invention.

FIG. 12 is a top view of an electrode 400 of the present invention while FIG. 13 is a cross-sectional side view of the electrode. Preferably, the electrode 400 includes a conductive rubber material that is covered by a conductive layer of gold, silver or any other conductive material. The electrode should have no sharp edges. The electrode may, for example, be made of a conductive woven fiber or silver tread, gold thread, copper wires, stainless steel surgical wires and silicon wires.

The electrode 400 is an illustrative example of an electrode and could be one of the electrodes 134, 136 etc. shown in the body suit 100 in FIG. 4. The electrode 400 has a protruding mid-section 402 that is made of a thin electrically conductive rubber, with metal plating such as gold or any other suitable conductive material. The mid-section 402 may contain a soft filling material and/or be hollow so that it is inflatable and deflatable. Preferably, the fabric 404 of the body suit 100 extends over the outer edge 406 of the mid-section 402 so that the fabric overlaps an outer portion 408 of the mid-section 402. The fabric 404 is attached to the outer portion 408 in a suitable way such as using an adhesive. One advantage of using a conductive metal plating is that it slides better on the skin of the patient wearing the body suit 100. Conventional electrodes made of a rubber material has a high friction against the skin that makes it harder to take on and off the body suit. A low friction coefficient of the mid-section 402 is important when the body suit is put on and taken off the patient so that the electrodes slide on the skin. A backside of the electrode 400 may have an electrically conductive layer of a rubber material. Preferably, the fabric 404 outside the outer portion 408 is sewn to the body suit. The mid-section 402 has an electrically conductive connector 410 that extends outwardly beyond the outer portion 408. The connector 410 may overlap a flexible conductive wire 412 that is connected to one of the sub-control units. An outer portion 414 of the connector 410 may be attached to an outer portion 416 of the wire 412 such as by sewing them together. The mid-section 402 may be filled with a soft spongy material 418 so that the mid-section 402 protrudes away from the fabric 420 of the body suit 100 so that it is urged against the skin 422 of the patient wearing the body suit 100 to improve the contact between the skin and the electrode. The electrode 400 may also include a tubular portion 424 that extends through the fabric 404. The tubular portion 424 may be connected to a balloon-shaped pump 426 that may be used to inflate the inside 401 of electrode 400 so that it expands and protrudes more to further improve the electrical contact between the metal mid-section 402 and the skin 422. An important feature is that the tubular portion 424 and/or the balloon-shaped pump 426 may be removably attached so that they may be removed and connected to another electrode that needs to be expanded by pumping it up. It is also possible to provide the electrodes with a valve to release the pressure/air when the mid-section 402 becomes too hard and the valve automatically closes when the pump 426 is removed. The rear-part of the fabric 404 is sewable so that the electrodes can be sewed to the fabric of the body suit 100. Preferably, only the mid-section 402 is pumped but not the connector 410. The electrodes can also be woven into the elastic bodysuit wherein the electrodes are woven with conductive threads. The conductors to the sub-control units can also be woven into the bodysuit with conductive thread so that they can be connected to the sub-control units and the sewable connections are sewed together.

Figure 14:
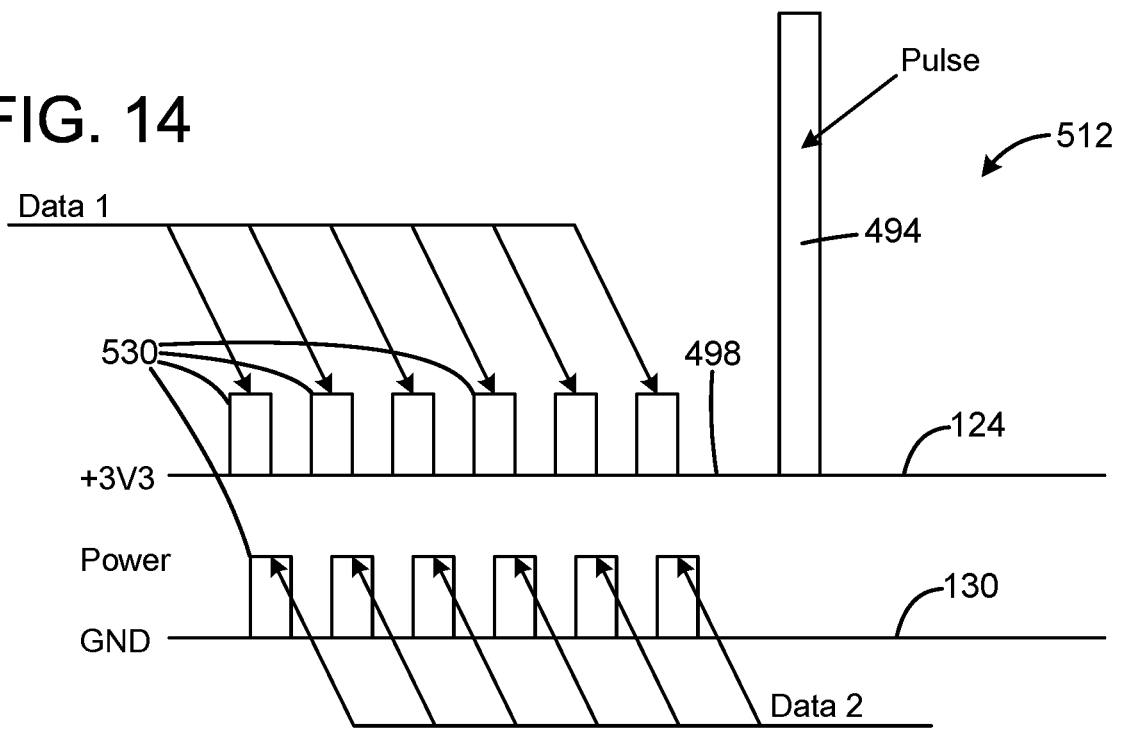
FIG. 14 is a schematic view of a stimulation pulse signal that includes data pulse according to the present invention.

FIG. 14 shows one possible solution of sending power, data and pulses to the sub-control units by using a serial data-bus. It is possible to superpose data on the power sent to the sub-control units (power 3V3, 5V and GND) so that the master unit can send out data with instructions to the sub-control units about what the sub-control units should do. When the instructions have been received by a particular sub-control unit then, based on the instructions in the data, it knows, when it receives a first pulse at a higher voltage level (such as 20-40V), that it shall send the pulse to the first electrode pair that is are in the programmed transmission list of the instructions. When the second pulse arrives to the sub-control unit sends the second pulse to the next pair of electrodes listed in the instruction list etc. Preferably, the stimulation pulses are always at a higher voltage level than the power voltage and data pulses so that the sub-control unit can easily distinguish the stimulation pulses from the data pulses and power pulses. Data information is preferably sent at a high frequency to the CPU of the sub-control unit. The use of only two wires is merely an example of a suitable solution but more than two wires may also be used. For example, three wires may be used to each sub-control unit wherein two wires are used for power, positive and negative pole and data and the third wire is used for sending the pulse. Data instructions may also be sent by using wireless communication technology such as Wi-fi, Bluetooth etc. It is also possible to use two wires wherein the two wires are used to send both power and pulses while the data is sent by wireless communication technology such as Wi-fi, Bluetooth etc. A portion of pulse signal 512 to the sub-control unit 122 is shown in FIG. 14 to illustrate the pulse 494 and a time gap 498 between data and stimulation pulses. It is possible for the master unit 266 to send data units 530 between the high voltage stimulation pulses to the sub-control unit such as sub-control unit 122 (see FIG. 5) that receives the data units 530 via extensions 124*b*, 130*b* and wires 124*a*, 130*a*, respectively, from the master unit 266. The data units 530 are preferably sent to the sub-control units during the start up so that the sub-control units receive instructions in the data units about which and when electrodes should be activated. In other words, the data units 530 are first sent to the sub-control units with instructions about what to do with the pulses 494 that comes after the data units 530. The master unit 266 may provide power to the sub-control units via the wires extending from the master unit to the sub-control units. The data units may include information about to which electrodes and which combinations of electrodes and pulse length, the sub-control unit should distribute the pulses 494 to when they arrive from the CPU of the master unit 266. All the sub-control units receive the data but they have different addresses so the master unit can address the data to the right sub control unit. If the data information has the wrong address for a sub-control unit then the sub-control unit does not read it. No data should be sent during the stimulation pulses and, preferably, the stimulation pulses to the sub-control units are generated from the master unit 266 that also controls the data flow. As indicated above, instead of using a serial data-bus with two wires, it is possible to also use three wires wherein two of the wires are used for power while the third wire is use to carry the stimulation pulses and that data can be sent via a suitable wireless technology. It is also possible to use two wires used to provide the power while the data is sent by wireless technology. It is also possible to use a one-wire data transmission such as sending data between the master unit and the sub-control unit in the positive or negative wire. The body suit can also have multiple master units so that, for example, one master unit stimulates an arm and the other master unit is used to stimulate the legs. The master unit can also have several power, data and pulse outputs circuits so that it drives several independent circuits such as running the front part of the suit independent from the back side of the suit or the upper part of the suit independent from the lower part of the suit.

Figure 15:
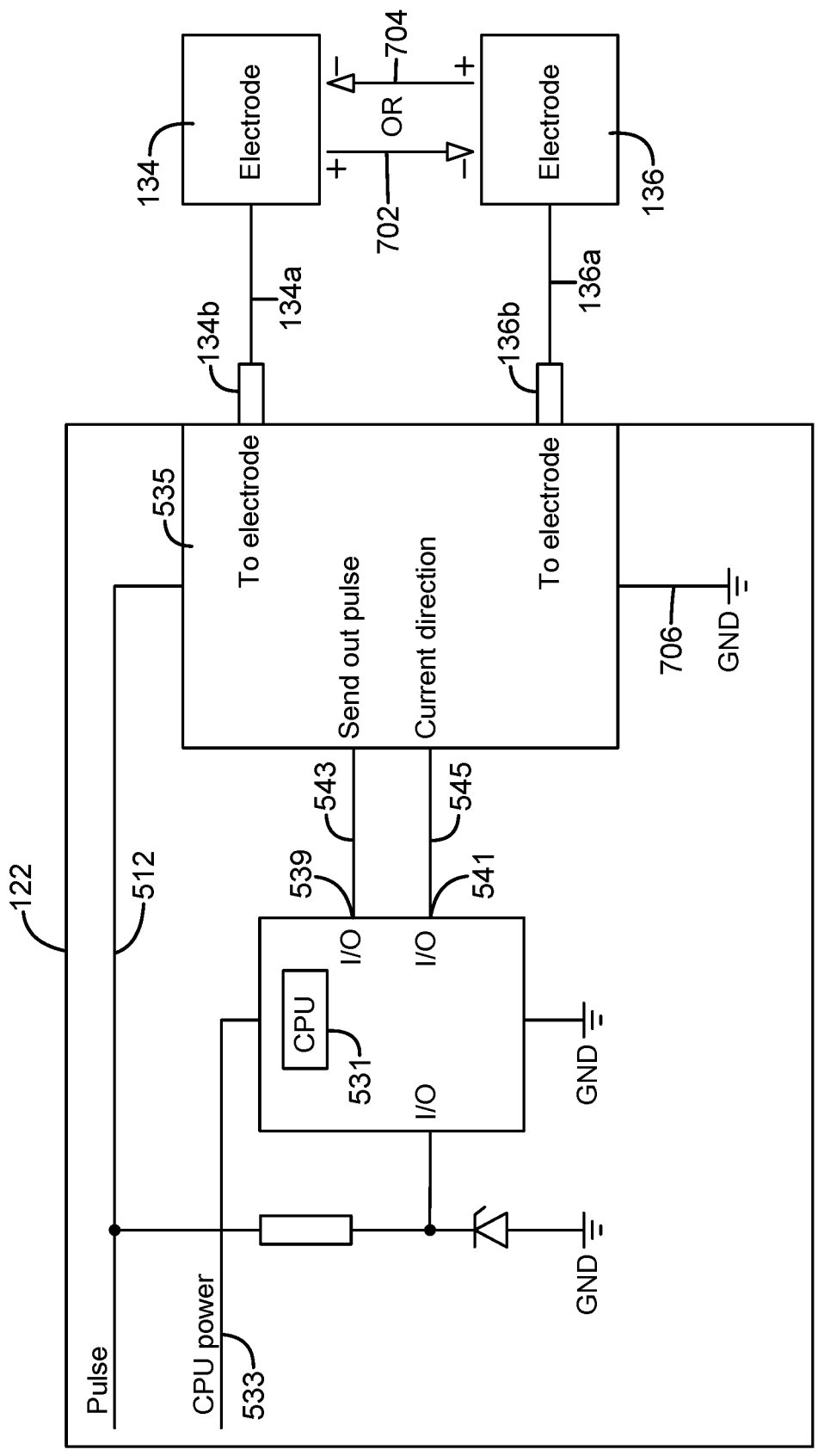
FIG. 15 is a detailed schematic view of a sub-control unit according to the present invention.

FIG. 15 is a schematic illustration of how the direction of the current between two electrodes via a muscle can be changed so that a positive pole is changed to a negative pole and vice versa. It may also be possible to intermittently switch the current flow so that the current first flows from an insertion or first end of the muscle to an origin or second opposite end of the muscle and then from the origin or second end to the insertion or first end i.e. the current goes back and forth through the muscle. It may also be possible run in one direction for more than one cycle before the direction is switched to the opposite direction. An important and surprising insight is that the switching of the direction of the current improves the effectiveness of the stimulation by reducing the build-up of natural resistance in the treated/stimulated muscle over time and reduces the risk of red irritations being created on the skin of the patient. It has been discovered that the muscles have a capacitor effect in the muscle, similar to a capacitor. Preferably, the CPU 531 of the sub-control unit 122 determines which current direction should be used based on instructions received from the master unit 266. It is possible to switch the direction during each stimulation pulse, such as after 50% of the pulse length the polarity is shifted or shifted several times during one pulse. It is possible to switch the direction after each stimulation pulse that is sent to the electrodes or numerous pulses may be sent, such as 10 pulses, before the direction of the current is switched and then, for example, send another 10 pulses before the direction is switched again. It is of course possible to run the current in the same direction through the muscles without switching the direction.

The CPU 531 of sub-control unit 122 receives power from the master unit 266 via power line 533 and also the pulse (see pulse input 782 in FIG. 16) so that the CPU knows that a pulse has arrived to the sub-control unit. With reference to FIG. 15, the unit 122 has an output unit 535 that receives the pulse signal 512 sent from the output 537 of the master unit 266. The output unit 535 has a ground 706. The pulse stimulation signal 512 from the master unit 266 is sent via arrangement 513 shown in FIG. 10. The CPU 531 of the sub-control unit 122 has an I/O unit 539 that sends instructions about when to send out pulses via line 543 to the output unit 535. More particularly, the unit 539 may send out either a "0" instruction or a "1" instruction wherein the "1" instruction that may represent that the output unit 535 leads out the stimulation output pulse for a certain time period to forward the incoming stimulation pulse 512 from the master unit 266 to the electrodes. The "0" instruction may represent that the output unit 535 is switched to a closed position to close the output function so that no stimulation pulse signal 512 can pass through the output unit 535. The CPU unit 531 also has an I/O unit 541 that sends out "0" or "1" instruction about which current direction to use via line 545 to the output unit 535. The "0" instruction may represent one direction while the "1" may represent the opposite current direction. If electrode 134 is the positive pole and electrode 136 is the negative pole then the current flows from output unit 535 to electrode 134 via wire 134*a* through the muscle and into electrode 136 and via wire 136*a* back to output unit 535 of sub-control unit 122 to ground (GND). The arrows 702 and 704 between the electrodes 134, 136 indicate that the direction of the current flow can be changed. As shown in FIG. 5, the sub-control unit 122 is not limited to just extensions 134*b*, 136*b* that are connected to electrodes 134*a*, 136*a*, respectively but preferably has at least 8 such extensions. It is also possible to create combinations so that, for example, electrodes 134 or 136 are combined with one or many other electrodes so that complex treatment patterns may be created by the CPU 531 with instructions from the CPU in the master unit 266.

Figure 16:
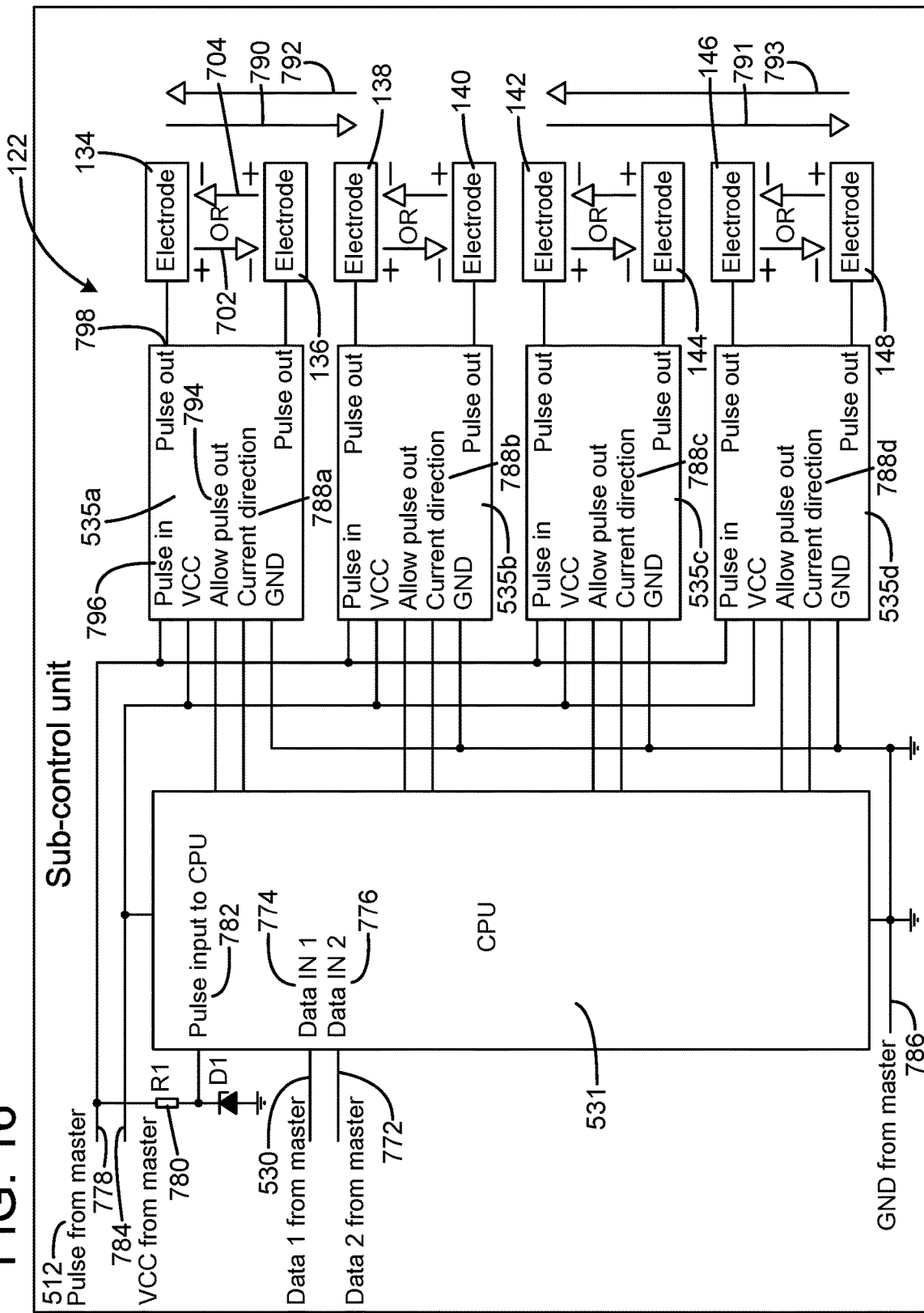
FIG. 16 is a detailed schematic view of a sub-control unit connected to electrodes according to the present invention.
Figure 17:
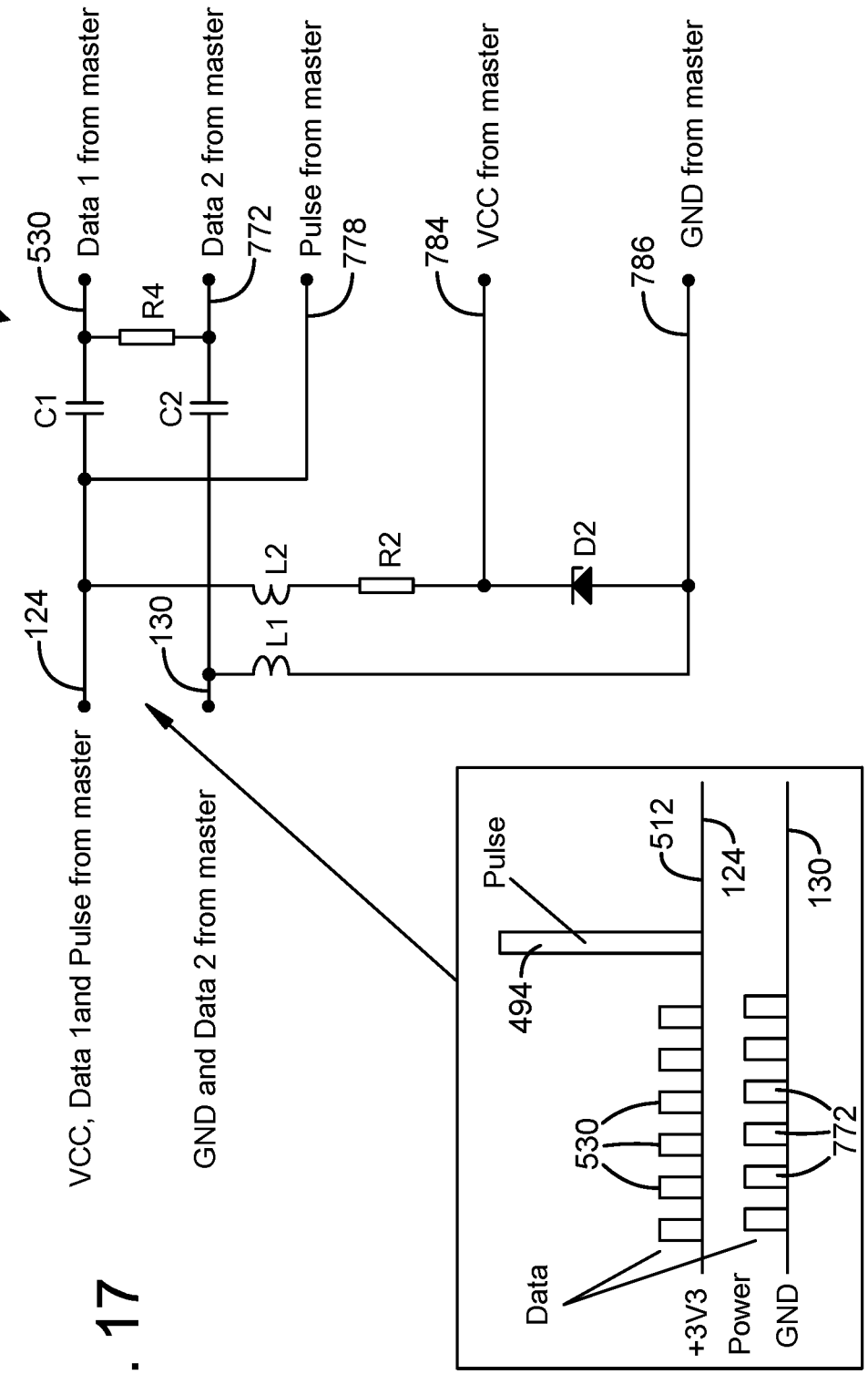
FIG. 17 is a schematic view of a distribution unit according to the present invention.

FIG. 17 illustrate how a distribution unit 770 can receive power, data and pulses and distributes signals to the CPU 531 and output units 535 of the sub-control units such as sub-control unit 122 (also shown in FIG. 15). In general, the serial data-bus information (i.e. power, data and pulses) that are eventually transmitted in, for example, the two wires 124, 130 are first split up or divided into five separate lines that are connected to the CPU and the output units of the sub-control unit. Preferably, the distribution unit 770 is part of the sub-control unit 122 and a part of the master unit 266 unit. FIG. 16 is similar to FIG. 15 but shows more details and includes 8 electrodes 134, 136, 138, 140, 142, 144, 146 and 148 instead of just 2 electrodes 134, 136 and four output units 535*a*, 535*b*, 535*c*, 535*d* instead of just the one output unit 535 shown in FIG. 15. In this system, the master unit 266 is communicating with the sub-control units and electrodes by using only two wires, such as wires 124 and 130 in FIG. 17, that are electrically connected to all the sub-control units in the bodysuit and other wire pairs going to the master unit 266. One wire, such as wire 124 in FIG. 17, could carry VCC power at, for example, +3.3V, data1 pulses 530 and the stimulation pulses 494 received from the master unit 266 to the sub-control units. The other wire, such as wire 130, could serve as ground (GND) and carry data2 pulses 772. The data 1 pulses 530 and data 2 pulses 772 relate to communication between the master unit and all the sub-control units. Other data bus constructions may also be used. The unit 770 separates data1 pulses 530 from VCC by unit C1 so that the data goes to a data input Data IN 1 774 of the CPU 531 (best shown in FIG. 16). Data2 pulses 772 are separated from GND by unit 770 by unit C2 to an input Data IN 2 776 of the CPU 531. The pulses 494 of stimulation signals 512 to the electrodes are sent in to the sub control unit when no data is sent. This pulse 494 is read by the CPU 531 at input 782 via resistor 780 and zener diode D1 (in FIG.

16) to a pulse input 782. This pulse 494 also goes to the 535*a*, 535*b*, 535*c* and 535*d* as pulse-in 796 and as pulse-out 798 to the electrodes when the sub-control unit sends out the pulses. The CPU 531 can keep the pulse length of the stimulation signal 512 the same or shorten it by activating the allow pulse-out 794 function. The same principle applies to all the other output units 535*b-d*.

The arrangement 770 in FIG. 17 provides a protection of the electronic components so that the high voltage pulse does not destroy any component that cannot withstand the high voltage. The unit 770 distributes a VCC power signal 784 (such as +3.3V) to the sub-control units 122 to provide power to the components of the sub-control unit 122 and ground via GND 786. The CPU controls the current direction of output units 535*a*, 535*b*, 535*c* and 535*d* regarding the current direction 788*a*, 788*b*, 788*c*, 788*d* of the electrodes and how to switch the polarity of the electrodes 134,136, 138,140,142,144,146 and 148 in FIG. 16 as illustrated by the arrows between the electrodes. Only arrows 790, 791, 792 and 793 illustrate that the electrode pair may also change so that, for example, electrode 134 is paired with electrode 138 instead of with electrode 136. It is to be understood, that the electrodes may be paired in any combination and that the electrode pairs 134 and 136 and electrode pairs 134 and 138 are merely examples. This means electrode 134 may, for example, be the positive pole while electrode 138 is the negative pole. The electrode 134 may be paired with any other electrode. It is important that the electrodes may change polarity in order to make it possible to pair any of the electrodes with one another since one electrode must be the positive pole and the paired electrode must be the negative pole. The change of polarity of the electrodes makes it possible to stimulate the muscles in new and different ways. This is not possible to do when the polarity of the electrodes is fixed.

The serial data 1 and 2 between the master unit and the sub-control unit include information about how the pulses should be sent out from the sub-control unit to the electrodes. When a stimulation pulse arrives to the sub-control unit via pulse input 778, the CPU 531 must first realize or be activated by the stimulation pulse that has arrived to the sub-control unit. This is determined by input 782. Then the CPU of the sub-control unit selects to which electrode pair the stimulation pulse should be sent to and the CPU sets the current direction and then the CPU allows the stimulation pulse to pass to pulse out on units 535*a*, 535*b*,535*c* or 535*d*. Preferably, the pulse length or duty cycle (such as 200 microseconds) of the stimulation pulse received from the master unit via line 778 should be slightly longer than the max pulse length (such as 175 microseconds) of the stimulation pulse that is sent from the output unit 535*a* to the electrode 134 and 136. The exact values of the pulse lengths are not important as long as the pulse length of the incoming pulse is slightly longer than the outgoing pulse to the electrodes. The sub-control unit knows the stimulation pulse length so that the sub-control unit sets the correct pulse length. The difference (such as 25 microseconds) in the pulse length enables the output unit 535*a* to receive the incoming stimulation pulse and send the stimulation pulse to the correct electrode and with correct length.

Figure 18:
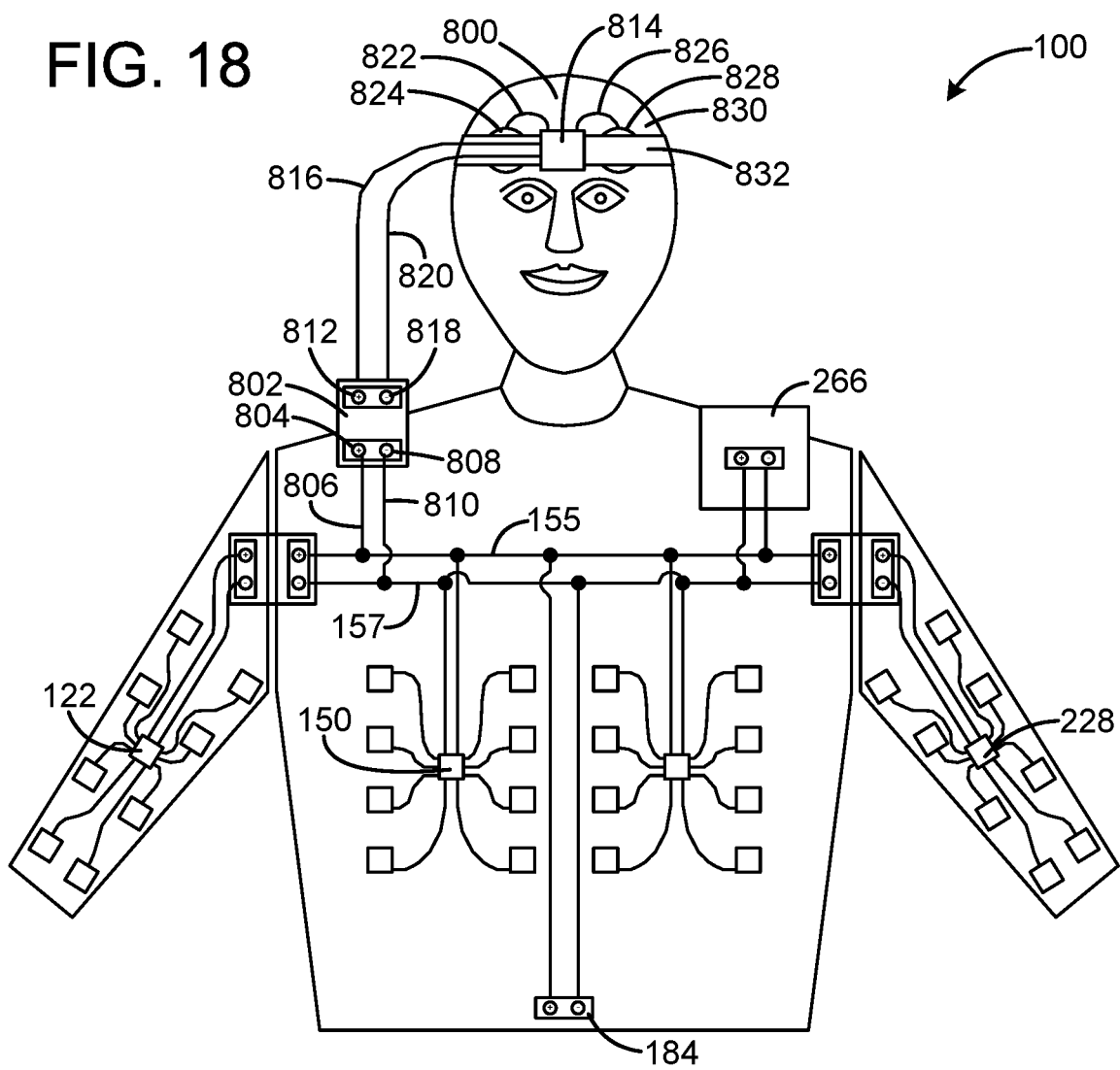
FIG. 18 is a schematic front view of a portion of the body suit shown in FIG. 4 including sub-control unit mounted on the head of the person wearing the body suit according to the present invention.

FIG. 18 is a schematic view of the body suit 100 reading the brain signals 800 of the patient who wears the body suit 100 so that the electrodes measures the weak voltage signals from the brain. Only the upper part of the body suit 100 is shown in FIG. 18 and the other portions of the body suit 100 are identical to the body suit shown in FIG. 4 that also includes all the reference numerals. The suit 100 has a sixth connector 802 that has a positive pole 804 electrically connected to wire 155 via an elastic and flexible wire 806 and a negative pole 808 electrically connected to wire 157 via an elastic and flexible wire 810. The sixth connector 802 has a positive pole 812 that is electrically connected to a seventh sub-control unit 814 via an elastic and flexible wire 816 and a negative pole 818 that is electrically connected to the sub-control unit 814 via an elastic and flexible wire 820. The sub-control unit 814 is different from the other sub-control units in that is does not have any muscle stimulation function but is used to receive information from the electrodes about the brain signal activity of the brain 800 and transmits this information via the serial data-bus to the master unit 266. The master unit 266 receives the information and determines which stimulation that should be activated. The sub-control unit 814 can provide input to the system so that the system can perceive with the help of these signals which body parts the person wearing the body suit wants to move. This is where the master unit 266 steps in to interpret the brain voltage signals (EEG signals) sensed by the electrodes inside the headband 832 or at the lower neck level or upper spinal cord to learn which muscles that must be activated to carry out the desired muscle movement such as moving an arm. The present invention is not limited to merely reading signals at the brain level. It is also possible to use the body suit to read the signals that the brain send at the lower neck level or upper spinal cord in order to read request for movements without requiring the patient wear a heatset or head-piece with electrodes. The body suit can be used to measure signals at upper neck muscles, jaw muscles, sternocleido mastoideos and stratetius muscles to read brain signals without needing a headset The master unit 266 may have a database that includes previously recorded and stored brain voltage wave patterns for various muscle movements so that when a certain brain voltage wave pattern is received, the master unit may first analyze the pattern of the incoming brain signals and then search its database to find the matching brain signals pattern that is then translated into which electrodes should be activated and in which order to carry out the desired muscle movement or stimulation such as the movement illustrated in FIG. 9. The sub-control unit 814 contains a CPU that saves and analyzes the incoming data from the electrodes 824, 828 and send data to master unit 266 that determine which electrodes should be activated in the suit. It should be understood that sub-control unit 814 sends out data via the serial data-bus to the master unit 266 when the master unit asks for data.

Similar to the sub-control units in the modules, the sub-control unit 814 is electrically connected via a wire 822 to an electrode 824 and via a wire 826 to another electrode 828. It should be understood that more than two wires may be used between the sub-control unit 814 and the connector 802. The electrodes are preferably urged against the head 830 by an elastic headband 832. FIG. 18 illustrates only two electrodes but many more electrodes may be used as required to monitor the brain voltage signals of the brain 800 to determine which muscles the person is thinking about using. The body suit may be used to read signals at sternocleidomastoid muscle, temporalis muscle, masseter muscle, trapezius muscle, suboccipital muscles, cervical spinal erector muscles. The body can be used to conduct measurement of key muscles in head and neck.

EMG measurements in a first muscle can be recorded and stored. The recording of EMG-activation can be paired to activation of any other muscle in the patient/user by using the electrodes in the suit. Activation of any other muscle, through the suit electrodes, can be connected to activate of the first muscle. For example, the user could clench the teeth and so forth activate the masseter muscle. The EMG signal from masseter could be the starting signal to activate contraction of knee extensor muscles. A patient/user with tetraparesis, after cervical spinal cord injury, could regain the ability to stand through activation of jaw closing muscles. Another example is that the shrugging of shoulders leads to activation of the trapezius muscle, measured by EMG-electrodes in the bodysuit. Activation of trapezius could be paired to activation of the arm-lifting and elbow-flexing muscles. In this example, the shrugging of the shoulder could lead to the user giving someone a hug.

FIG. 19 is a schematic illustration of the master unit 266 that, preferably, includes a disposable or re-chargeable battery 850, such as 6-10 volts (or higher), to electrically drive the master unit 266 and all sub-control units. Preferably, the battery cannot be charged while in the master unit and in the suit to prevent any undesirable voltage going into the bodysuit 100 during charging. An external battery charger should be used. The battery 850 is electrically connected to the power unit 852 that provides the power to the central processing unit (CPU) 854, display 860 and all the master unit circuitry 513 (also shown in FIG. 10) and all sub-control units. The power module or unit 852 also has a step-up voltage circuit 856 that steps up the voltage of the stimulation pulse voltage 511, that uses to generate stimulation pulse 512 sent to the sub-control unit to, for example, about 20V or 40V wherein the power voltage to the arrangement circuit 513 and CPU may, for example, be 3.3V or 5V. In other words, the circuit 856 increases the voltage of the battery such as 3-10V to about 20-40V. The exact voltage used in the stimulation pulse 512 is determined by the CPU 854 and its software. The master unit 266 also has a safety circuit module in hardware 858 that makes sure no pulse length in the stimulation pulse is longer than a predetermined maximum time period. The reference to CPU in arrangement 513 in FIG. 10 means there is an electrical connection to the CPU 854 that controls the input/output to receives information from and send information to the arrangement 513. The master unit has a user interface unit 860 that is an interface so that the therapist can set, see and change parameters and programs of the master unit and also receive the data from the master unit collected during earlier stimulating runs. The display unit 860 may include a display window 862, switches as start/stop 864 that starts or stops the running of the stimulation program such as a stimulation program and makes it possible to select and change stimulation programs and pause the run of the stimulation program. The unit 860 has a buzzer 866 that provides sound/warning signals and LED diodes 868 as indicators. The master unit 266 also has a communication module 870 for Bluetooth, Wi-fi and USB data connections in order to communicate with the sub-control units in the bodysuit 100 and with computers as PC, pad or phones and with the Internet and cloud services. The master unit 266 has an interface 872 that connects all the wiring that goes to the sub-control units to send five types of signals including power, positive pole, negative pole, superposed data and stimulation pulses equivalent to FIG. 17 (see ref. no. 770).

Figure 20:
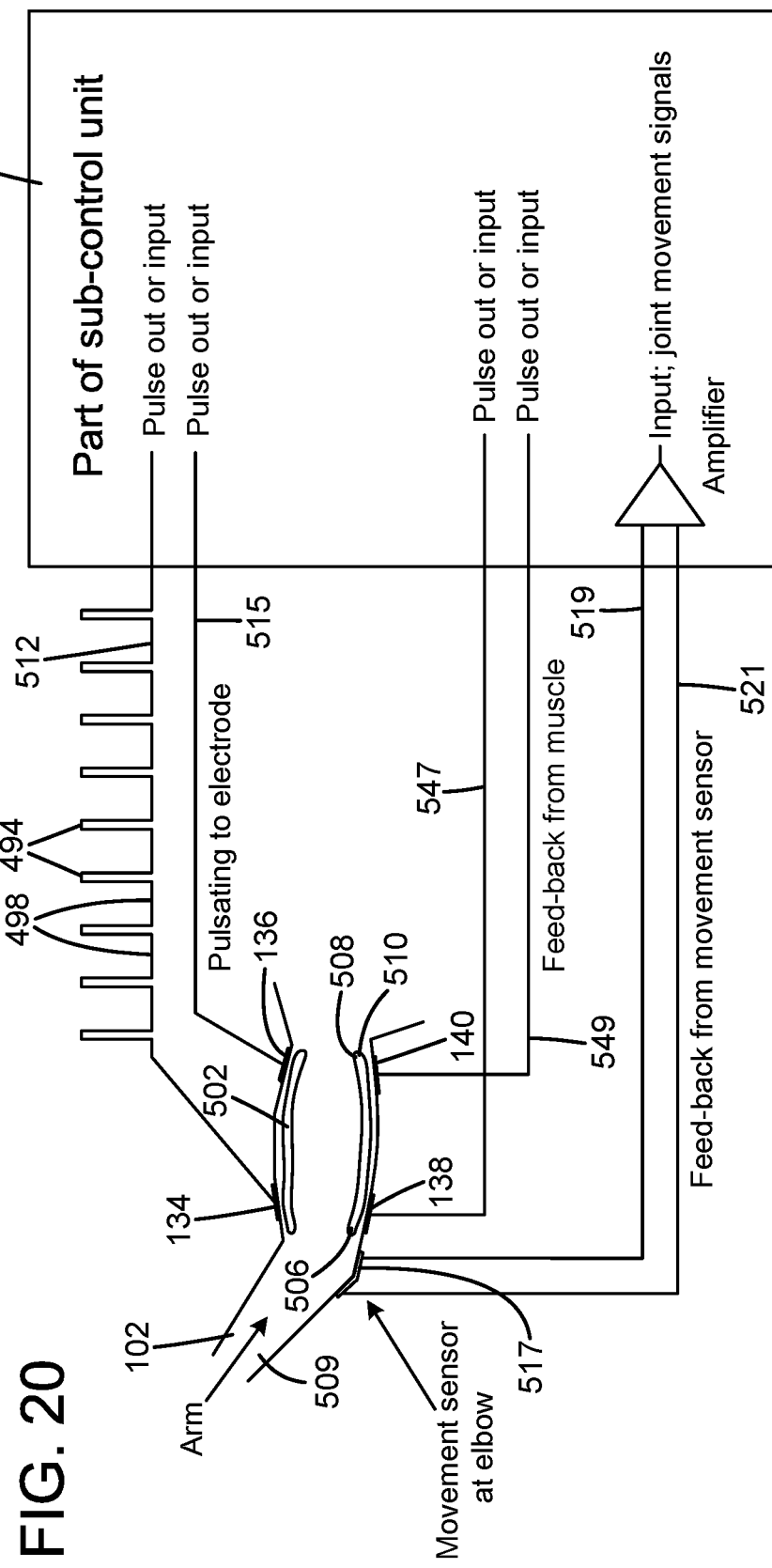
FIG. 20 is a schematic view of sub-control unit shown in FIG. 9 connected to movement sensors according to the present invention.

FIG. 20 is substantially similar to FIG. 9 but includes a movement sensor 517 that registers movement of the arm 509. The movement sensors may be placed on any part of the body suit 100 where measurement of movements is desired, the placement of the sensor 517 on the elbow of the arm 509 is merely an illustrative example. Information about the movement sensed by the sensor 517 is sent to the sub-control unit 122 via wires 519, 521 and provides feedback to the sub-control unit 122 regarding the effect of stimulation signal 512 on the body movement when the signal 512 is strong enough to cause muscle 502 to contract in order to move the arm 509 or when the user of the body-suit can move the arm. In this way, the sub-control unit receives information about whether the arm has moved and how much it has been moved. With the movement sensors the system can obtain information about movement even micro-movements created with the stimulation pulses. This information is also be sent to the master unit 266 so that the parameters of the stimulation signal 512 can be adjusted accordingly. It is also possible to merely read micro-movements at the muscle level to determine whether the "sweet-spot" has been reached i.e. the correct stimulation of the muscle that triggers the response from the spinal cord without causing a physical movement of, for example, the arm.

FIG. 21 is a schematic view of a frontside of a garment of an elastic and tight body suit 1000 of the present invention. The body suit 1000 is substantially similar to body suit 100 shown in FIGS. 4 and 18 except that body suit 1000 also includes a right-hand glove module 1002, left-hand glove module 1004, right sock module 1006 and a left sock module 1008. The detailed description of body suit 100 also applies to body suit 1000. For clarity, only the differences between body suit 1000 and body suit 100 are here described. One important feature of body suit 1000 is that it enables the patient wearing the suit to move the hands, fingers, feet and toes by reading brain signals and by electrically relaxing and stimulating muscles, as described in detail above. The sub-control unit 122 of right arm module 102 has an elastic and flexible wire 1010 electrically connected to a positive pole 1012 of a right-hand connector 1014 and an elastic and flexible wire 1016 electrically connected to a negative pole 1018 of the right-hand connector 1014. Similar to the other connectors described in detail above, right-hand connector 1014 electrically connects the right-hand glove module 1002 to the right arm module 102.

Right-hand glove module 1002 has a right-hand sub-control unit 1020 that is electrically connected to electrodes 1022, 1024 and 1026 via elastic and flexible wires 1022a, 1024a and 1026a to relax and stimulate muscles in the hand 1028, as described in detail above. The sub-control unit 1020 is electrically connected to a positive pole 1030 and to a negative pole 1032. The sub-control unit is here shown with 3 electrodes but it can have more or fewer electrodes. This applies to all the sub-control units of FIG. 21.

The sub-control unit 228 of left arm module 106 has an elastic and flexible wire 1034 electrically connected to a positive pole 1036 of a left-hand connector 1038 and an elastic and flexible wire 1040 electrically connected to a negative pole 1042 of the left-hand connector 1038. The left-hand connector 1038 electrically connects the left-hand glove module 1004 to the left arm module 106. Left-hand glove module 1004 has a left-hand sub-control unit 1044 that is electrically connected to electrodes 1046, 1048 and 1050 via elastic and flexible wires 1046a, 1048a and 1050a to relax and stimulate muscles in the hand 1052, as described in detail above. The sub-control unit 1044 is electrically connected to a positive pole 1054 and to a negative pole 1056.

The sub-control unit 294 of right leg module 110 has an elastic and flexible wire 1058 electrically connected to a positive pole 1060 of a right-foot connector 1062 and an elastic and flexible wire 1064 electrically connected to a negative pole 1066 of the right-foot connector 1062. The right-foot connector 1062 electrically connects the right-sock module 1006 to the right leg module 110. Right sock module 1006 has a right-foot sub-control unit 1068 that is electrically connected to electrodes 1070, 1072, 1074 and 1076 via elastic and flexible wires 1070a, 1072a, 1074a and 1076a to relax and stimulate muscles in the right foot 1078, as described in detail above. The sub-control unit 1068 is electrically connected to a positive pole 1080 and to a negative pole 1082.

The sub-control unit 320 of left leg module 112 has an elastic and flexible wire 1084 electrically connected to a positive pole 1086 of a left-foot connector 1088 and an elastic and flexible wire 1090 electrically connected to a negative pole 1092 of the left-foot connector 1088. The left-foot connector 1088 electrically connects the left sock module 1008 to the left leg module 112. Left-sock module 1008 has a left-foot sub-control unit 1094 that is electrically connected to electrodes 1096, 1098, 1100 and 1102 via elastic and flexible wires 1096a, 1098a, 1100a and 1102a to relax and stimulate muscles in the right foot 1104, as described in detail above. The sub-control unit 1094 is electrically connected to a positive pole 1106 and to a negative pole 1108. It is thus also possible to measure movements and voltage signals from the feet and hands of the patient wearing the body suit.

Because the body suit 1000 of the present invention has sub-control units it is possible to extend the stimulation to the hands and feet by activating electrodes on the glove and sock modules. It is also possible to remove one module such as arm module 102 and electrically connect connector 128 directly to right-hand connector 1014 so that the master unit 266 can communicate with the sub-control unit 1020 to control the electrodes connected to the sub-control unit 1020. This principle of removal of a module applies to all the other modules i.e. that one module can be removed and then the connectors can be directly connected to one another.

In operation, it is possible to ramp up or gradually increase the pulse length, voltage level of the stimulation pulse and the current level such as in the beginning of the stimulation treatment to make the treatment more comfortable to the patient. In other word, the treatment starts with a mild stimulation that is gradually increased to make the stimulation signal more powerful when the patient has become used to feeling the stimulation signal. When necessary it is also possible to ramp down the pulse length, voltage level of the stimulation pulse and the current such as at the end of the treatment or when the stimulation pulse is too strong or powerful to the patient (i.e. when the stimulation signal causes undesirable movement of, for example, an arm). More particularly, when the arrangement 513 is in the current mode, it is effective to gradually increase the current as set by the current limits in signal 759 assuming that the voltage of pulse power 511 is high enough for the current at the stop limit current 518. The ramping up period may be between 5-10 minutes before the full treatment current is reached. The treatment period may be 40-60 minutes. The treatment period may be longer or shorter. When the treatment period is over, it is possible to ramp down i.e. gradually reduce the current for 5-10 minutes by gradually lowering the current limits in signal 759 to make it comfortable to the patient. The pulse length may also be ramped up in a similar way so if the pulse length is 175 microseconds the first pulse may be 30-50 microseconds long and this is gradually increased until the full pulse length is reached in 5-10 minutes. The pulse length can also be ramped down at the end of the treatment in a similar way over 5-10 minutes. The ramping up and down of the pulse length applies to both the voltage mode and the current mode. It is less effective to raise the voltage of the pulse power 511 when the arrangement 513 is in the current mode because the arrangement 513 is then self-regulating and the comparator 756 sets the current as the result of the current limit level provided in signal 759. The only voltage requirement, when in the current mode, is that it must be high enough to accomplish the stop current 518. When the current of the stimulation signal 512 is ramped up this is reflected in the pulse current value signal 752 (see FIG. 10) that goes to the CPU of the master unit 266 so that the CPU receives the feedback that the current is actually gradually being increased as a result of raising in the current limit in signal 759 that is also sent by the CPU of the master unit 266. Because the fluctuations between current start 516 and current stop 518 are shorter (in nanoseconds range) than the pulse length 495, the voltage value in signal 752 represents an average of the voltage or the equivalent current that fluctuates between the current start 516 and current stop 518. In this way, the pulse current average value signal 752 acts as a feedback signal to the change of the current level in signal 759. The corresponding current value in signal 752 is particularly important when the arrangement 513 is in the voltage mode because then the value of the actual current flowing in one pulse through the muscle is unknown or at least difficult to control, as shown in FIG. 11C. When in the voltage mode and if the corresponding average current in signal 752 is too high then the CPU of the master unit 266 can lower the voltage of the pulse power 511. Similarly, when the average current is too low, as reported in signal 752, then the CPU can increase the voltage of pulse power 511 when in the voltage mode until the desired current is reached although it is difficult to know the exact current that flows through the muscle in each pulse, as shown in FIG. 11C.

When in the current mode and if the current in stimulation signal 512 is too high then movement sensor 517 (see FIG. 20) can sense a movement or contraction of a muscle, for example, the arm 509 as reporting in signals 519, 521 going to the sub-control unit 122 and the sub-control unit 122 forwards the movement information to the master unit 266 that lowers the current limits in signal 759 going to the comparator 756 of circuit U1 when the arrangement 513 is in the current mode (see FIG. 10) the sub-control unit can also shorten the pulse length to lower the stimulation. When the current is too high and the arrangement 513 is in the current mode (signal 750 is in "1" mode) then it may also be effective for the CPU of the master unit 266 to shorten the duty cycle or pulse length 495 of each pulse 494 of the stimulation signal 512 or lowering the current limit level 759. It is also possible for the CPU of the master unit 266 to shorten the pulse length when the arrangement 513 is in the voltage mode although the current that flows through the muscle includes the peak 521 (see FIG. 11C) in the beginning of the pulse so a slight shortening of the pulse length does not remove the peak 521 so the stimulation signal may still be uncomfortable to the patient wearing the body suit even when the pulse length has been slightly shortened such as from 175 microseconds to 100 microseconds since the current peak 521 occurs in the beginning of the pulse 494. The current mode does not have this drawback because the current only fluctuates between the current start 516 and current stop 518 (see FIG. 11B).

It is also possible to measure the difference between the voltage signals from electrodes 138, 140 that are mounted on the antagonist muscle 508. This voltage difference is amplified by amplifier 127 (see FIG. 9) and stored in the sub-control unit 122. The sub-control unit 122 may then at time intervals report the voltage differences to the master unit 266 so that the master unit can determine whether the parameters of the stimulation signal 512 of muscle 502 should be changed. If the voltage difference is high this means the muscle 508 is not sufficiently relaxed and the stimulation of muscle 502 should increase by raising the parameters of the signal 512 such as raising the current when the arrangement 513 is in the current mode or raising the voltage when the arrangement 513 is in the voltage mode.

It is also possible to connect more than one master unit to the bodysuit so that one master unit runs a first program in a first module of the bodysuit and a second master unit runs a second program in a second module wherein the second program is different from the first program. In this way, the stimulation pulses, frequencies etc. associated with the first program are independent of the stimulation pulses, frequencies associated with the second program. Many master units can be connected to the connectors of the bodysuit. If only the arm module is used then the master unit 266 can be connected at connector 128 or connector 194. Preferably, the master unit is or the master units are connectable to any of the connectors on the body suit.

FIGS. 22A-22C illustrate the drawbacks of using the voltage mode. It is to be understood that the resistance values of the electrodes and muscles are merely illustrative example to explain the principles of the present invention. Other resistance values may also be used. With reference to FIG. 22A and as explained in detail regarding FIGS. 11C-11D, the initial current (when the arrangement 513 is in the voltage mode) that runs through the muscle reaches a peak value 521 during the pulse flank that may, for example, be about 25 mA that rapidly decreases to the working current level 525 that may, for example, be about 3 mA when the internal resistance in the electrodes is about 100 Ohm, the muscle resistance is about 6500 Ohm and the pulse voltage is 20V. In this example, about 0.3V is lost in each electrode. The internal resistance in each electrode could increase to about 1000 Ohm or any value higher substantially than 1000 Ohm. When the resistance is 1000 Ohm, the current is 20V/8500 Ohm=2.35 mA which is the maximum current going through the muscle. Because the muscle is like a capacitor the maximum charging current is not more than 10 mA (20V/2000 Ohm=10 mA because the capacitance is between the electrodes through the muscle. The level of the current maximum after the peak 521 is dependent on the total resistance (i.e. the resistance of the electrodes plus muscle resistance). In the above example, the resistance is about 6500 Ohm in the muscle and 1000 Ohm in each electrode so that the maximum current is then 2.35 mA (20V/8500 Ohm=2.35 mA) as shown by curve 523 in FIG. 22A.

FIG. 22B illustrates the voltage across the electrode when the electrodes have an internal resistance of 100 Ohm each and how the voltage gradually increases to a voltage level 527 such as 19.4V which is lower than the voltage 20V. This is because the voltage drop in the electrodes is 0.3V in each electrode (3 mA×100 Ohm=0.3V) of the pulses 494 of the stimulation signal 512. The reduction of the current peak increases the voltage drop at the electrodes. FIG. 22C illustrates the muscle and electrodes with a resistance of 100 Ohm each when the voltage mode is used. If the peak current is 25 mA (charging the capacitance) and each electrode 134, 136 has an electrode resistance of 100 Ohm then 2.5V of the voltage is lost at each electrode 134, 136 during the peak top so the voltage is 15V between electrodes and at the muscle, as shown in FIG. 22B. When the current decreases during the pulse the voltage increases between electrodes and over the muscle 502, as illustrated by FIG. 22B. At a current level of 3 mA, about 0.3V is lost at each electrode 134, 136 when the resistance of each electrode is 100 Ohm which explains why the voltage 527 across the muscle 502 only reaches 19.4V in FIG. 22B. If the total resistance through the muscle 502 is about 6500 Ohm and the electrodes 134, 136 each has a resistance of 1000 Ohm each then there is a total resistance of 8500 Ohm in the circuit. The resulting maximum current, when voltage the pulses 494 is at 20V and the total resistance is 8500 Ohm, is 2.35 mA as shown by curve 523 in FIG. 22A and illustrated in FIG. 22D. FIG. 22D is identical to FIG. 22C except that the resistance of electrodes 134, 136 has increased from 100 Ohm to 1000 Ohm. Again, because the muscle is like a capacitor the charging current is maximum 10 mA when the electrodes have a resistance of 1000 Ohm each (20V pulse/electrode resistance 2000 Ohm=10 mA and this because there is capacitance between the electrodes through the muscle). FIGS. 22A and 22B thus illustrate the drawbacks of using the voltage mode because the current cannot be controlled as it can when the arrangement 513 is in the current mode.

Figure 23:
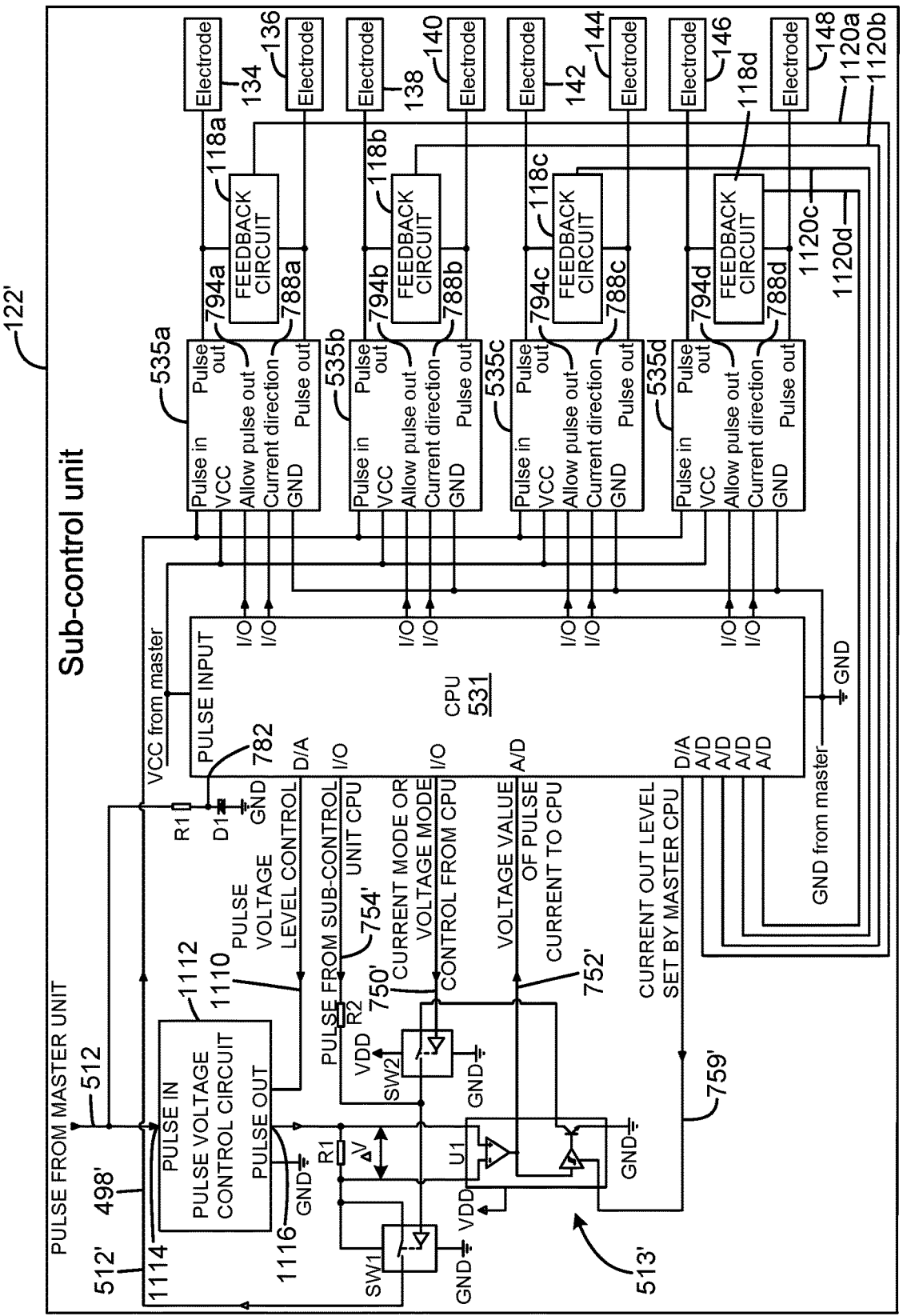
FIG. 23 is a schematic illustration of a modified sub-control unit of the present invention.

Another very important feature of the present invention is that the arrangement 513 (shown in FIG. 10) may be included in each sub-control unit such as sub-control unit 122 shown in FIG. 23. This signals 750, 754 and 759 come from the CPU of the sub-control unit instead of the CPU of the master unit. Preferably, the CPU of the sub-control units receive instructions from the CPU of the master unit about how the signals 750, 754 and 759 should be adjusted or set. The inclusion of the arrangement 513 at each sub-control unit makes it possible to run a first current at a first sub-control unit that is different from a second current at a second sub-control unit because the signal 759 at each sub-control unit sets the current limits as explained in detail above regarding FIG. 10. Additionally, the CPU of each sub-control unit can also set the pulse length via switch SW1, as explained in detail above.

It is possible to add a volt regulating circuit in the sub-control units so that the sub-control units may adjust (lower) the voltage of the pulse 512 that is received from the master unit. For example, when the arrangement is in the voltage mode, the sub-control unit can set a maximum level of the pulse voltage going to units 535a,535b,535c and 535d through the switch SW1. When the arrangement is in the current mode the voltage is set to the maximum value and the current is set by the arrangement that in turn affects the voltage of the stimulation signal so that the current is constant, as explained in connection with FIG. 10. All the information about what the sub-control unit should do is received as instructions from the master unit that in turn receives input information from the therapist that sets the stimulation pattern for the patient from a PC stimulation software program that sends instructions to the master unit.

FIG. 23 shows a modified sub-control unit 122' that includes an arrangement 513' that is substantially similar to the arrangement 513 (shown FIG. 10) so that the unit 122' can adjust (lower) the voltage, the pulse length and the current (when in the current mode). More particularly, stimulation pulse signal 512 arrives from the master unit 266 from switch SW1 shown in FIG. 24. The CPU 531 receives the stimulation signal 512 at pulse input 782. The CPU 531 is electrically connected to the output units 535a, 535b, 535c, 535d. The details of the output units are described in connection with FIG. 16 and apply to the output units in FIG. 23 also. The CPU 531 may keep or lower the voltage of the stimulation pulse signal 512 by sending a pulse voltage level control signal 1110 to a pulse voltage control circuit 1112 so that the voltage of the stimulation pulse signal 512 at pulse in 1114 remains the same or is lowered at pulse out 1116. For example, the circuit 1112 can lower the voltage of the stimulation signal from, for example, 60V to another voltage value such as 20V. The circuit 1112 can also keep the voltage of the stimulation signal 512 unchanged. As described in detail in FIG. 10, it is not important change the voltage when the arrangement 513' is in the current mode.

The CPU 531 may send a pulse control signal 754' to switch the switch SW1 between an open position and a closed position in the same way as signal 754 described in detail in FIG. 10 and it can also be switched to be on all the time because it is a pulse that comes from the master unit. In this way, the CPU 531 can shorten the pulse length 495 of stimulation signal 512 so that stimulation signal 512' leaving the switch SW1 has a shorter pulse length 498'. The switch SW1 can also keep the pulse length the same i.e. the same as the pulse length of stimulation signal 512 by activating the switch to be on all the time. The output units 535a, 535b, 535c, 535d receives the stimulation signal 512' and can keep the pulse length the same or shorten the pulse length received from the CPU further by activating allow pulse-out functions 794a. 794b, 794c and 794d, respectively, as described in FIG. 16. The CPU 531 can switch the arrangement 513' between a current mode and voltage mode by sending a control signal 750' to switch SW2, as described in FIG. 10. The CPU 531 can set the current limit by sending the signal 759' to the comparator 756' and a feedback signal 752' is sent back to CPU 531 to inform the CPU 531 about the current level. All the principles that apply to arrangement 513 also apply to arrangement 513' and are therefore not described here.

The output units 535a-d are electrically connected to electrodes 134-148. The details are shown in FIG. 16 and all the details of FIG. 16 also apply to FIG. 23 although some details have been omitted from FIG. 23 for clarity. The unit 535a-d are electrically connected to feedback circuits 1118a, 1118b, 1118c and 1118d that measure EMG signals i.e. the natural very small voltage signals from the muscles, as described in FIG. 9. Preferably, each feedback circuit includes a switch and amplifier to switch the amplifier in and out that measures the natural voltage signals from the muscles. The circuits 1118a-d send feedback signals 1120a, 1120b, 1120c and 1120d to the CPU 531 so the CPU can determine whether to change the voltage, pulse length or current of the stimulation signal 512'.

Figure 24:
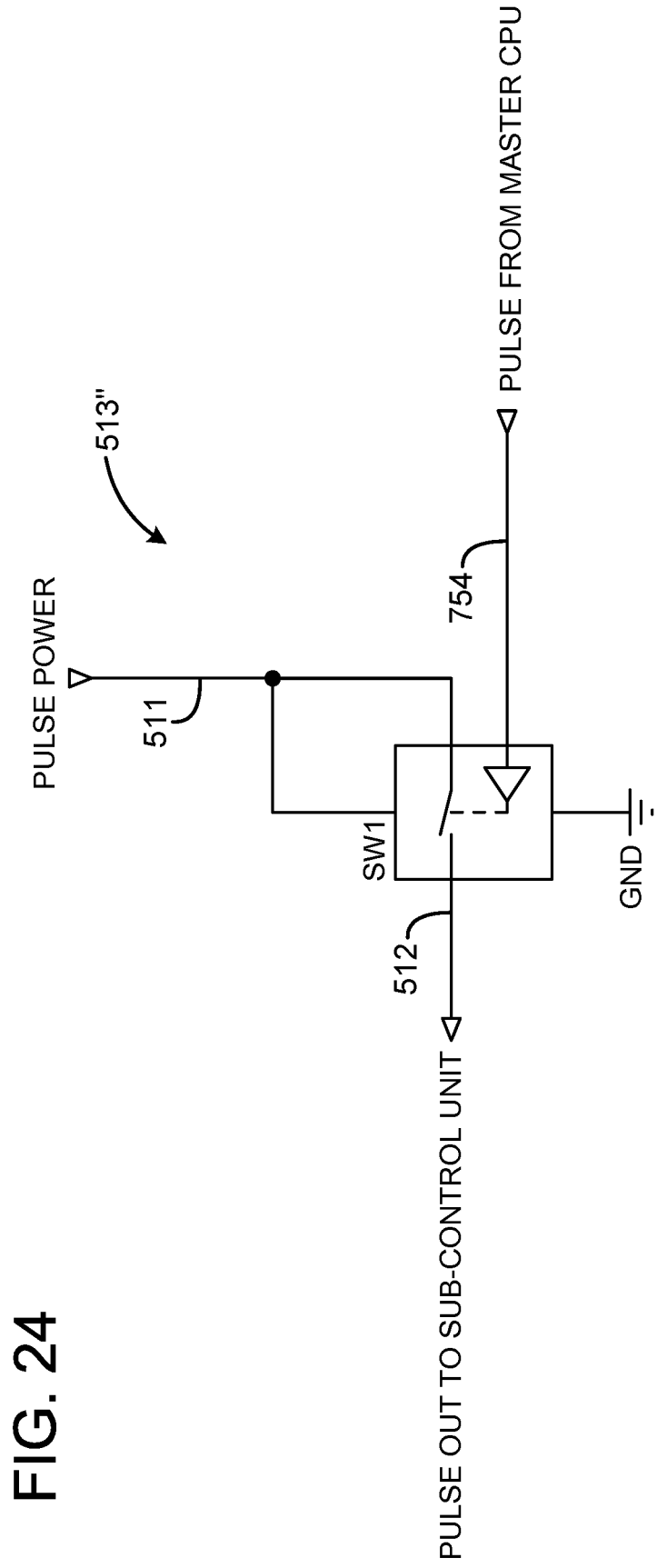
FIG. 24 is a schematic illustration of a modified portion of the master unit of the present invention.

FIG. 24 shows a simplified switch arrangement 513" of the master unit that can be used when the sub-control units include the arrangement 513'. In other words, the master unit can be simplified to merely send out stimulation pulses. The main function of arrangement 513" is to create the pulses of stimulation signal 512 from pulse power 511. For example, the arrangement 513" does not include the circuitry U1 or a switch SW2 to switch the arrangement between a current mode and a voltage mode. The arrangement 513" is always in the voltage mode and creates stimulation pulses 512 by opening and closing switch SW1, as described in connection with FIG. 10. Preferably, the master unit 266 still send out the pulsating stimulation signal 512 to the sub-control units for safety reason. If each sub-control unit would generate the stimulation voltage such as 40V the risk increases that something could go wrong which is very uncomfortable to the user. It is safer to have the master unit generate the stimulation voltage because it has separate hardware that makes such the voltage does not exceed certain preset limits. The master unit also has hardware that controls the pulse length to make sure it does not exceed a preset limit. This provides better safety compared to generating the high voltage signal in each sub-control unit.

Preferably, the voltage of signal 512 is higher than what is needed to stimulate the muscles because the circuit 1112 at each sub-control unit can lower the voltage to a desired level. In this way, it is possible to use a first voltage level at a first sub-control unit and a second voltage level at a second sub-control unit that is different from the first voltage level. However, the master unit sets the maximum pulse length and the maximum voltage in the stimulation signal and the local CPU at the sub-control unit can only keep the same values or lower the voltage or shorten the pulse length. Additionally, the CPU of the sub-control unit can set the current limit i.e. it can increase or decrease the current as desired as long as there is sufficient voltage in the stimulation signal from the master unit. Because each output unit has its own allow pulse out function, it is possible to use a first pulse length to the first pair of electrodes (i.e. electrodes 134, 136) and a second different pulse length to the second pair of electrodes (i.e. electrodes 138, 140) because the allow pulse out function can be set at different values for each output unit 535. If, for example, the pulse length of the stimulation pulse 512 is 200 microseconds, the pulse length can first be shortened at switch SW1 to, for example, 180 microseconds and then further shortened to, for example, 175 microseconds by using the allow pulse-out 794 function of the output unit, Each pulse in the stimulation signal 512 is sent to all sub-control units so that pulse 1 is used by sub-control units 1 and 3 while the second pulse is used by sub-control unit 2 etc. This means that sub-control unit 2 does not send out pulse 1 to the electrodes that the master unit selected by serial data communication to the sub-control unit.

The master unit sends data to all the sub-control unit and to each one when the sub-control units have a separate address. The sub-control units receive information about to which electrode or electrodes should receive the stimulation signal and in which order. For example, sub-control units 1 and 3 may be instructed to simultaneously send pulse 1 to electrodes and sub-control unit 2 may send out pulse 2 to its electrodes according to stimulation 1 of its list of stimulation pulses that are to be sent to the electrodes. This principle applies to all the sub-control units and all the sub-control units receive instructions about which pulse they should send out according to the list of stimulations that the master unit has sent them. If sub-control unit 1 uses pulse 1 and 2 as the first stimulation pulse signal and sub-control unit 2 uses pulse 3 and 4 to send out pulses while sub-control unit 3 uses pulse 5 and 6 to send out pulses and when there are only 3 sub-control unit in use then the 7 pulse is sent out by sub-control unit 1 again Each sub-control unit are connected with a plurality of electrodes so it sends out the stimulation pulses according to the instructions received from the master unit.

It is also possible for several sub-control units to simultaneously send out stimulation signals to the electrodes because all the sub-control unit receive the stimulation signals from the master unit. It is also possible for the master unit to vary the pulse length of each pulse in the stimulation signal so that pulse 1 is, for example, 200 microseconds while the second pulse is, for example, 175 microseconds and the third pulse is, for example, 180 microseconds. It is also possible to change the voltage level for each pulse in the same way. This would primarily be used when certain nodes lack the arrangement 513, the allow pulse-out 794 function and the ability to locally control the pulse length.

It is also possible to utilize multi-programs in the body-suit that include a mild muscle contraction program and then use a moisturizing and/or conductive cream/gel to be applied locally on the skin where muscle contractions take place just before stimulation signals are sent to start the treatment of the muscles/nerves.

A suitable frequency range of the stimulation signal may be in a range of 1 Hz to 120 Hz that covers most excitatory and inhibitory intervention needs. The lower end of the frequency range would be useful for testing and palpated or automated intensity adjustments. It is also an important feature of the present invention to be able to use different frequencies in different channels for adapting to different requirements in individual lesion profiles.

It is also possible to stimulate skin afferents although the size and sensitivity ranges are very broad ranging from fast group II myelinated to very slow group IV unmyelinated and conduction speed from approx. 1 to 70 m/s wherein the speed is proportionally sensitive to the artificial stimuli.

As mentioned above, strong stimulation for inducing muscle contractions can be limited when using dry electrodes because most spinal cord injured patients also lose their ability to sweat (lesion effects also the autonomous neural system) and then the electrical contact resistance cannot adapt with delivered moisture. It is therefore particularly important that the present invention enables the control and adjustments of voltage, current and pulse length etc. to adjust the stimulation signals to the conditions of the skin and patient.

It has been realized that the stimulation of many locations in the body such as muscles and nerves by using the body suit of the present invention increases the release of opioid receptors so that multi-focal stimulation reduces pain in general and could be a method for reducing the need for patients to take pain killers such as opioid pills.

Figure 25:
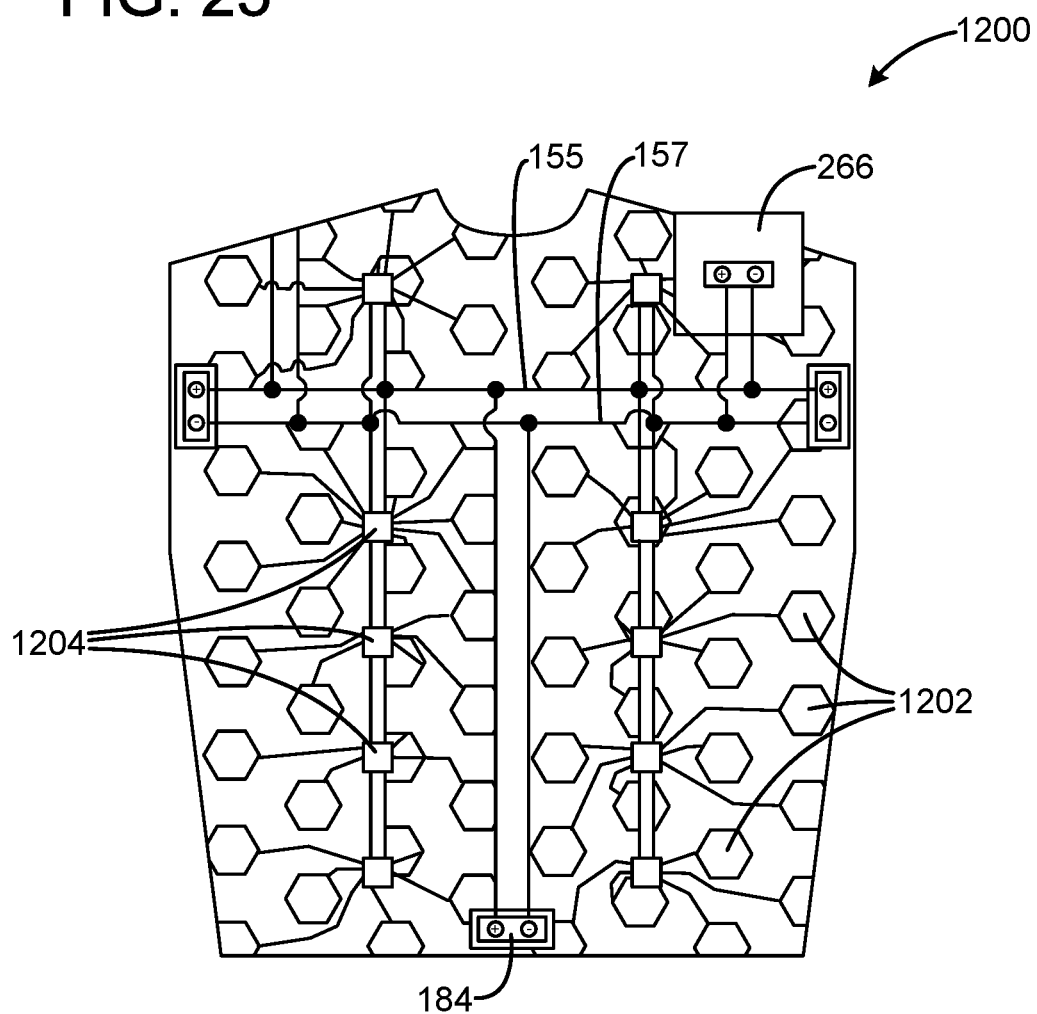
FIG. 25 is a schematic illustration of an alternative embodiment of body suit the present invention that has large electrodes.

FIG. 25 is a schematic view of an alternative embodiment of the body suit 1200 of the present invention that has large electrodes 1202. Body suit 1200 is substantially similar to the body suits shown in FIGS. 4 and 18 and operate in the same way. The body suit 1200 is not described in detail because all the features described in connection with the embodiments shown in FIGS. 4 and 18 also apply to body suit 1200. The only difference between body suit 1200 and the embodiments shown in FIGS. 4 and 18 is that body suit 1200 has very large electrodes 1202 that are connected to sub-control units 1204. The electrodes 1202 could be made so large that they cover substantially all the surfaces on the body suit 1200. Also, the number of sub-control units 1204 is higher compared to the body suit 100 to enable more electrodes in the suit. Only a portion of the body suit is shown in FIG. 25 and the body suit 1200 could be made to cover the entire body as shown in FIG. 4.

It is to be understood that the present invention is not limited to be used in connection with the body suit shown in FIG. 4 and other figures. The body suit 100 is merely an illustrative example. The sub-control units and the electrodes could be used in connection with any garment or piece of fabric. The garment could be separate pieces of fabric that contain the electrodes. It is even possible to place the electrodes directly on the skin of the patient without a garment or fabric holding the electrodes in place. In addition to the upper-body, the arms, pelvis and leg modules, the body suit can also be divided in other ways so that specific areas of the body are stimulated. For example, when the patient to be treated has a handicap that makes it difficult to use the body suit, smaller pieces of elastic or non-elastic materials, that contain electrodes, may be used so that the material pieces are placed on the parts of the patient's body that need stimulation. Another example is when the patient suffers from bed sores, the small pieces of garment or fabric containing the electrodes may be placed on the patient's body/skin so that the wound and its circumference can be stimulated. The small pieces of elastic fabric with electrodes are controlled by the master unit and each small piece is controlled by sub-control units that in turn control the electrodes in the same way as described above. The number of sub-controls units is determined by the number of electrodes in the small pieces. It is also possible to use full body sized garment pieces with the same technology so that patients/persons can lie on the large garment piece or so that a portion of the patient's body can lie on the garment to stimulate different muscles/nerves without the patient having to get into a body suit. The small pieces can be made to include an extra weight so that a good contact with the electrodes is obtained when the electrodes are placed on top of a muscle on the body.

In addition to using electrodes in a garment to read physiological signs, it is also possible to add sensors in the garment or body suit 100 to read accelerations, relative positions, angles and thereby movements of body parts of the person wearing the body suit 100. The present invention is not limited to the use of the body-suit or modules thereof. The body-suit is merely used as an illustrative example, Electrodes and other sensors may also be applied to a belt, band or other devices that are held towards the skin of the body of the user. Motion sensors, angle sensors, temperature sensors and acceleration sensors, and pressure sensors and sensors for reading ECG signals (Electrocardiogram—abbreviated as EKG or ECG) from the heart with electrodes placed on the body suit may be used to measure activities of the body parts of the person wearing the garment 100. Based on these readings, it is possible to decide how to stimulate muscles (either by facilitating contraction or by causing a contraction of certain muscles) and thereby influence/improve or alter the breathing, movement and relative position of the body or body-posture of the person wearing the garment 100. For example, the garment or body-suit 100 or modules of the body suit such as right arm module 102, an upper body module 104, a left arm module 106, a pelvis module 108, a right leg module 110 and a left leg module 112, as described in FIG. 4, could be used that include sensors to, for example, measure movements and positions of the various modules of the body suit 100 and to make sure the posture and movements of the person wearing the body-suit 100 are correct. If the body posture is off, the master unit could be used to stimulate or activate muscles to improve the posture. Similarly, the body suit or modules of the body-suit (that includes motion and positioning sensors) could be used to measure whether the patient is sitting or standing in the same position too long. In this example, the master unit could send signals to stimulate certain muscles such as the hamstrings and butt muscles to increase blood flow and prevent sit-sores.

The body-suit 100 or the modules 102-112 could also include sensors to measure breathing, and to measure the ECG signals received from the heart and to measure vibration caused by snoring. The master unit could then send stimulation signals to stimulate muscles to facilitate breathing or send an alert signal to the user if the user stops breathing. It is also possible to send signals that create a nuisance to the user of the body-suit or modules to influence or encourage the user to sleep on the stomach or the side, as opposed to sleeping on the back to reduce snoring. The same body-suit or modules could be used to stimulate the genital nerves and activate muscles to improve incontinence or postpartum urinary incontinence and even to prevent or reduce sexual orgasm disorders. The garment 100 may also be used to perform a real time gait analysis and adjust the stimulation of muscles to improve walking, running and breathing and also to measure improvements in real time. Stimulation socks (that include sensors) may be used to measure pressure areas under the foot plant to enable a more precise gait analysis.

By using different sensors and using electrodes as sensors placed in the garment/body-suit 100 or separate modules 102, 104, 106, 108, 110, 112 of the body-suit (as shown and described in FIG. 4) such as jacket, sleeves, gloves, pants, underwear, leg garment parts, socks and head-gear that all include sensors, it is possible to analyze how different stimuli affect the body of the wearer of the garment 100 when the muscles of the user wearing the garment are stimulated. By analyzing the measured signals received from different sensors/electrodes and with the knowledge of which stimulations are being carried out, the master unit 266 can automatically adjust the stimulation so that an optimal effect is obtained when the stimulation is running on the body of the user wearing the garment or body-suit 100 or modules of the body suit, as described in FIG. 4. By using the measured input from the sensors, it is possible to create regulatory loops in the software of the master unit 266 that automatically adjusts the stimulation by reading signal from sensors/electrodes over time for better results.

Preferably, the software is self-adjusting towards optimal stimulation to assist the user's body to achieve the desired movements of the body parts of the user. It is possible to run different programs in the master unit to accomplish different stimuli to resolve certain problems. It is also possible to run predetermined stimuli and automatically adjust stimuli for specific disorders. Sensors can be integrated into the garments or modules of the garments. It is also possible to use separate stimulation units that are not part of the garment and apply the stimulation units onto muscles that require stimulation.

By using sensors that are integrated into the garment or body-suit 100 or modules of the garment, it is possible to sense or determine the position of the body of the person wearing the garment 100. Stimulation signals to muscles of the user can then be used to alter the body position or the stimulation signals may be used to indicate or alert the user about the need to alter or correct the body position. For example, it may be desirable to cause the person to change a position that can cause excessive wear and tear on the body. It is also possible to measure any change of the body position from an optimal position and when the current position deviates too much from the optimal position, the master unit can send stimulations to the muscle of the user to cause the user to change position to be closer to the optimal position.

It is also possible to simply to inform the user about need for changing his/her position. This can be used to prevent wear and tear injuries on the body. For example, a worker at a conveyor belt or a driver who drives for long periods of time may be standing or sitting in a wrong body position that should be corrected. If a worker/driver is wearing the garment, muscles can be stimulated so that the worker/driver returns to a good body posture. Also, the use of the garment 100 makes it possible to sense when a user is about to fall asleep by sensing changes in position of the body or other signals that indicate that the user is about to fall asleep. It is then possible to stimulate muscles of the user so that the user does not fall asleep.

By measuring movements of the body of a user wearing the garment and using different types of stimulation to control the movement of the body parts of the user it is possible improve the movements and to make them more optimal. The stimulation can be electrical stimulation pulses sent to the muscles of the user wherein the pulses have different frequencies and variable amplitude, current and pulse lengths. It is also possible to use vibrators or acoustic signals to inform the user that the position of the body or body part is not correct.

It is also possible to receive and measure electrical signals sent from the brain and the sensors can then sense and compare actual physical movements of body parts by using motion sensors, angle sensors, temperature sensors, acceleration sensors and ECG signal from the heart sensed from different body parts and compare those with the electrical signals received from the brain. More particularly, it is possible to determine the sweet-spot for relaxing an antagonist muscle and how to contract an agonist muscle safely. This could involve reading EEG signals from brain and the signals from measuring the breathing and measuring the heart ECG signal.

Electroencephalography (EEG) is a method of recording the spontaneous electrical activity of the cerebral cortex using electrodes. In other words, by using sensors on the head of the user that sense and receive signals from the head, it is possible to determine changes in the EEG signals from the head while the muscles are being relaxed or stimulated to approach optimal stimulation or stimulations. By slowly increasing the strength of the stimulation signals to one muscle or nerve at a time while registering the EEG signals, it is possible to determine changes of the EEG signals during the muscle stimulation or relaxation. When a change of the EEG signals occurs, it may be desirable to either stop or lower the level of the stimulation slightly in order not to continue changing the EEG signals. The stimulation level that causes the EEG signals to start changing may be treated as the optimal "sweet-spot" stimulation strength for that muscle/nerve that is being stimulated. It is then possible to stop the stimulations of the first muscle and start stimulating a second muscle/nerve in the same way until the sweet spot for the second muscle is also found. It is then possible to go through and stimulate selected muscles of the user in the same way and determine the stimulation strength that is desired for each muscle. This information can be used in a stimulation program that can be used to stimulate the selected muscles/nerves.

The optimal stimulations (sweet-spot) may, for example, relate to accomplishing an optimal contraction or relaxation of a muscle or as pain relief or regeneration/recuperation. It is also possible to create software that automatically searches for optimal stimulation strengths for selected muscles/nerves of a patient by measuring the EEG signals while at the same time stimulating the muscles so that the program can vary the stimulation strength for each muscle/nerve to find the sweet-spot for each muscle/nerve. It is also possible to create a program that reads signals from the heart ECG and stimulates to enhance the respiratory function. For example, the frequency of the ECG signal may be measured i.e. to measure how the heart rate (frequency) increases during inhaling and how the heart rate (frequency) decreases during exhaling. For example, it is then possible to provide assistance to the user of the garment or body-suit by electrical stimulation to improve breathing by stimulating during inhalation and stop the stimulation during exhalation.

Figure 26:
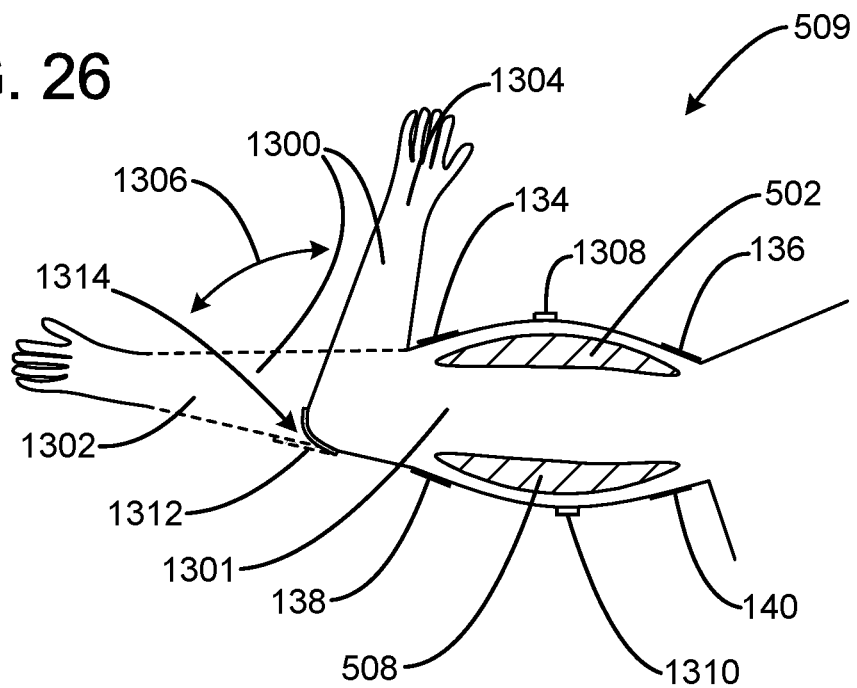
FIG. 26 is a schematic cross-sectional view of an arm module of the present invention.

With reference to FIG. 26, the arm 509 is shown. FIG. 26 is substantially similar to FIG. 9 and all information that applies to FIG. 9 also applies to FIG. 26. The main difference is that FIG. 26 focuses on measuring the position and movement of the arm 509. The underarm 1300 of the arm 509 is movable between a stretch out position 1302 and an upright angular position 1304 and indicated by the double arrow 1306. The user preferably wears the arm module 102, that includes many electrodes, over the arm 509. The module 102 includes an upper motion and position sensor 1308 that senses the position and whether the muscle/nerve 502 moves and a lower motion and position sensor 1310 that senses the position and whether the muscle/nerve 508 moves. The module 102 also includes a sensor 1312 at an elbow 1314 of the module 102 that senses the position and whether the arm is being or has been bent at the elbow 1314. For example, the sensors make it possible to sense and measure how the arm 509 including the underarm 1300 have moved as a result of stimulation of the muscles/nerves 502, 508 on upper-arm 1301 by sending signals to the electrodes 134, 136 and electrodes 138, 140, as described in detail in FIG. 9. In other words, the sensors show the resulting movements of the stimulation of the muscle/nerves 502, 508 and these results can then be compared to the movements that were intended when the electrodes were stimulated. As described earlier, the muscles can be stimulated to relax and by increasing the stimulation, the muscles can cause a change or movement of the arm 509 and under-arm 1300. The master unit 266 may include an algorithm that can be used so that the master unit can learn by analyzing the actual movement compared which stimulation signals work best to accomplish an intended movement of the arm 509 and the underarm 1300. It may also be possible to measure the amount of relaxation of a muscle by using the sensors 1308, 1310 and 1312 by, for example, measuring the arm position or the surface tension at the muscle (pressure sensors) or whether the muscle is expanded or collapsed. The strength, frequency, length of the stimulation signal may be adjusted, as described in detail regarding FIG. 9. For example, if there is no movement of the arm after a first stimulation then a second stronger stimulation may be used to cause the arm or under-arm to move as intended. The arm may be very tense or locked in the angled position 1304 and by relaxing the correct muscles (such as muscle 502 or muscle 508) the arm relaxes so that the underarm 1300 moves towards position 1302. The strength and other variables of the stimulation signal can be adjusted based on the resulting relaxation or movements of the muscles in the arm. It may also be possible to receive and analyze EEG signals from the brain and continuously adjust the stimulation of the muscles based on the EEG signals received in order to minimize the changes of the EEG signals, as mentioned above. This information can then be saved in a database in order to develop standard stimulation signal criteria based on statistical data for various muscle relaxation and muscle movements.

Figure 27:
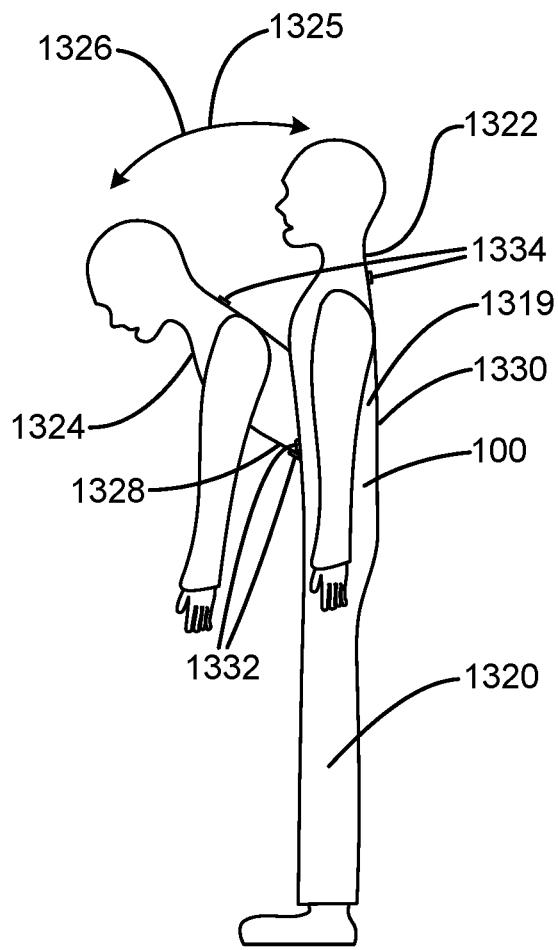
FIG. 27 is a side view of a standing person wearing the body-suit of the present invention.

FIG. 27 illustrates how the body posture of an upper body 1319 of a person 1320 may change from an upright body posture 1322 to an undesirable forward leaning body posture 1324, as indicated by double arrow 1326. The length of the arrow 1326 may represent a range 1325 of acceptable body postures of pre-stored desirable positions. When the upper body 1319 is outside this range 1325, as set in the software, the body posture should be corrected until the upper body 1319 is inside the range 1325 as set in the software in the master unit or sub-control unit. One goal is to stimulate muscles of the person 1320 wearing the body suit 100 or a module (such as upper body module) of the garment or body-suit so that his body posture moves from posture 1324 (that is slightly outside the range 1325) to be within the range 1325 towards the most desirable posture 1322. For example, muscles in the stomach area 1328 and the back area 1330 may be stimulated to accomplish the movement towards the upright position 1322. A position and/or motion sensor 1332, 1334 may be placed on the suit 100 to detect and measure movements of the person. It may also be possible to first detect the incorrect body posture i.e. the upper body 1319 is outside the acceptable range 1325, and merely notify the person 1320 that the body posture should be corrected without electrical stimulation such as by using sound or vibration. It is also possible to use a lower limit for starting the stimulation and an upper limit for stopping the stimulation. These limits may be set in the software on the master unit or sub-control unit. It is also possible to add a time to the software that allows a certain amount of time outside the restriction area before the stimulation starts to correct or assist the person wearing the body-suit or garment 100.

Figure 28:
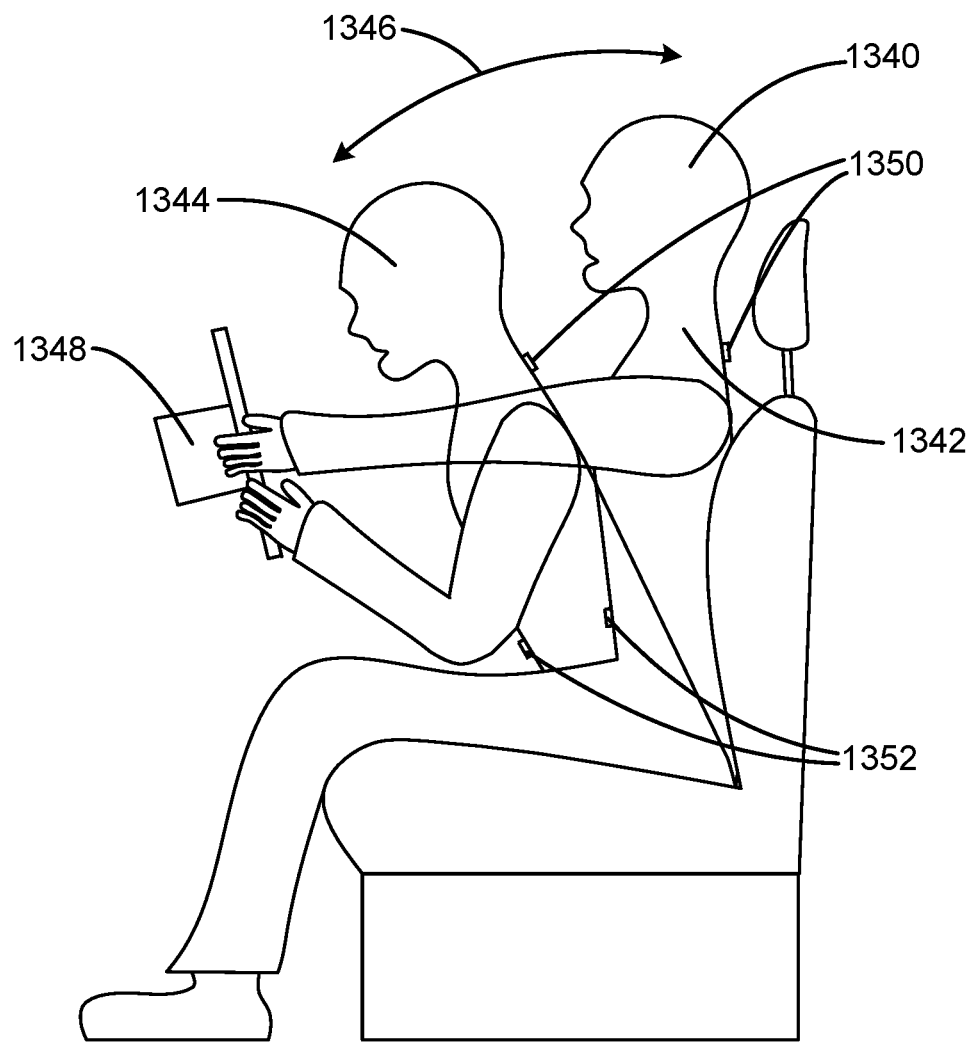
FIG. 28 is a side view of a sitting person who is electrically connected to electrodes of the present invention.

FIG. 28 illustrate how the body posture of a person 1340 may change from an upright sitting position 1342 to a forward leaning position 1344, as indicated by double arrow 1346. For example, the forward leaning position 1344 may indicate that the person is about to fall asleep while driving a car 1348. The electronics and master unit described above can either stimulate muscles to move the person 1340 from the position 1344 to the upright position 1342 or the person may be alerted by vibration or a sound. The person 1340 may have sensors 1350, 1352 placed on the clothing or body suit 100 or one of the body suite modules to measure the position and movement of the upper body of the person 1340. The sensors can thus be used to first determine that the person is in an undesirable position. The sensors can also be used to determine the position of the person as feedback after muscles have been stimulated or after the person has been alerted about the incorrect position. It may also be possible to first detect the incorrect body posture and merely notifying the person 1340 that the body posture should be corrected without electrical stimulating such as by using sound or vibration.

In operation, a garment or body-suit 100 worn by the patient is provided. The garment 100 has a first sub-control unit 122 (see FIG. 4) electrically connected to a first electrode 134 and a second electrode 136 placed at a first muscle or first nerve 502 of the patient and a third electrode 138 and a fourth electrode 140 placed at a second muscle or second nerve 508. The first sub-control unit 122 is preferably electrically connected to the master unit 266. The garment 100 has sensors 1308, 1310, 1312, 1314 attached to the garment and electrically connected to the first sub-control unit 122. The sensors measure a position or movement of the patient wearing the garment 100. The master unit 266 or the first sub-control unit 122 receives information about the position or movement and compare the position or movement to an acceptable interval 1325 of pre-stored desirable positions or movements. The interval may be stored in the master unit 266 or the first sub-control unit 122 and represent body positions or body postures that are within an acceptable range or unacceptable range. For example, when the measured position or movement is outside the interval (or unacceptable range) then the master unit 266 or the first sub-control unit 122 sends a stimulation signal 512 to the first muscle 502 to cause or facilitate a contraction of the first muscle 502 in FIG. 25. When the measured position or movement is within the interval the master unit or the first sub-control unit sends no stimulation signals because the body position or body posture of the patient or user is acceptable and there is no need for correction.

In an alternative embodiment, the method further comprises the step of the sensor measuring an acceleration of a body part such as under-arm 1300 associated with the first muscle 134.

In an yet another embodiment, the method further comprises the step of the sensor 1314 measuring an angle between an upper-arm 1301 and of the body part (under-arm) 1300 associated with the first muscle 502.

In another embodiment, the method further comprises the step of the master unit 266 sending stimulation signals to a set of muscles to move a body part of the patient from the position to be within the interval of pre-stored desirable positions.

In yet another embodiment, the method further comprises the step of the sensor measuring a body posture of the patient.

In an alternative embodiment, the method further comprises the step of the sensor measuring a new position after the first muscle or first nerve has been stimulated by the stimulation signal. The master unit 266 may then send a second stimulation signal to the first muscle or first nerve depending upon the new position i.e. depending on how much the first stimulation signal affected the position. The second subsequent stimulation signal may be stronger than the first stimulation signal such as by using a higher voltage/current, higher frequency or longer pulse length. The specific characteristics of the second subsequent stimulation signal is determined by the master unit 266 that is based on a feedback signal related to the resulting movement from the first stimulation signal. The master unit 266 may also decide to stimulate other muscles by sending stimulation signals to additional electrodes.

In another embodiment, the method further comprises the step of the master unit sending a second subsequent stimulation signal to cause an increase of blood flow in the first muscle.

In yet another embodiment, the method further comprises the step of the sensor measuring breathing of the patient and stimulation helps the body to breathe correctly.

In another embodiment, the method further comprises the step of sensor measuring and analyzing movements of body parts of the patient in real time.

While the present invention has been described in accordance with preferred compositions and embodiments, it is to be understood that certain substitutions and alterations may be made thereto without departing from the spirit and scope of the following claims.

We claim:

1. A method for treating a patient, comprising:
   providing a control unit electrically connected to a connection board having connection pads;
   providing a garment worn by the patient, the garment having a connection unit having connection elements, the connection board having fastening means for detachably connecting the connection pads to the connection elements, the connection unit being electrically connected to a first electrode and a second electrode placed at a first agonist muscle or first nerve of the patient and a third electrode and a fourth electrode placed at a second agonist muscle or second nerve, the garment having sensors attached to the garment and electrically connected to the connection unit and the connection board;

at least one sensor of the sensors measuring position, electrical signals or movement of the patient wearing the garment;

the control unit receiving information about the position or movement and comparing the position, electrical signals or movement to an interval of pre-stored positions, electrical signals levels or movement;

when the position, electrical signals or movement is outside the interval, the control unit sending through the connection unit a first stimulation signal configured to stimulate the first agonist muscle without shortening the first agonist muscle and therefore preventing a contraction of the agonist first muscle to cause or facilitate a relaxation of the second agonist muscle;

when the position, electrical signals, or movement is within the interval, the control unit sending no stimulation signals;

at least one sensor of the sensors measuring a body posture of an upper body of the patient;

determining that the body posture of the upper body is outside a predetermined range; and stimulating the first agonist muscle until the first agonist muscle moves the body posture from the outside of the predetermined range to an inside of the predetermined range.

2. The method of claim 1 wherein the method further comprises the step of at least one sensor of the sensors measuring an acceleration of a body part associated with the first agonist muscle.

3. The method of claim 1 wherein the method further comprises the step of at least one sensor of the sensors measuring an angle of the body part associated with the first agonist muscle.

4. The method of claim 1 wherein the method further comprises the step of the control unit sending a subsequent stimulation signal configured to stimulate a set of muscles to move a body part of the patient from the position to be within the interval of pre-stored positions.

5. The method of claim 1 wherein the method further comprises the step of at least one sensor of the sensors measuring a new position after the first agonist muscle has been stimulated by the first stimulation signal.

6. The method of claim 1 wherein the method further comprises the step of the control unit sending a subsequent stimulation signal to cause an increase of blood flow in the first agonist muscle.

7. The method of claim 1 wherein the method further comprises the step of at least one sensor of the sensors measuring breathing of the patient.

8. The method of claim 1 wherein the method further comprises the step of at least one sensor of the sensors measuring and analyzing movements of body parts of the patient in real time.

9. A method for treating a patient, comprising:

providing a control unit electrically connected to a connection board having connection pads;

providing a garment worn by the patient, the garment having a connection unit having connection elements, the connection board having fastening means for detachably connecting the connection pads to the connection elements, the connection unit being electrically connected to a first electrode and a second electrode placed at a first agonist muscle or first nerve of the patient and a third electrode and a fourth electrode placed at a second agonist muscle or second nerve, the garment having sensors attached to the garment and electrically connected to the connection unit and the connection board;

at least one sensor of the sensors measuring position, electrical signals or movement of the patient wearing the garment;

the control unit receiving information about the position or movement and comparing the position, electrical signals or movement to an interval of pre-stored positions, electrical signals levels or movement;

when the position, electrical signals or movement is outside the interval, the control unit sending through the connection unit a first stimulation signal configured to stimulate the first agonist muscle without shortening the first agonist muscle and therefore preventing a contraction of the agonist first muscle to cause or facilitate a relaxation of the second agonist muscle;

when the position, electrical signals, or movement is within the interval, the control unit sending no stimulation signals;

at least one sensor of the sensors measuring a body posture of an upper body of the patient;

determining that the body posture of the upper body is outside a predetermined range; and notifying the patient that body posture is outside of the predetermined range by using sound or vibration.

10. The method of claim 9, wherein the method further comprises the step of detecting a change of the body posture of the upper body from an upright sitting position to a forward leaning position, and then stimulating the first agonist muscle to cause movement of the upper body from the forward leaning position to the upright sitting position.

* * * * *